United States Patent [19]

Kobayashi et al.

[11] Patent Number: 5,506,256
[45] Date of Patent: Apr. 9, 1996

[54] PROLINE DERIVATIVES POSSESSING PROLYL ENDOPEPTIDASE-INHIBITORY ACTIVITY

[75] Inventors: Koji Kobayashi, Kasugai; Kazuhiko Nishii, Takatsuki; Kunio Iwata, Takatsuki; Itsuo Uchida, Takatsuki, all of Japan

[73] Assignees: Yoshitomi Pharmaceutical Industries, Ltd.; Japan Tobacco Inc., both of Japan

[21] Appl. No.: 26,311

[22] Filed: Feb. 26, 1993

Related U.S. Application Data

[63] Continuation-in-part of Ser. No. 883,116, May 14, 1992, abandoned, which is a continuation-in-part of Ser. No. 734,692, Jul. 23, 1991, abandoned, and a continuation-in-part of PCT/JP92/01711, Dec. 25, 1992.

[30] Foreign Application Priority Data

| Jul. 27, 1990 | [JP] | Japan | 2-197835 |
| Dec. 27, 1990 | [JP] | Japan | 2-418334 |
| Dec. 27, 1991 | [JP] | Japan | 3-361355 |

[51] Int. Cl.$^6$ .................. A61K 31/40; C07D 403/06; C07D 403/14
[52] U.S. Cl. .................. 514/422; 548/518; 548/524
[58] Field of Search ............... 514/422; 548/524, 548/518

[56] References Cited

U.S. PATENT DOCUMENTS

| 4,810,721 | 3/1989 | Saitoh et al. | 514/422 |
| 4,857,524 | 8/1989 | Furukawa et al. | 514/227 |
| 4,857,537 | 8/1989 | Toda et al. | 514/365 |
| 4,880,827 | 11/1989 | Tamoto et al. | 514/423 |
| 4,912,128 | 3/1990 | Henning et al. | 514/422 |

FOREIGN PATENT DOCUMENTS

| 0268190 | 5/1988 | European Pat. Off. |  |
| 0296040 | 12/1988 | European Pat. Off. |  |
| 0345428 | 12/1989 | European Pat. Off. |  |
| 60-188317 | 9/1985 | Japan. |  |
| 62-148467 | 7/1987 | Japan. |  |
| 2270557 | 11/1987 | Japan | 548/518 |
| 64-42475 | 2/1989 | Japan. |  |
| 64-42465 | 2/1989 | Japan. |  |
| 1-230578 | 9/1989 | Japan. |  |
| 2-28149 | 1/1990 | Japan. |  |
| 0304085 | 12/1990 | Japan | 548/518 |

OTHER PUBLICATIONS

Patent Abstracts of Japan, vol. 11, No. 332, (C–455)(2779) Oct. 29, 1987, Abstract of Japan 62–114957(A).

Patent Abstracts of Japan, vol. 13, No. 273, (C–609)(3621) Jun. 22, 1989, Abstract of Japan 62–225377.

Patent Abstracts of Japan, vol. 11, NO. 332, (C–455)(2779) Oct. 29, 1987, Abstract of Japan 62–114978.

*Primary Examiner*—Joseph Paul Brust
*Attorney, Agent, or Firm*—Wenderoth, Lind & Ponack

[57] ABSTRACT

Novel proline derivatives of the following formula (I)

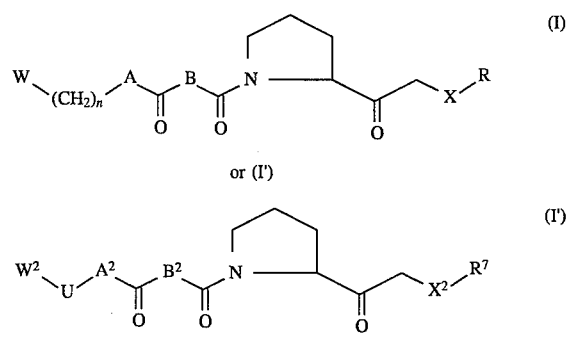

or (I')

wherein each symbol is as defined in the specification, which specifically inhibit prolyl endopeptidase activity and can be used for the prevention and/or treatment of dementia and amnesia as agents which act directly on the central symptoms of dementia.

4 Claims, No Drawings

PROLINE DERIVATIVES POSSESSING PROLYL ENDOPEPTIDASE-INHIBITORY ACTIVITY

This is a continuation-in-part of U.S. patent application Ser. No. 07/883,116 filed May 14, 1992, now abandoned, which is continuation-in-part of U.S. patent application Ser. No. 07/734,692 filed Jul. 23, 1991, now abandoned and a continuation-in-part of International Application No. PCT/JP92/01711 filed Dec. 25, 1992.

FIELD OF THE INVENTION

The present invention relates to novel praline derivatives possessing prolyl endopeptidase-inhibitory activities, method of production thereof and pharmaceutical use thereof.

BACKGROUND OF THE INVENTION

Along with the arrival of an aging society, the medical treatment of senile diseases has been drawing much attention. Above all, senile dementia has become a serious social problem, and various developments have been made in an attempt to provide new pharmaceuticals to cope with the problem. The conventional agents for the treatment of amnesia and dementia have been named obscurely as cerebral circulation improving agents, cerebral metabolism activator or cerebral function improving agents according to their action mechanisms. While they are effective for improving peripheral symptoms such as depression, emotional disturbances, abnormal behavior, etc., they do not show definite effects on the central symptoms of dementia, such as memory disorder, disorientation, and the like. Thus, the development of medicaments which can offer dependable action and effect on these symptoms is earnestly desired.

In the meantime, prolyl endopeptidase; EC, 3.4.21.26 is an enzyme known to act on peptides containing proline and to specifically cleave out the carboxyl side of proline. Further, this enzyme is known to act on neurotransmitters such as thyrotropin-releasing hormone (TRH), substance P and neurotensin, as well as on vasopressin which is presumably concerned with learning and memory process, to cause decomposition and inactivation of them.

In view of the foregoing findings, a compound possessing inhibitory activity on prolyl endopeptidase is expected to suppress decomposition and inactivation of vasopressin, etc., thereby suggesting its potential application to the treatment and prevention of amnesia and dementia as an efficacious medicament which exhibits direct action on the central symptoms of dementia [See Seikagaku, 55, 831 (1983); *FOLIA PHARMACOL. JAPON*, 89, 243 (1987); and J. Pharmacobio-Dyn., 10, 730 (1987)] and also, such compound is expected to suppress decomposition and inactivation of hormones and neurotransmitters such as TRH, substance P, neurotensin, etc., thereby improving various symptoms caused by the decomposition and inactivation of these substances.

In recent years, it has been found that beta amyloid protein shows neurotoxic action in in vitro and in vivo experiments, and that it plays essentially an important role in the onset of Alzheimer's disease. In view of the hypothesis that prolyl endopeptidase is an enzyme which cleaves out beta amyloid from amyloid precursor protein (FEBS Lett., 260, 131–134 (1990), and experiment results substantiating that substance P can suppress neurotoxic action of beta amyloid protein (Proc. Natl. Acad. Sci. USA, 88, 7247–7251 (1991), prolyl endopeptidase inhibitor is speculated to make an effective drug for treating Alzheimer's disease.

Out of the motivation described above, there has been attempted development of prolyl endopeptidase-inhibiting agents, and various proline derivatives are described and disclosed in, for example, Japanese Patent Unexamined Publication Nos. 188317/1985, 148467/1987, 42475/1989, 6263/1989, 230578/1989, and 28149/1990.

SUMMARY OF THE INVENTION

Based on the findings mentioned above, the present inventors have conducted intensive studies to find a compound which possesses amino acid, specifically a proline residue as a fragment, and which specifically inhibits prolyl endopeptidase activity, and have found that novel proline derivatives of the fomula (I) or (I') mentioned below possess specific and strong prolyl endopeptidase-inhibitory activity, which resulted in the completion of the invention.

An object of the invention is to provide a novel compound possessing specific and strong prolyl endopeptidase-inhibitory activities.

Another object of the invention is to provide a pharmaceutical composition useful as a prolyl endopeptidase-inhibitor.

The present invention relates to novel proline derivatives of the following formula (I)

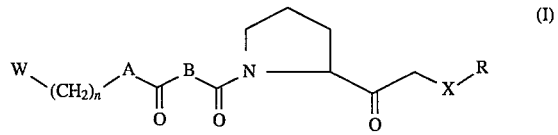

wherein:

A is —O—, —NH—,

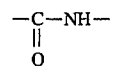

or a single bond;

B is

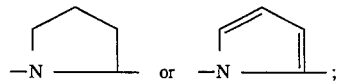

W is

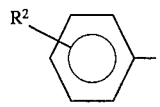

of $CH_3$— where $R^1$ is a hydrogen atom, a halogen atom or a lower alkoxy;

X is —S—, —SO—, —SO$_2$—, —O— or —NH—;

R is

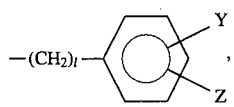

or a lower alkyl having 1 to 5 carbon atoms where 1 is an integer of 0 to 3, Y and Z are the same or different and each is a hydrogen atom, a halogen atom, a lower alkyl having 1 to 5 carbon atoms which may be substituted by fluorine atoms, a nitro, a hydroxyl or a lower alkoxy, and Y and Z may combinedly form a saturated or unsaturated 5- or 6- membered ring selected from the group consisting of furan ring, oxolane ring, 1,3-dioxolane ring, thiophene ring, pyrrole ring, pyrrolidine ring, oxane ring, pyridine ring and benzene ring; and n is an integer of 1 to 6, and to pharmaceutical compositions containing, as an active ingredient, the novel proline derivative (I), which are useful as prolyl endopeptidase-inhibitors.

Also, the present invention relates to novel proline derivatives of the following formula (I')

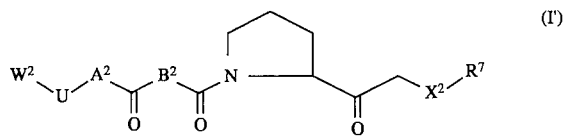

wherein $A^2$ is —O—, —CHR$^8$— or —NR$^9$— (wherein R$^8$ is a hydrogen atom or a hetero ring, and R$^9$ is a lower alkoxycarbonyl(lower)alkyl;

$B^2$ is

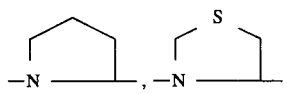

or —NR$^{10}$—CHR$^{11}$—

(wherein R$^{10}$ and R$^{11}$ are the same or different, and each is a hydrogen atom or a lower alkyl);

$W^2$ is phenyl which may be substituted by at least one substituent selected from the group consisting of a halogen atom, a lower alkyl and a lower alkoxy, adamantyl, a lower alkyl or a hetero ring;

U is —O—, —S—, —NH—or —CHR$^{12}$—(wherein R$^{12}$ is a hydrogen atom or a lower alkoxycarbonyl);

$X^2$ is —S—, —SO—, —SO$_2$—, —O—or —NH—; and $R^7$ is

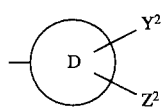

(wherein D is benzene ring or a hetero ring, $Y^2$ and $Z^2$ are the same or different and each is a hydrogen atom, a halogen atom, a lower alkyl which may be substituted by at least one fluorine atom, amino, nitro, hydroxy or a lower alkoxy) with the proviso that when U is —CH$_2$—, at least $W^2$ is adamantyl or a hetero ring, $A^2$ is —CHR$^8$—or —NR$^9$—(wherein R$^8$ is a hereto ring and R$^9$ is a lower alkoxycarbonyl(lower)alkyl), $B^2$ is thiazolidine, or $R^7$ is a hereto ring.

Further, the present invention relates to pharmaceutical compositions useful as prolyl endopeptidase-inhibitors, which contain the proline derivative (I') mentioned above as an active ingredient.

DETAILED DESCRIPTION OF THE INVENTION

Various substituents used in the present invention are defined as follows.

"Halogen atom" means chlorine, bromine, fluorine or iodine.

"Lower alkyl" means a straight or branched-chain hydrogen carbon having 1 to 5 carbon atoms, and examples thereof include methyl, ethyl, propyl, isopropyl, butyl, sec-butyl, tert-butyl, and pentyl "Lower alkoxy" is an alkoxy having 1 to 5 carbon atoms, and examples thereof include methoxy, ethoxy, propoxy, isopropoxy butoxy, sec-butoxy, and tert-butoxy.

"Lower alkoxycarbonyl" is an alkoxycarbonyl having 2 to 6 carbon atoms, and includes, for example, methoxycarbonyl, ethoxycarbonyl, propoxycarbonyl, isopropoxycarbonyl, butoxycarbonyl, sec-butoxycarbonyl, and tert-butoxycarbonyl.

"Lower alkoxycarbonyl(lower)alkyl" is an alkyl having 1 to 5 carbon atoms, which is substituted by lower alkoxycarbonyl as mentioned above. Examples thereof include methoxycarbonylmethyl, methyl, 2-(methoxycarbonyl) ethyl, 3-(methoxycarbonyl)propyl ethoxycarbonylmethyl, 2-(ethoxycarbonyl )ethyl, 3-(ethoxyethyl, and 3-(propoxycarbonyl )propyl.

"Phenyl which may be substituted by at least one substituent selected from the group consisting of a halogen atom, a lower alkyl and a lower alkoxy" means phenyl which may be substituted by one or two substituents selected from the group consisting of a halogen atom, a lower alkyl and a lower alkoxy as mentioned above, and specifically include, for example, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl 4-iodophenyl, 2-methylphenyl, 3-methylphenyl, 4-methylphenyl, 2ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-methoxyphenyl, 3-methoxyphenyl, 4-methoxyphenyl, 2-ethoxyphenyl, 3-ethoxyphenyl, 4-ethoxyphenyl, 3,4-dichlorophenyl, 3,4-difluorophenyl, 3,4-dibromophenyl, 3,4-diiodophenyl, 3,4-dimethylphenyl, 3,4-diethylphenyl, 3,4-dipropylphenyl, 3,4-diisopropylphenyl, 3,4-dibutylphenyl, 3,4-dimethoxyphenyl, 3,4-diethoxyphenyl, 3,4-dipropoxyphenyl, 3,4-diisopropoxyphenyl, and 3,4-dibutoxyphenyl.

"Hereto ring" is a saturated or unsaturated 4- to 7-membered ring having one or more hetero atoms (nitrogen atom, oxygen atom, or sulfur atom), and examples thereof include pyrrole, furan, thiophen, pyrazole, isoxazole, imidazole, oxazole, thiazole, pyridine, pyrimidine, pyrazine, azetidine pyrrolidine, tetrahydrofuran, piperidine, piperazine morpholine, and homopiperidine.

The novel proline derivatives of the formula (I) of the invention can be produced, for example, by the reaction processes shown below.

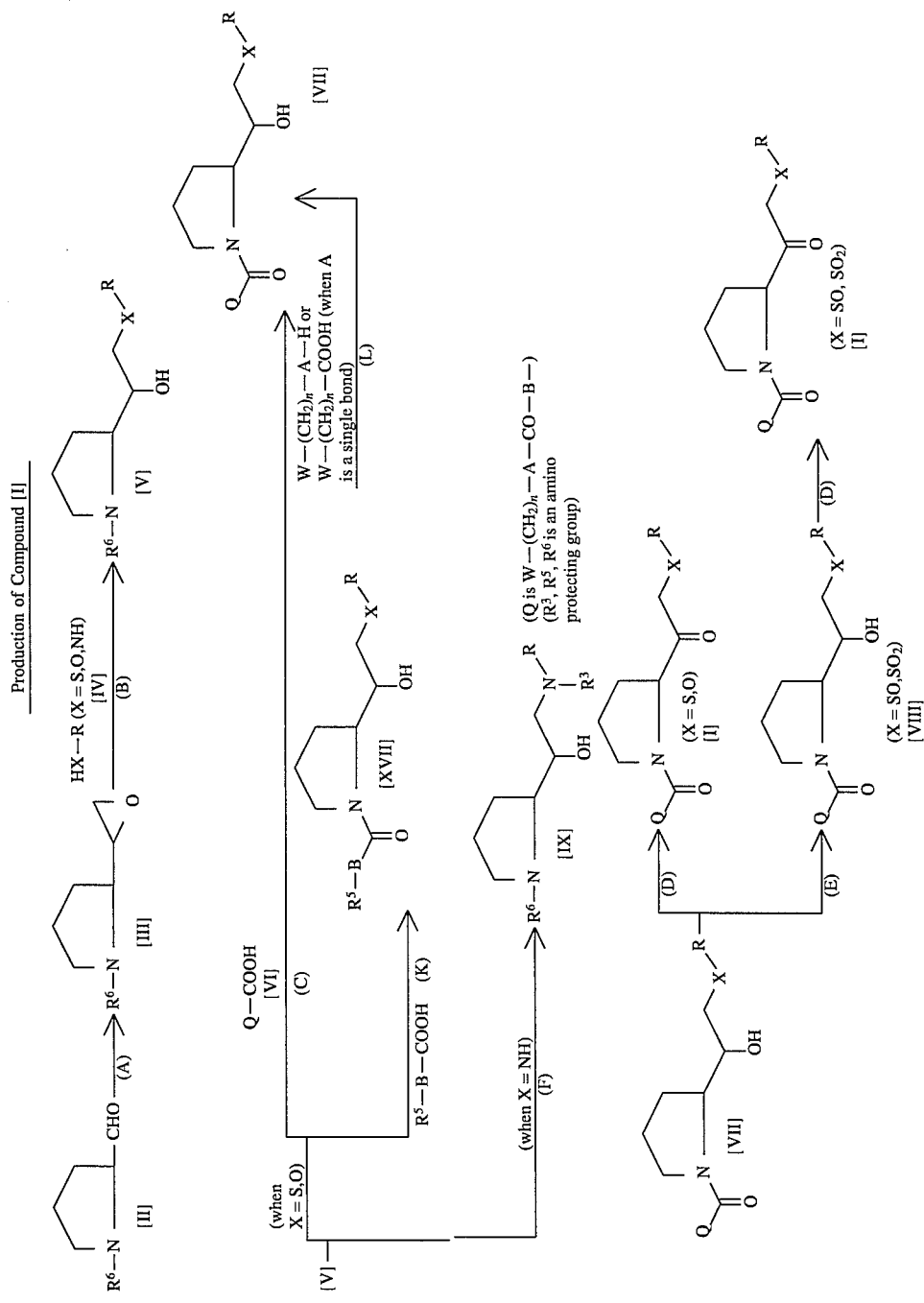

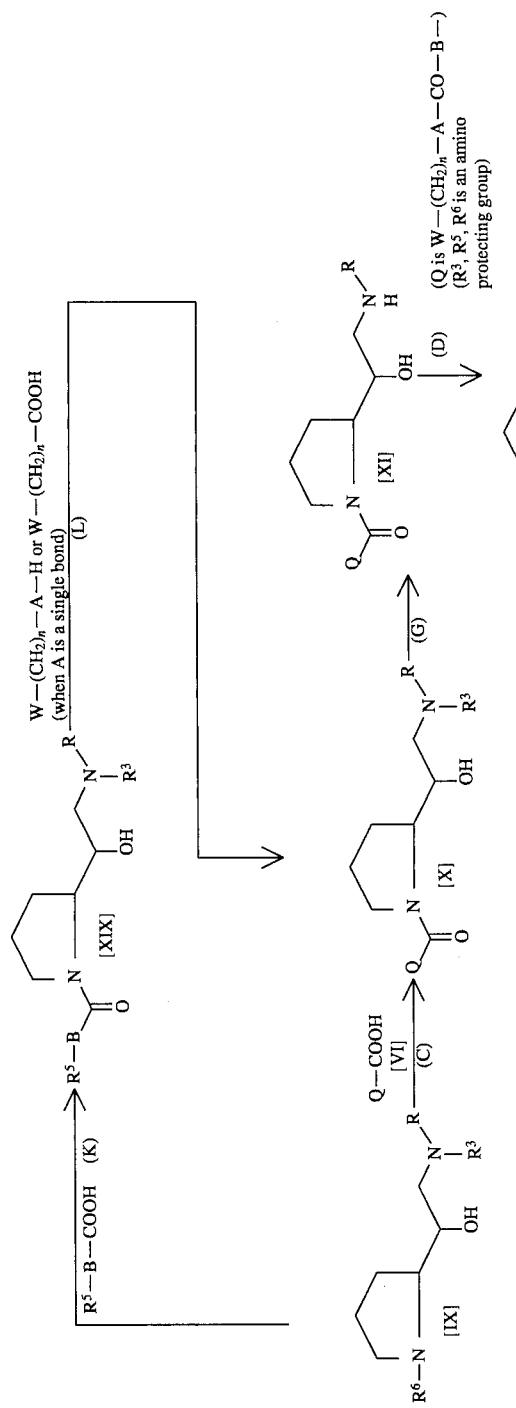

Hereunder follow detailed descriptions in respect of each reaction process. The symbols A, B, W, X, R and n are as defined above.

Reaction (A)

A compound of the formula (II) is reacted with a sulfur ylid derived from trimethylsulfonium iodide or trimethyloxo-sulfonium iodide in the presence of a strong base, to obtain an epoxide of the formula (III). This reaction can be conducted, for example, by obtaining a sulfur ylid from the above-mentioned sulfonium salt using n-butyllithium or sodium hydride-dimethyl sulfoxide in an inert solvent such as tetrahydrofuran, 1,4-dioxane and hexane, followed by reaction of the obtained sulfur ylid with a compound (II). The reaction temperature is between −70° C. and reflux temperature, preferably between −10° C. and room temperature.

$R^6$ here means amino protecting group such as benzyloxycarbonyl, tert-butoxycarbonyl, and 9-fluorenylmethyloxycarbonyl, and any amino protecting group can be used so long as the reaction is not adversely affected.

Compound (III) may be also obtained by epoxidation, using a peracid, of an olefin obtained by subjecting a compound (II) to Wittig reaction. Specifically, methyltriphenylphosphonium halide is reacted with n-butyllithium in an inert solvent such as tetrahydrofuran, and diethyl ether to give a corresponding ylid, which is then reacted with a compound (II) to give an olefin. The reaction temperature is suitably from −70° C. to reflux temperature. The olefin obtained is subjected to an epoxidation using an organic peracid such as m-chloroperbenzoic acid or aqueous hydrogen peroxide in a solvent such as methylene chloride, benzene, hexane, and methanol at a temperature between −20° C. and reflux temperature, preferably between 0° C. and room temperature, thereby to give the object compound (III).

Reaction (B)

A compound of the formula (III) is reacted with a compound (IV) of the formula HX-R (X=S, O, NH) in a suitable solvent in the presence or absence of a base, to obtain an alcohol compound of the formula (V). Detailedly speaking, a reaction with HX-R wherein X is sulfur atom is conducted in the presence of a tertiary amine such as triethylamine and N-methylmorpholine in a solvent such as methanol, 1,4-dioxane and dimethylformamide. A reaction with HX-R wherein X is an oxygen atom is conducted using sodium methoxide in methanol, or using sodium hydride in a solvent such as 1,4-dioxane and N,N-dimethylformamide to convert HO-R to anion $\ominus$O—R, followed by reaction with (III). A reaction with HX-R wherein X is NH is conducted in a solvent such as methanol and 1,4-dioxane. The reaction temperature is between room temperature and reflux temperature in each case described above.

Reaction (C)

Compound (VII) is obtained by removing an amino protecting group $R^6$ from the intermediate represented by the formula (V) by a known method, and subjecting the resultant compound to condensation with a compound of the formula (VI). In the same manner, Compound (X) can be obtained from a compound of the formula (IX).

Removal of the amino protecting group $R^6$ can be conducted by a known method. For example, when $R^6$ is tert-butoxycarbonyl (Boc), elimination of the protecting group can be performed by acid treatment of an intermediate of the formula (V) or (IX) with the use of hydrobromic acid/acetic acid, hydrochloric acid/1,4-dioxane, formic acid, hydrochloric acid/acetic acid, trifluoroacetic acid, etc. at a temperature between −30° C. and 70°C., preferably between 0° C. and 30° C.

Then, the thus-obtained deprotected compound is subjected to a condensation reaction with a compound (VI) to give an amino acid derivative (VII) or (X), wherein Q is W—$(CH_2)_n$—A—CO—B.

A method known per se can be employed for this peptide formation. Examples thereof include a method wherein N,N'-dicyclohexylcarbodiimide (DCC), a water-soluble carbodiimide hydrochloride [1-ethyl-3-(3-dimethylaminopropyl)carbodiimide hydrochloride (EDC.HCl)], etc. is used as a condensing agent, activated ester method, mixed acid anhydride method, and so on.

The reaction proceeds in an inert solvent at a temperature between 0° C. and under heating. Examples of suitable solvents include chloroform, diethyl ether, N,N-dimethylformamide, ethyl acetate, dichloromethane, tetrahydrofuran, and the like.

In the activated ester method, peptide bonds are formed by reacting the above-mentioned compound (VI) with p-nitrophenol, thiophenol, p-nitrothiophenol, N-hydroxysuccinimide, etc. in an inert solvent in the presence of DCC, thereby affording an activated ester (e.g. an ester with N-hydroxysuccinimide), and with or without isolation, further reacting the same with the above-mentioned deprotected compound in an inert solvent at a temperature between 0° C. and 40° C.

In the mixed anhydride method, peptide bonds are formed by reacting the above-mentioned compound (VI) with an acid halide (e.g. pivaloyl chloride, tosyl chloride, oxalyl chloride) or an acid derivative (e.g. ethyl chloroformate, isobutyl chloroformate) in an inert solvent in the presence of a tertiary amine (e.g. pyridine, triethylamine) at a temperature between 0° C. and 40° C., thereby affording a mixed acid anhydride, and further reacting the same with the deprotected compound mentioned above at a temperature between 0° C. and 40° C.

In the DCC method, the desired peptide bonds are formed by reacting the above-mentioned deprotected compound and (VI) in an inert solvent by using DCC, EDC.HCl etc. as a condensing agent in the presence or absence of the tertiary amine mentioned above such as triethylamine, and with or without addition of a suitable additive [e.g. 1-hydroxybenzotriazole (HOBt), N-hydroxy-5-norbornen-2,3-dicarboximide (HONB)].

Reaction (D)

The object compound (I) is prepared by oxidation, with a suitable oxidizing agent, of an alcohol compound of the formula (VII), which is obtained in Reaction (C) above. In the similar manner, the object compound (I) can be obtained by oxidation of a compound of formula (VIII) or (XI) to be mentioned later.

This reaction can be conducted in an inert solvent such as benzene, dichloromethane and N,N-dimethylformamide using pyridinium chlorochromate or pyridinium dichromate in the presence or absence of molecular sieves at a temperature between 0° C. and reflux temperature, preferably between 0° C. and room temperature; or in an inert solvent such as dichloromethane in the presence of oxalyl chloride and triethylamine using dimethyl sulfoxide at a temperature between −80° C. and room temperature, preferably between −80° C. and 0° C.; or in the presence of pyridine, trifluoroacetic acid and dimethylsulfoxide using DCC with or without co-existence of an inert solvent such as benzene at a temperature between 0° C. and room temperature; or with or without co-existence of an inert solvent such as benzene in the presence of a tertiary amine such as triethylamine and dimethyl sulfoxide, using a sulfur trioxide-pyridine complex at a temperature between −10° C. and room temperature.

Reaction (E)

A sulfoxide compound or a sulfone compound of the formula (VIII) is obtained by oxidizing a compound of the formula (VII) wherein X is a sulfur atom with a peracid such as m-chloroperbenzoic acid. For example, a sulfoxide compound and a sulfone compound can be obtained by oxidation in an inert solvent such as dichloromethane, chloroform and benzene using an equivalent and 2 equivalents of m-chloroperbenzoic acid, respectively, at a temperature between −20° C. and reflux temperature, preferably between 0° C. and room temperature.

Reaction (F)

A compound (IX) is obtained by introducing an amino protecting group $R^3$ to a compound of the formula (V) wherein X is NH by a method known in peptide synthesis.

While there are many examples for an amino protecting group $R^3$, those stable against acid treatment for removing Boc group for converting (IX) to (X) should be used when Boc group is used as $R^6$, and they are exemplified by formyl and trifluoroacetyl which are acyl type protecting groups, and 9-fluorenylmethyloxycarbonyl, methylsulfonylethyloxycarbonyl which are urethane type protecting groups. Introduction of these protecting groups can be achieved by a known method (Izumiya, et al., *Pepuchido Gosei no Kiso to Jikken*, Maruzen). For example, introduction of trifluoroacetyl group can be conducted by a reaction of (V) with ethyl trifluoroacetate in a solvent such as methanol in the presence of a tertiary amine such as triethylamine at a temperature between 0° C. and room temperature, preferably at room temperature. In this reaction, $R^3$ may be introduced after protection of free hydroxyl group with an appropriate protecting group, if necessary.

Reaction (G)

A compound (XI) is obtained by removing an amino protecting group $R^3$ from a compound of the formula (X). While the method for removing the amino protecting group $R^3$ varies depending on the kind of the protecting group, a known method in peptide synthesis can be employed. Such removal is mainly achieved by catalytic reduction or base treatment in respect of the aforementioned Reaction (F). For example, removal of trifluoroacetyl group is carried out in a solvent such as methanol using potassium carbonate, sodium carbonate or ammonia as a base at a temperature between 0° C. and reflux temperature, preferably at room temperature.

Preparation of compounds (VII) and (X) conducted by condensation of compounds (V) and (IX), respectively with a compound (VI) may be replaced by the following stepwise reactions. That is, a compound of the formula (XVII) can be obtained by condensation of a compound of the formula $R^5$-B-COOH (wherein $R^5$ is a suitable amino protecting group) with a compound (V) in the same manner as in Reaction (C), which is shown in Reaction (K). Then, as shown in Reaction (L), the amino protecting group $R^5$ is removed from the compound of the formula (XVII) by a known method, after which the compound is reacted with a compound of the formula W—$(CH_2)_n$—A—H (wherein A is O, NH or CONH) or a compound of the formula W—$(CH_2)_n$—COOH (wherein A is a single bond) to give the object compound (VII). In the former, for example, W—$(CH_2)_n$—A—H is reacted with phosgene, diphosgene, trichloromethyl chloroformate, carbonyldiimidazole, or the like in a suitable solvent such as 1,4-dioxane and tetrahydrofuran in the presence of a tertiary amine such as triethylamine at a temperature between −20° C. and room temperature, followed by reaction with a deprotected compound of (XVII). When A is —NH—, the object compound can be produced by reacting W—$(CH_2)_n$—N=C=O with the deprotected compound of the formula (XVII), in a suitable solvent such as dichloromethane, chloroform, and N,N-dimethylformamide in the presence or absence of a tertiary amine such as triethylamine at a temperature between −20° C. and room temperature. If necessary, a free hydroxyl group of compound (XVII) may be in advance protected with a suitable protecting group. When A is a single bond as in the latter, the method described in Reaction (C) above is employed wherein a deprotected compound of the formula (XVII) is condensed with W—$(CH_2)_n$—COOH or the corresponding acid chloride W—$(CH_2)_n$—COCl.

A compound of the formula (X) can be obtained by converting a compound of the formula (IX) to a compound of the formula (XIX) in the same manner as in the above reaction (K), followed by Reaction (L) as described.

An optically active sulfinyl compound of the formula (I) wherein X is —SO—

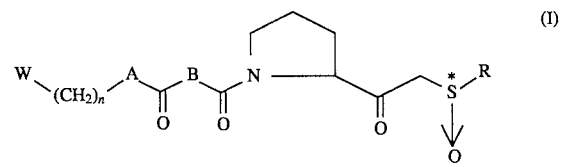

can be synthetically produced by the following steps.

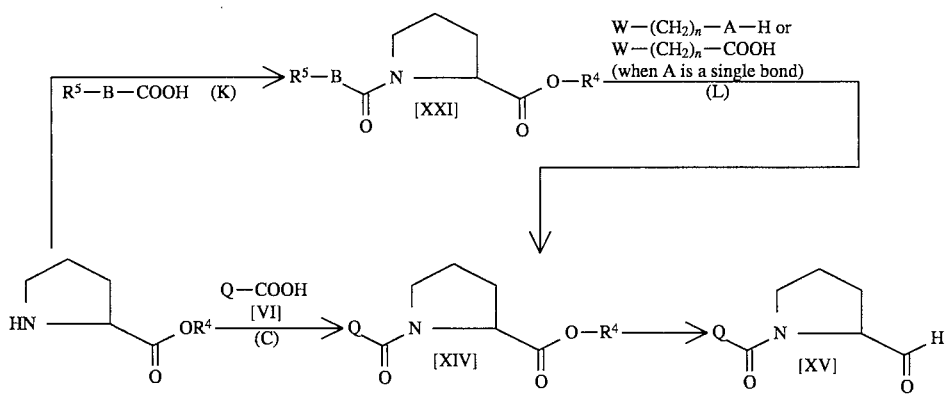

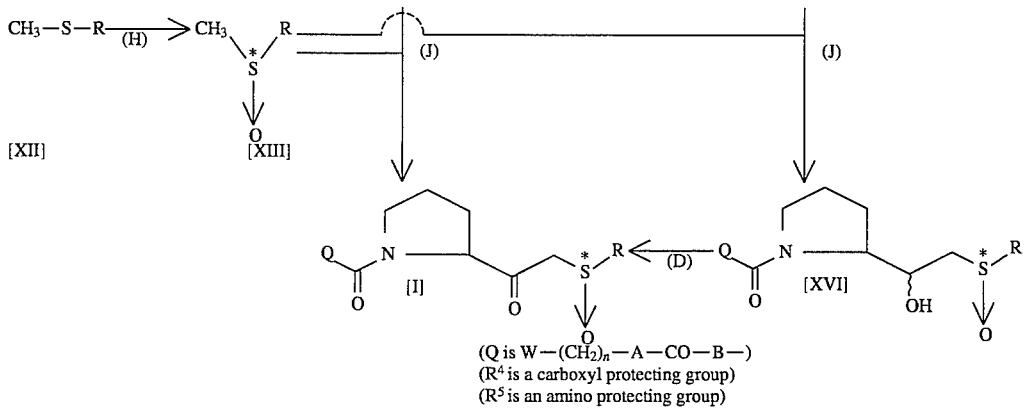

(Q is W—(CH₂)ₙ—A—CO—B—)
(R⁴ is a carboxyl protecting group)
(R⁵ is an amino protecting group)

Each reaction step is detailedly described in the following, wherein A, B, W, R and n are as defined above, and Reactions (C), (D), (K) and (L) are as described above.

Reaction (H)

A compound of the formula (XII) is subjectd to asymmetric oxidation according to a literature method [P. Pitchen et al., J. Am. Chem. Soc., 106, 8188–8193 (1984); S. It. Zhao et al. Tetrahedron, 43, 5135–5144 (1987), etc.] to give an optically active sulfoxide of the formula (XIII). This reaction is conducted, for example, in a solvent such as dichloromethane, 1,2-dichloroethane in the presence of titanium tetraisopropoxide, optically active diethyl tartarate and water using tertbutyl hydroperoxide or cumene hydroperoxide at a temperature of 0° C. or below, preferably at a temperature between −40° C. and −20°C.

Reaction (J)

An optically active sulfoxide of the formula (XIII) is treated with a base to convert the same into the corresponding carbanion which is then condensed with an ester (XIV) or an aldehyde (XV) prepared from Compound (XIV) by a known method to give an optically active sulfinyl compound of the formula (I) or (XVI). This reaction can be carried out by, for example, reacting an optically active sulfoxide (XIII) in an inert organic solvent such as tetrahydrofuran or 1,4-dioxane using a base such as n-butyllithium or lithium diisopropylamide at a temperature between −78° C. and room temperature, preferably 0° C. or below to generate the corresponding carbanion, which is then subjected to condensation reaction with an ester (XIV) or an aldehyde (XV) at a temperature between −78° C. and room temperature, preferably between −78° C. and 20° C.

The compounds to be used as the starting materials, N-protected prolinal (II), HX-R (IV), Q—COOH (VI), R⁵—B—COOH, W—(CH₂)ₙ—A—H, W—(CH₂)₂—COOH, CH₃—S—R (XII) and ester of proline are available as known substances, or can be synthesized with ease from known precursor substances by known methods.

The proline derivatives of the formula (I') of the present invention can be produced by the reaction steps to be shown in the following.

Production of Compound [I']
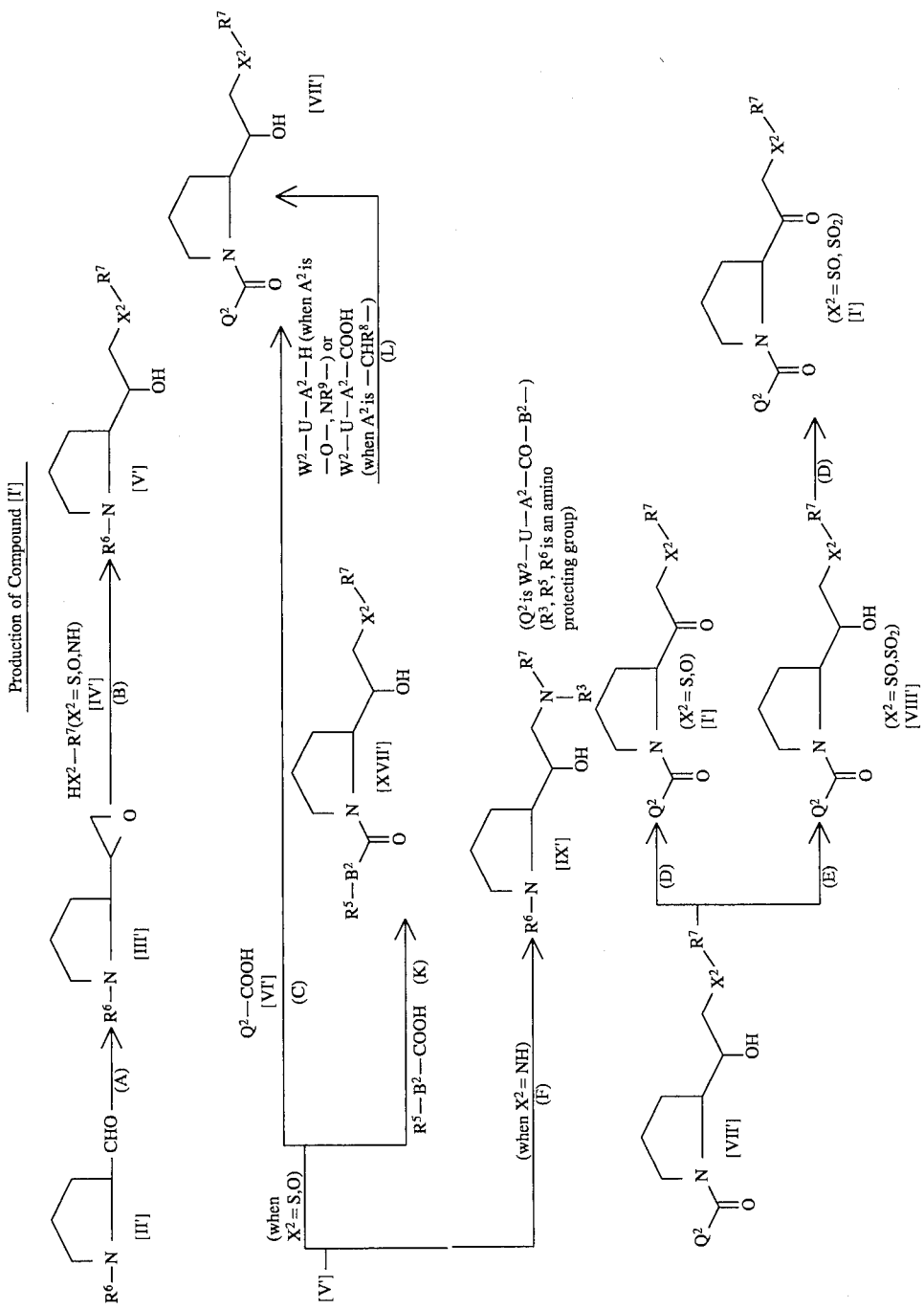

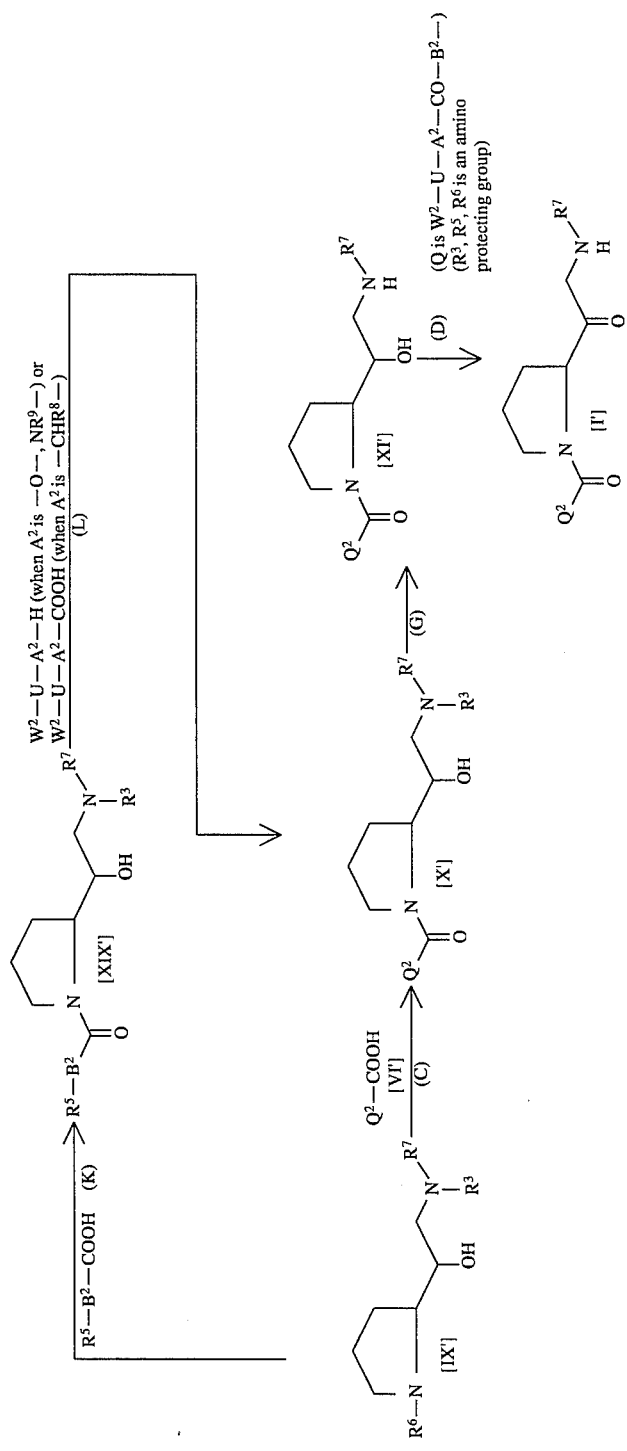

In the preceding reaction charts, $A^2$, $B^2$, $W^2$, U, $X^2$ and $R^7$ are the same as above. As regards Reactions (A)–(G), (K), and (L), they can be performed in the same manner as described for the production of Compound (I).

Optically active sulfinyl compounds of the formula (I') wherein $X^2$ is —SO—

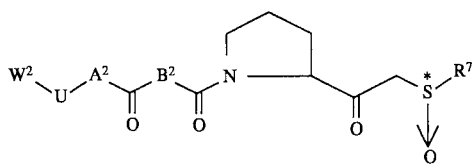

can be produced by the following steps.

according to the purpose. For example, column chromatography, solvent extraction, recrystallization, etc. can be used. The isolation and purification may be conducted at every reaction or upon completion of a few reactions.

A series of compounds mentioned above possess asymmetric center(s) in each molecule. In the present invention, the configuration of each asymmetric center may be R or S, and a mixture of such stereoisomers is also encompassed in the invention. Optically active substances can be obtained respectively by employing an optically active compound as a starting material, or by purification of a mixture of stereoisomers by means of column chromatography, recrystallization, etc.

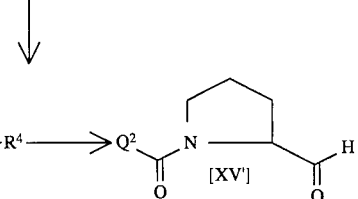

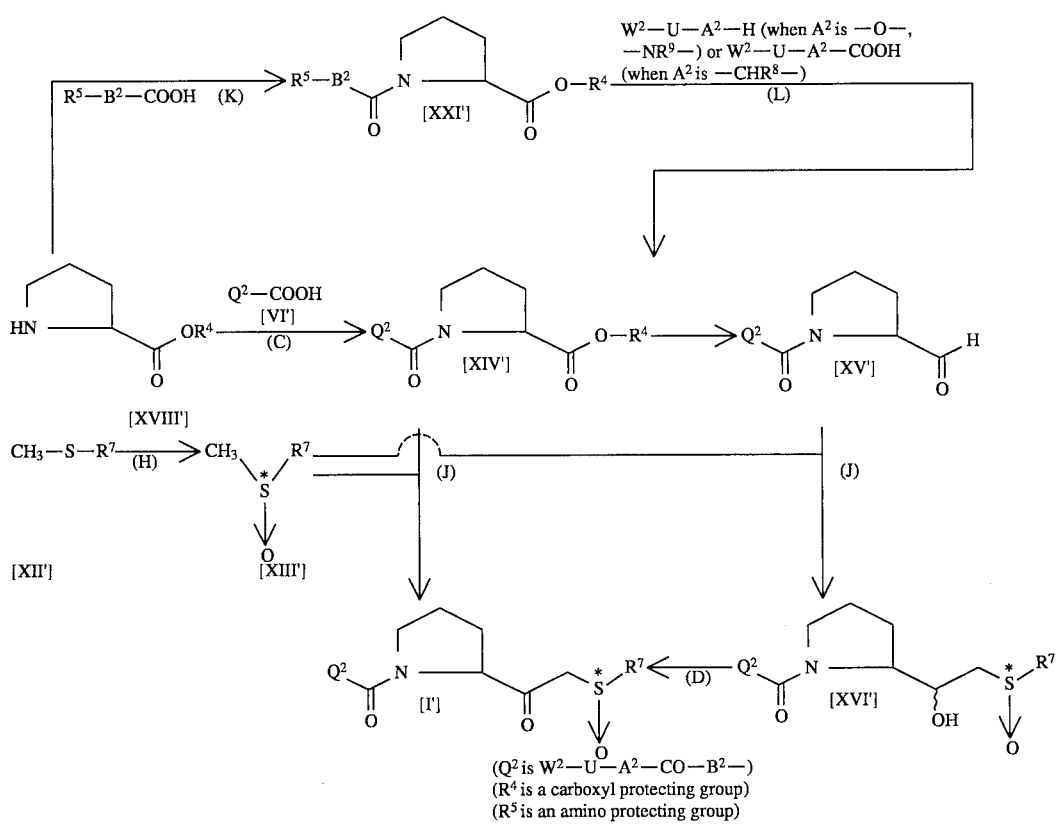

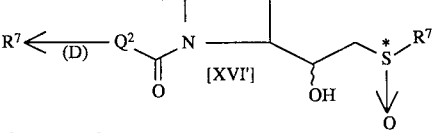

($Q^2$ is $W^2$—U—$A^2$—CO—$B^2$—)
($R^4$ is a carboxyl protecting group)
($R^5$ is an amino protecting group)

In the reaction chart above, $A^2$, $B^2$, $W^2$, U and $R^7$ are the same as above. As regards Reactions (C), (D), (H), (J), (K) and (L), they can be performed in the same manner as described for the production of Compound (I).

The compounds to be used as the starting materials, N-protected prolinal (II'), $HX^2$—$R^7$ (IV'), $Q^2$—COOH (VI'), $R^5$—$B^2$—COOH, $W^2$—U—$A^2$—H, $W^2$U—A—COOH, $CH_3$—S—$R^7$ (XII') and ester of proline (XVIII') are available as known substances, or can be synthesized with ease from known precursor substances by known methods.

In synthesizing the final object compound of the formula (I) or (I'), suitable protecting groups may be introduced at appropriate stages if necessary, and the protecting groups may be removed at appropriate stages, preferably prior to final step reaction (D) or reaction (J).

The compounds of the formula (I) or (I') thus obtained can be isolated and purified from reaction mixture by a conventional method which has been usually employed in the field of synthetic organic chemistry, and selected ad libitum When the compounds of the present invention are used as a pharmaceutical, they are administered systemically or locally, and orally or parenterally.

While the dose varies depending on age, weight, symptom, treatment effect, method of administration, etc., the compounds of the present invention can be administered orally at 1 mg to 500 mg per administration per adult in a single unit dosage or in divided doses daily, or at 0.2 mg to 100 mg per administration per adult once to several times daily.

The compounds of the invention are administered in the form of solid compositions and liquid compositions for oral administration, or injections, suppositories, etc. for parenteral administration.

The solid compositions for oral administration include tablets, pills, capsules, powders, granules, etc. In the solid compositions, at least one active substance is mixed with at least one pharmaceutically acceptable inactive diluent, and excipients, binding agents, rublicants, degrading agents, dissolution enhancing agents, stabilizing agents, and so on may be also contained, if necessary. Tablets and pills may be applied with an enteric coating, if necessary. Capsules include hard and soft capsules.

The liquid compositions for oral administration include solutions, emulsions, suspensions, syrups and elixirs. These liquid compositions contain inactive diluents generally used and may further contain adjuvants such as wetting agents and suspending agents, sweetners, flavors, aromatic agents and preservatives.

The injections for parenteral administration include sterile aqueous or non-aqueous solutions, suspensions and emulsions. At least one active substance is used with at least one inactive aqueous diluent or inactive non-aqueous diluent in admixture, and other adjuvants such as preservatives, wetting agents, emulsifiers, dispersibles, stabilizing agents and dissolution enhancing agents may be also contained. They are normally sterilized by filtration (bacteria-retaining filter, etc.), mixing with sterilizers, or gamma irradiation, or they are, subsequent to such treatments, prepared into solid compositions by lyophilization, and diluted before use with sterile water or sterile diluents for injection.

The present invention is hereinbelow described in detail by way of examples.

The abbreviations used in the examples respectively mean the following:

DMF dimethylformamide

DMSO dimethyl sulfoxide

THF tetrahydrofuran

HOBt 1-hydroxybenzotriazole

DCC N,N'-dicyclohexylcarbodiimide $^1$H NMR proton nuclear magnetic resonance spectra CI-MS chemical ionization mass spectrometry FAB-MS fast atom bombardment mass spectrometry El-MS electron ionization mass spectrometry

EXAMPLE 1

(2S)-1-(N-Benzyloxycarbonyl-L-prolyl)-2-[(Phenylthio)acetyl]-pyrrolidine (Compound 1)

A) (2S)-1-(t-Butoxycarbonyl)-2-(1,2-epoxyethyl)pyrrolidine

DMSO (20 ml) was added to sodium hydride (60% NaH, 1.55 g), and the mixture was stirred at 70° C. for 1 hour. The reaction mixture was cooled to room temperature and THF (20 ml) was added. The mixture was cooled to −5° C., and thereto was dropwise added trimethylsulfonium iodide (7.90 g) in DMSO (30 ml) over 3 minutes. After stirring for 1 minute, t-butoxycarbonyl-L-prolinal (5.13 g) in THF (15 ml) was added quickly, followed by stirring at room temperature for 1 hour. The reaction mixture was poured into ice water (300 ml) and extracted with chloroform. The organic layer was washed with saturated brine, dried over sodium sulfate and concentrated. The residue was purified by silica gel column chromatography (eluate: hexane-ethyl acetate) to give two kinds of diastereomers of (2S)- 1-(t-butoxycarbonyl)-2-(1,2-epoxyethyl)pyrrolidine, 3.12 g of its less polar compound and 1.28 g of its more polar compound. (Configuration of the epoxy moiety of the both unidentified.) The less polar compound was used in the following reactions.

B) (2S)-1-(t-Butoxycarbonyl)-2-[1-hydroxy-2-(phenylthio)-ethyl]pyrrolidine

To (2S)-1-(t-butoxycarbonyl)-2-(1,2-epoxyethyl)pyrrolidine (3.00 g) in methanol (100 ml) were added thiophenol (1.5 ml) and triethylamine (2.0 ml), followed by 2 hour' stirring under reflux. The reaction mixture was concentrated and the residue was purified by silica gel column chromatography (eluate: hexane-ethyl acetate) to give 4.14 g of (2S)- 1-(t-butoxycarbonyl)-2-[1-hydroxy-2-(phenylthio)ethyl]pyrrolidine.

C) (2S)-1-(N-Benzyloxycarbonyl-L-prolyl)-2-[1-hydroxy-2(phenylthio)ethyl]pyrrolidine 4N Hydrochloric acid/1,4-dioxane (57 ml) was added to (2S)-1-(t-butoxycarbonyl)-2-[1-hydroxy-2-(phenylthio)ethyl]pyrrolidine (4.90 g), and the mixture was stirred at room temperature for 1 hour. The reaction mixture was concentrated to dryness and the residue was dissolved in DMF (100 ml), to which were added known N-benzyloxycarbonyl-L-proline (3.79 g), N-methylmorpholine (1.54 g) and HOBt (3.08 g). The mixture was cooled to −25° C., then added with DCC (3.13 g), and stirred at a temperature between −25° C. and 0° C. for 3 hours and at room temperature for 16 hours. The resultant dicyclohexylurea was filtered off and the filtrate was concentrated. A solution of the residue in ethyl acetate was washed with a saturated aqueous solution of sodium bicarbonate and saturated brine successively, dries over magnesium sulfate, and cencentrated. The residue was purified by silica gel column chromatography (eluate : chloroform-methanol) to give 6.56 g of (2S)-1-(N-Benzyloxycarbonyl-L-prolyl)-2-[1-hydroxy- 2-(phenylthio) ethyl] pyrrolidine.

D) (2S)-1-(N-Benzyloxycarbonyl-L-prolyl)-2-[(phenylthio)-acetyl]pyrrolidine.

(2S)-1-(N-Benzyloxycarbonyl-L-prolyl)-2-[1-hydroxy-2-(phenylthio)ethyl]pyrrolidine (908 mg) was dissolved in DMSO (3 ml) and benzene (3 ml), and thereto were added pyridine (162 μl), trifluoroacetic acid (78 μl) and DCC (1.24 g) in order, and the mixture was stirred at room temperature for 1 hour. Ethyl acetate (50 ml) was added to the reaction mixture, and oxalic acid (540 mg) in methanol (5 ml) was added thereto, followed by stirring for 30 minutes. Water (50 ml) was added to the reaction mixture and the resultant dicyclohexylurea was filtered off. The filtrate was washed with 1N hydrochloric acid, a saturated aqueous solution of sodium bicarbonate and saturated brine in order, and dried over magnesium sulfate, followed by concentration. The residue was purified by silica gel column chromatography (eluate: chloroform-methanol) to give 714 mg of (2S)-1-(N-benzyloxycarbonyl-L-prolyl)-2-[(Phenylthio) acetyl]pyrrolidine (See Table 1).

EXAMPLE 2

(2S)-1-(N-Benzyloxycarbonyl-L-prolyl)-2-[(phenylsulfinyl)-acetyl]pyrrolidine (Compound 2)

A) (2S)-1-(N-Benzyloxycarbonyl-L-prolyl)-2-[1-hydroxy-2-(phenylsulfinyl)ethyl]pyrrolidine To (2S)-1-(N-benzyloxycarbonyl-L-prolyl)-2-[1-hydroxy-2-(phenylthio)ethyl]pyrrolidine (908 mg) as obtained in Example 1-C) in dichloromethane (30 ml) was added m-chloroperbenzoic acid (380 mg), followed by 2 hours' stirring under ice-cooling. The reaction mixture was diluted with chloroform, washed with ice-cooled 10% sodium sulfite, a saturated aqueous solution of sodium bicarbonate and saturated brine in order, and dried over magnesium sulfate, followed by concentration. The residue was purified by silica gel column chromatography (eluate: chloroform-methanol) to give 895 mg of (2S)- 1-(N-benzyloxycarbonyl-L-prolyl)-2-[1-hydroxy-2-(phenylsulfinyl)-ethyl]pyrrolidine.

B) (2S)-1-(N-Benzyloxycarbonyl-L-prolyl)-2-[(phenylsulfinyl)-acetyl]pyrrolidine (2S)-1-(N-Benzyloxycarbonyl-L-prolyl)-2-[1-hydroxy-2-(phenylsulfinyl)ethyl]pyrrolidine (850 mg) was subjected to DMSO-DCC oxidation as in Example 1-D) to give 672 mg of (2S)- 1-(N-benzyloxycarbonyl-L-prolyl)-2-[(phenylsulfinyl)acetyl]-pyrrolidine (See Table 1).

EXAMPLE 3

(2S)-1-(N-Benzyloxycarbonyl-L-prolyl)-2-[(phenylsulfonyl)-acetyl]pyrrolidine (Compound 3)
A) (2S)-1-(N-Benzyloxycarbonyl-L-prolyl)-2-[1-hydroxy-2(phenylsulfonyl)ethyl]pyrrolidine m-Chloroperbenzoic acid (440 mg) was added to (2S)-1-(N-benzyloxycarbonyl-L-prolyl)-2-[1-hydroxy-2-(phenylthio)-ethyl]pyrrolidine (516 mg) as obtained in Example 1-C) in dichloromethane (30 ml ), followed by stirring at room temperature for 3 hours. The reaction mixture was treated and purified in the same manner as in Example 2-A) to give 540 mg of (2S)-1-(N-benzyloxycarbonyl-L-prolyl)-2-[1-hydroxy-2-(phenylsulfonyl)ethyl]pyrrolidine.
B) (2S)-1-(N-Benzyloxycarbonyl-L-prolyl)-2-[(phenylsulfonyl)-acetyl]pyrrolidine (2S)-1-(N-Benzyloxycarbonyl-L-prolyl)-2-[1-hydroxy-2-(phenylsulfonyl)ethyl]pyrrolidine (500 mg) was subjected to DMSO-DCC oxidation as in Example 1-D) to give 412 mg of (2S)- 1-(N-benzyloxycarbonyl-L-prolyl)-2-[(phenylsulfonyl)acetyl]-pyrrolidine (See Table 1).

EXAMPLE 4

(2S)-1-(N-Benzyloxycarbonyl-L-prolyl)-2-(phenoxyacetyl)-pyrrolidine (Compound 4)
A) (2S)-1-(t-Butoxycarbonyl)-2-(1-hydroxy-2-phenoxyethyl)-pyrrolidine Phenol (1.50 g) and sodium methoxide (380 mg) were added to (2S)-1-(t-butoxycarbonyl)-2-(1,2-epoxyethyl)pyrrolidine (1.50 g) as obtained in Example 1-A) in methanol (30 ml ), followed by 16 hour' stirring under reflux. The reaction mixture was concentrated and the residue was dissolved in ether. The solution was washed with 1N hydrochloric acid, a saturated aqueous solution of sodium bicarbonate and saturated brine in order, and dried over magnesium sulfate, followed by concentration. The residue was purified by silica gel column chromatography (eluate: hexane-ethyl actate) to give 1.10 g of (2S)-1-(t-butoxycarbonyl)-2-(1-hydroxy-2-phenoxyethyl)-pyrrolidine.
B) (2S)-1-(N-Benzyloxycarbonyl-L-prolyl)-2-(1-hydroxy-2-phenoxyethyl)pyrrolidine 4N Hydrochloric acid/1,4-dioxane (16 ml) was added to (2S)-1-(t-butoxycarbonyl)-2-(1-hydroxy-2-phenoxyethyl)pyrrolidine (1.10 g), and the mixture was stirred at room temperature for 1 hour. The reaction mixture was concentrated to dryness and the residue was dissolved in DMF (10 ml), to which were added known N-benzyloxycarbonyl-L-proline (850 mg), N-methylmorpholine (0.38 ml) and HOBt (0.68 g). The reaction mixture was cooled to −25° C., added with DCC (0.72 g), and stirred at a temperature between −25° C. and 0° C. for 3 hours and then at room temperature for 12 hours. The resultant dicyclohexylurea was filtered off and the filtrate was concentrated. The residue was dissolved in ethyl acetate, washed with a saturated aqueous solution of sodium bicarbonate and saturated brine in order, and dried over magnesium sulfate, followed by concentration. The residue was purified by silica gel column chromatography (eluate: chloroform-methanol) to give 340 mg of (2S)-1-(N-benzyloxycarbonyl-L-prolyl)-2-(1-hydroxy-2-phenoxyethyl)-pyrrolidine.

C) (2S)-1-(N-Benzyloxycarbonyl-L-prolyl)-2-(phenoxyacetyl)-pyrrolidine (2S)-1-(N-Benzyloxycarbonyl-L-prolyl)-2-(1-hydroxy-2-phenoxyethyl)pyrrolidine (393 mg) was subjected to DMSO-DCC oxidation in the same manner as in Example 1-D) to give 328 mg of (2S)-1-(N-benzyloxycarbonyl-L-prolyl)-2-(phenoxyacetyl)-pyrrolidine (See Table 2).

EXAMPLE 5

(2S)-1-[N-(4-Phenylbutyryl)-L-prolyl]-2-[(phenylsulfinyl)-acetyl]pyrrolidine (Compound 5)
A) N-(4-Phenylbutyryl)-L-proline benzyl ester N-Methylmorpholine (3.4 ml) and 4-phenylbutyric acid (5.02 g) were added to L-proline benzyl ester hydrochloride (7.37 g) in dichloromethane (80 ml) under ice-cooling. The mixture was cooled to −25° C., added with DCC (6.31 g) and stirred at room temperature for 16 hours. The resultant dicyclohexylurea was filtered off and the filtrate was concentrated. The residue was purified by silica gel column chromatography (eluate: chloroform-methanol) to give 9.42 g of N-(4-phenylbutyryl)-L-proline benzyl ester.
B) N-(4-phenylbutyryl)-L-proline To N-(4-phenylbutyryl)-L-proline benzyl ester (9.31 g) in 99% methanol (100 ml) was added 10% Pd—C (0.90 g), and the mixture was stirred at room temperature in hydrogen stream for 2 hours. The catalyst was filtered off with celite, and the filtrate was concentrated to give 6.26 g of N-(4-phenylbutyryl)-L-proline.
C) (2S)-2-[1-Hydroxy-2-(phenylthio)ethyl]-1-[N-(4-phenyl-butyryl)-L-prolyl]pyrrolidine 4N Hydrochloric acid/1,4-dioxane (23 ml) was added to (2S)-1-(t-butoxycarbonyl)-2-[1-hydroxy-2-(phenylthio)ethyl]pyrrolidine e (3.05 g) as obtained in Example 1-B), and the mixture was stirred at room temperature for 0.5 hour. The reaction mixture was concentrated to dryness, and the residue was dissolved in DMF (18 ml), to which N-(4-phenylbutyryl)-L-proline (2.65 g), N-methylmorpholine (1.2 ml) and HOBt (1.88 g) were added. The mixture was cooled to −25° C., added with DOG (1.95 g) and stirred at a temperature between −25° C. and 0° C. for 2 hours and then at room temperature for 14 hours. The reaction mixture was treated and purified in the same manner as in Example 1-C) to give 2.45 g of (2S)-2-[1-hydroxy-2-(phenylthio)ethyl]- 1-[N-(4-phenylbutyryl)-L-prolyl]pyrrolidine.
D) (2S)-2-[1-Hydroxy-2-(phenylsulfinyl)ethyl]- 1-[N-(4-phenylbutyryl)-L-prolyl]pyrrolidine (2S)-2-[1-Hydroxy-2-(phenylthio)ethyl]-1-[N-(4-phenylbutyryl)-L-prolyl]pyrrolidine (1.25 g) was subjected to oxidation in the same manner as in Example 2-A) in dichloromethane (9 ml) using 1.1 equivalent of m-chloroperbenzoic acid to give 1.18 g of (2S)-2-[1-hydroxy- 2-(phenylsulfinyl)ethyl]-1-[N-(4-phenylbutyryl)-L-prolyl]-pyrrolidine.
E) (2S)-1-[N-(4-Phenylbutyryl)-L-prolyl]-2-[(phenylsulfinyl)-acetyl]pyrrolidine (2S)-2-[1-Hydroxy-2-(phenylsulfinyl)ethyl]-1-[N-(4-phenylbutyryl)-L-prolyl]pyrrolidine (1.07 g) was subjected to DMSO-DCC oxidation as in Example 1-D) to give 0.89 g of (2S)- 1-[N-(4-phenylbutyryl)-L-prolyl]-2-[(phenylsulfinyl)acetyl]-pyrrolidine (See Table 2).

EXAMPLE 6

(2S)-1-(N-Benzyloxycarbonyl-L-prolyl)-2-[(4-methoxyphenylsulfinyl)acetyl]pyrrolidine (Compound 6)
A) (2S)-1-(t-Butoxycarbonyl)-2-[1-hydroxy-2-(4-methoxyphenylthio)ethyl]pyrrolidine 4-Methoxythiophenol (1.0 ml) and triethylamine (1.0 ml) were added to (2S)-1-(t-butoxycarbonyl)-2-(1,2-epoxyethyl)-pyrrolidine (1.57 g) as obtained in Example 1-A) in methanol (50 ml), and the mixture was stirred for 1.5 hours under reflux. The reaction mixture was concentrated and the residue was poured into ice-water, followed by extraction with ethyl acetate. The extract was washed with saturated brine, dried over magnesium sulfate and concentrated. The residue was recrystallized from a mixted solution of hexane-ethyl acetate to give 2.16 g of the title compound as colorless needles.

B) (2S)-1-(N-Benzyloxycarbonyl-L-prolyl)-2-[1-hydroxy-2-(4-methoxyphenylthio)ethyl]pyrrolidine 4N Hydrochloric acid/1,4-dioxane (15 ml) was added to (2S)-1-(t-butoxycarbonyl)-2-[1-hydroxy-2-(4-methoxyphenylthio)ethyl]-pyrrolidine (2.02 g), and the mixture was stirred at room temperature for 0.5 hour. The reaction mixture was concentrated to dryness, and the residue was dissolved in DMF (15 ml), followed by condensation reaction as in Example 1-C) with known N-benzyloxycarbonyl-L-proline (1.42 g) to give 2.51 g of the title compound.

C) (2S)-1-(N-Benzyloxycarbonyl-L-prolyl)-2-[1-hydroxy-2-(4methoxyphenylsulfinyl)ethyl]pyrrolidine (2S)-1-(N-Benzyloxycarbonyl-L-prolyl)-2-[1-hydroxy-2-(4-methoxyphenylthio)ethyl]pyrrolidine (1.51 g) was subjected to oxidation as in Example 2-A) in dichloromethane using 1.1 equivalent of m-chloroperbenzoic acid to give 984 mg of the title compound.

D) (2S)-1-(N-Benzyloxycarbonyl-L-prolyl)-2-[(4-methoxyphenylsulfinyl)acetyl]pyrrolidine (2S)-1-(N-Benzyloxycarbonyl-L-prolyl)-2-[1-hydroxy-2-(4methoxyphenylsulfinyl)ethyl]pyrrolidine (901 mg) was subjected to DMSO-DCC oxidation as in Example 1-D) to give 652 mg of the title compound (See Table 2).

EXAMPLE 7

(2S)-1-(N-Benzyloxycarbonyl-L-prolyl)-2-[(4-nitrophenylsulfinyl)acetyl]pyrrolidine (Compound 7)

A) (2S)-1-(t-Butoxycarbonyl)-2-[1-hydroxy-2-(4-nitrophenylthio)-ethyl]pyrrolidine 4-Nitrothiophenol (1.21 g) and triethylamine (0.91 ml) were added to (2S)-1-(t-butoxycarbonyl)-2-(1,2-epoxyethyl)-pyrrolidine (1.39 g) as obtained in Example 1-A) in methanol (50 ml), and the mixture was stirred for 2 hours under reflux. The reaction mixture was concentrated and the residue was purified by silica gel column chromatography (eluate : hexane-ethyl acetate) to give 1.85 g of the title compound. B) (2S)-1-(N-Benzyloxycarbonyl-L-prolyl)-2-[1-hydroxy-2-(4-nitrophenylthio)ethyl]pyrrolidine 4N Hydrochloric acid/1,4-dioxane (20 ml) was added to (2S)1-(t-butoxycarbonyl)-2-[1-hydroxy-2-(4-nitrophenylthio)-ethyl]pyrrolidine (1.64 g), and the mixture was stirred at room temperature for 0.5 hour. The reaction mixture was concentrated to dryness, and the residue was dissolved in DMF (12 ml), followed by condensation reaction as in Example 1-C) with known N-benzyloxycarbonyl-L-proline (1.10 g) to give 2.03 g of the title compound.

C) (2S)-1-(N-Benzyloxycarbonyl-L-prolyl)-2-[1-hydroxy-2-(4-nitrophenylsulfinyl)ethyl]pyrrolidine (2S)-1-(N-Benzyloxycarbonyl-L-prolyl)-2-[1-hydroxy-2-(4-nitrophenylthio)ethyl]pyrrolidine (1.50 g) was subjected to oxidation as in Example 2-A) in dichloromethane using 1.1 equivalent of m-chloroperbenzoic acid to give 894 mg of the title compound.

D) (2S)-1-(N-Benzyloxycarbonyl-L-prolyl)-2-[(4-nitrophenylsulfinyl)acetyl]pyrrolidine (2S)-1-(N-Benzyloxycarbonyl-L-prolyl)-2-[1-hydroxy-2-(4-nitrophenylsulfinyl)ethyl]pyrrolidine (883 mg) was subjected to DMSO-DCC oxidation as in Example 1-D) to give 673 mg of the title compound (See Table 3).

EXAMPLE 8

(2S)-1-(N-Benzyloxycarbonyl-L-prolyl)-2-[(isopropylsulfinyl)-acetyl]pyrrolidine (Compound 8)
A) (2S)-1-(t-Butoxycarbonyl)-2-[1-hydroxy-2-(isopropylthio)-ethyl]pyrrolidine Isopropylmercaptan (0.93 ml) and triethylamine (1.39 ml) were added to (2S)-1-(t-butoxycarbonyl)-2-(1,2-epoxyethyl)-pyrrolidine (2.11 g) as obtained in Example 1-A) in methanol (100 ml), and the mixture was stirred for 2 hours under reflux. The reaction mixture was concentrated and the residue was purified by silica gel column chromatography (eluate: hexane-ethyl acetate) to give 1.66 g of the title compound.

B) (2S)-1-(N-Benzyloxycarbonyl-L-prolyl)-2-[1-hydroxy-2(isopropylthio)ethyl]pyrrolidine 4N Hydrochloric acid/1,4-dioxane (25 ml) was added to (2S)1-(t-butoxycarbonyl)-2-[1-hydroxy-2-(isopropylthio)ethyl]-pyrrolidine (1.68 g), and the mixture was stirred at room temperature for 0.5 hour. The reaction mixture was concentrated to dryness, and the residue was dissolved in DMF (12 ml), followed by the condensation reaction as in Example 1-C) with known N-benzyloxycarbonyl-L-proline (1.46 g) to give 2.08 g of the title compound.

C) (2S)-1-(N-Benzyloxycarbonyl-L-prolyl)-2-[1-hydroxy-2-(isopropylsulfinyl)ethyl]pyrrolidine (2S)-1-(N-Benzyloxycarbonyl-L-prolyl)-2-[1-hydroxy-2-(isopropylthio)ethyl]pyrrolidine (1.61 g) was subjected to oxidation as in Example 2-A) in dichloromethane using 1.1 equivalent of m-chloroperbenzoic acid to give 1.40 g of title compound.

D) (2S)-1-(N-Benzyloxycarbonyl-L-prolyl)-2-[(isopropylsulfinyl)-acetyl]pyrrolidine (2S)-1-(N-Benzyloxycarbonyl-L-prolyl)-2-[1-hydroxy-2(isopropylsulfinyl)ethyl]pyrrolidine (1.34 g) was subjected to DMSO-DCC oxidation as in Example 1-D) to give 502 mg of the title compound (See Table 3).

EXAMPLE 9

(2S)-1-(N-Benzyloxycarbonyl-L-prolyl)-2-{[(S)-phenylsulfinyl]-acetyl}pyrrolidine (Compound 9)
A) (2S)-1-(N-Benzyloxycarbonyl-L-prolyl)-2-{1-hydroxy-2-[(S)-phenylsulfinyl]ethyl}pyrrolidine (2S)-1-(N-Benzyloxycarbonyl-L-prolyl)-2-[1-hydroxy-2(phenylsulfinyl)ethyl]pyrrolidine (6.72 g) as obtained in Example 2-A) was again purified by medium pressure liquid chromatography (silica gel, eluate; chloroform:methanol =98:2) to give the title compound (2.51 g), the corresponding (R)-phenyl-sulfinyl compound (2.20 g) and a mixture of the two (1.87 g).
B) (2S)-1-(N-Benzyloxycarbonyl-L-prolyl)-2-{[(S)-phenylsulfinyl]acetyl}pyrrolidine (2S)-1-(N-Benzyloxycarbonyl-L-prolyl)-2-{1-hydroxy-2-[(S)-phenylsulfinyl]ethyl}pyrrolidine (600 mg) was subjected to DMSO-DCC oxidation as in Example 1-D), followed by purification of the reaction product by medium pressure silica gel column chromatography (eluate; chloroform:methanol=99.5: 0.5) to give 242 mg of the title compound (See Table 3 ).

Example 10

(2S)-1-(N-Benzyloxycarbonyl-L-prolyl)-2-{[(R)-phenylsulfinyl]acetyl}pyrrolidine (Compound 10)

27

(2S)-1-(N-Benzyloxycarbonyl-L-prolyl)-2-{1-hydroxy-2-[(R)-phenylsulfinyl]ethyl}pyrrolidine (1.00 g) as obtained in Example 9-A) was subjected to DMSO-DCC oxidation as in Example 1-D), followed by purification of the reaction product by medium pressure liquid chromatography (silica gel, eluate; chloroform:methanol=99.5:0.5). The oily substance (500 mg) was recrystallized from acetone-ether-hexane to give 300 mg of the title compound as colorless needles (See Table 4).

EXAMPLE 11

(2S)-1-(N-Benzyloxycarbonyl-L-prolyl)-2-{[(S)-4-methoxy-phenylsulfinyl]acetyl}pyrrolidine (Compound 11)
A) (2S)-1-(N-Benzyloxycarbonyl-L-prolyl)-2-{1-hydroxy-2-[(S)-4-methoxyphenylsulfinyl]ethyl}pyrrolidine (2S)-1-(N-Benzyloxycarbonyl-L-prolyl)-2-[1-hydroxy-2-(4methoxyphenylsulfinyl)ethyl]pyrrolidine (575 mg) as obtained in Example 6-C) was again purified by medium pressure liquid chromatography (silica gel, eluate; chloroform:methanol= 98.5:1.5) to give the title compound (164 mg), the corresponding (R)-4-methoxyphenylsulfinyl compound (221 mg) and a mixture of the two (175 mg).
B) (2S)-1-(N-Benzyloxycarbonyl-L-prolyl)-2-{[(S)-4-methoxyphenylsulfinyl]acetyl}pyrrolidine (2S)-1-(N-Benzyloxycarbonyl-L-prolyl)-2-{1-hydroxy-2-[(S)- 4-methoxyphenylsulfinyl]ethyl}pyrrolidine (152 mg) was subjected to DMSO-DCC oxidation as in Example 1-D), and the reaction product was purified by silica gel preparative thin-layer chromatography (developing solvent; chloroform:methanol =98:2, double development) to give 97 mg of the title compound (See Table 4).

EXAMPLE 12

(2S)-1-(N-Benzyloxycarbonyl-L-prolyl)-2-{[(R)-4-methoxy-phenylsulfinyl]acetyl}pyrrolidine (Compound 12)

(2S)-1-(N-Benzyloxycarbonyl-L-prolyl)-2-{1-hydroxy-2-[(R)-4-methoxyphenylsulfinyl]ethyl}pyrrolidine (182 mg) as obtained in Example 11-A) was subjected to DMSO-DCC oxidation as in Example 1-D), and the reaction product was purified by silica gel preparative thin-layer chromatography (developing solvent; chloroform:methanol=99:1, triple development) to give 134 mg of the title compound (See Table 4).

EXAMPLE 13

(2S)-1-(N-Benzyloxycarbonyl-L-prolyl)-2-{[(S)-p-tolylsulfinyl]acetyl}pyrrolidine (Compound 13)
A) (2S)-1-(N-Benzyloxycarbonyl-L-prolyl)-2-{1-hydroxy-2-[(S)-p-tolylsulfinyl]ethyl}pyrrolidine To diisopropylamine (0.26 ml) in THF (6 ml) was dropwise added 1.62M n-butyllithium-hexane solution (1.12 ml) at −78° C., and the mixture was stirred at 0° C. for 0.5 hour. The reaction mixture was cooled to −30° C., dropwise added with (S)–(−)-methyl p-tolyl sulfoxide (255 mg) in THF (6 ml), and stirred at 0° C. for 0.5 hour. The reaction mixture was cooled to −78° C. and dropwise added with known N-benzyloxycarbonyl-L-prolyl-L-prolinal (300 mg) in THF (6 ml). After stirring for 0.5 hour, an aqueous solution of saturated ammonium chloride was added thereto, followed by stirring at room temperature for 10 minutes. The reaction mixture was extracted with ethyl acetate, and the organic layer was washed with a saturated aqueous solution of sodium bicarbonate and saturated brine order, dried over magnesium sulfate and concentrated. The residue was purified by silica gel column chromatography (eluate; chloroform-methanol) to give 388 mg of the title compound.
B) (2S)-1-(N-Benzyloxycarbonyl-L-prolyl)-2-{[(S)-p-tolylsulfinyl]acetyl}pyrrolidine (2S)-1-(N-Benzyloxycarbonyl-L-prolyl)-2-{1-hydroxy-2-[(S)-p-tolylsulfinyl]ethyl}pyrrolidine (357 mg) was subjected to DMSO-DCC oxidation as in Example 1-D), and the reaction product was purified by medium pressure liquid chromatography (silica gel, eluate; chloroform:methanol= 99:1) to give 162 mg of the title compound (See Table 4).

EXAMPLE 14

(2S)-1-(N-Benzyloxycarbonyl-L-prolyl)-2-{[(R)-p-tolylsulfinyl]acetyl)}pyrrolidine (Example 14)

By the same procedure as in Example 13 using (R)-(+)-methyl p-tolyl sulfoxide 43 mg) in place of (S)-(−)-methyl p-tolyl sulfoxide, 32 mg of the title compound was obtained (See Table 5).

EXAMPLE 15

(2S)-2-{[(S)-4-Methoxyphenylsulfinyl]acetyl)}- 1-[N-(3-phenylpropionyl)-L-prolyl]pyrrolidine (Compound 15)
A) N-(3-phenylpropionyl)-L-proline By the same procedure as in Example 5-A) and B) using 3-phenylpropionic acid (13.67 g) in place of 4-phenylbutyric acid, 17.36 g of the title compound was obtained.
B) N-(3-Phenylpropionyl)-L-prolyl-L-proline benzyl ester To L-proline benzyl ester hydrochloride (0.98 g) in dichloromethane (20 ml) were added N-methylmorpholine (0.49 ml), N-(3-phenylpropionyl)-L-proline (1.00 g) and HOBt (0.60 g) under ice-cooling. After cooling to −25° C. , DCC (0.92 g) was added, and the mixture was stirred at a temperature between −25° C. and 0° C. for 2 hours, and then at room temperature for 14 hours. The reaction mixture was treated and purified as in Example 7-A) to give 1.39 g of the title compound.
C) (S)-(−)-4-Methoxyphenyl methyl sulfoxide To titanium tetraisopropoxide (1.49 ml) in dichloromethane (50 ml) were added diethyl (S,S)-tartrate (1.71 ml) and water (90 µl), and the mixture was stirred at room temperature for 20 minutes. After 1-methoxy-4-(methylthio)benzene (0.69 ml) was dropwise added, the reaction mixture was cooled to −20° C., dropwise added with 3.07M t-butylhydroperoxide-toluene solution (1.8 ml), and stirred at −20° C. for 15 hours. Water (0.9 ml) was added, and the mixture was stirred at −20° C. for 1 hour, and then at room temperature for 1 hour. A small amount of alumina was added, and the reaction mixture was suction-filtered with celite and washed well with dichloromethane. The filtrate and the washing were combined, added with 5% sodium hydroxide-saturated brine and stirred at room temperature for 1 hour. The organic layer was separated, dried over magnesium sulfate and concentrated. The residue was purified by silica gel column chromatography (eluate; ethyl acetate), and the residue (730 mg) was recrystallized from ether-pentane to give 586 mg of the title compound, $[\alpha]_D$ −103° C. (c=1.98, acetone).
D) (2S)-2-{[(S)-4-methoxyphenylsulfinyl]acetyl}-1-[N-(3-phenylpropionyl)-L-prolyl]pyrrolidine To diisopropylamine (0.13 ml) in THF (8 ml) was dropwise added 1.62M n-butyllithium-hexane solution (1.2 ml) at −78° C., followed by stirring at 0° C. for 0.5 hour. The reaction mixture was cooled to −30° C., dropwise added with (S)-(−)- 4methoxyphenyl methyl sulfoxide (157 mg) in THF (8 ml), and stirred at 0° C. for 0.5 hour. The reaction mixture was cooled to −78° C., added with N-(3-phenylpropionyl)-L-prolyl-L-proline benzyl ester (400 mg) in THF (8 ml) quickly, and stirred for 0.5 hour. The reaction mixture was treated as in Example 13-A) and the residue obtained was purified by medium pressure liquid chromatography (silica gel, eluate; chloroform:methanol=99:1) to give 195 mg of the title compound (See Table 5).

EXAMPLE 16

(2S)-1-[N-(3-Phenylpropionyl)-L-prolyl]-2-{[(S)-p-tolylsulfinyl]acetyl}pyrrolidine (Compound 16)

The oily substance (231 mg) obtained by the same procedure as in Example 15-D) using (S)-(−)-methyl p-tolyl sulfoxide (142 mg) in place of (S)-(−)-4-methoxyphenyl methyl sulfoxide was recrystallized from hexane-ethyl acetate to give 160 mg of the title compound as colorless needles (See Table 5).

EXAMPLE 17

(2S)-1-[N-(3-Phenylpropionyl)-L-prolyl]-2-{[(S)-phenylsulfinyl]acetyl}pyrrolidine (Compound 17)
A) (S)-(−)-methyl phenyl sulfoxide By the same procedure as in Example 15-C) using thioanisole (5.87 ml) in place of 1-methoxy-4-(methylthio)-benzene, 4.63 g of the title compound was obtained, $[\alpha]_D$ −125° (c=1.81, acetone).

B) (2S)-1-[N-(3-phenylpropionyl)-L-prolyl]-2-{[(S)-phenylsulfinyl]acetyl}pyrrolidine The crystalline substance (202 mg) as obtained by the same procedure as in Example 15-D) using (S)-(−)-methyl phenyl sulfoxide (129 mg) in place of (S)-(−)-4-methoxyphenyl methyl sulfoxide was recrystallized from hexane-ethyl acetate to give 155 mg of the title compound as colorless needles (See Table 5).

EXAMPLE 18

(2S)-1-(N-Benzyloxycarbonyl-L-prolyl)-2-[(4-methoxyphenoxy)-acetyl]pyrrolidine (Compound 18)
A) (2S)-1-[t-Butoxycarbonyl)-2-[1-hydroxy-2-(4-methoxyphenoxy)-ethyl]pyrrolidine To (2S)-1-[t-butoxycarbonyl)-2-(1,2-epoxyethyl)pyrrolidine (11.70 g) as obtained in Example 1-A) in methanol (50 ml) were added 4-methoxyphenol (13.60 g) and 1M sodium methoxide-methanol solution (54.9 ml), and the mixture was stirred at 70° C. for 18 hours. The reaction mixture was poured into a satuated aqueous solution of ammonium chloride and extracted with ethyl acetate. The extract was washed with saturated brine, dried over magnesium sulfate and concentrated. The residue was purified by silica gel column chromatography (eluate; hexane-ethyl acetate) to give 14.20 g of the title compound.

B) (2S)-1-(N-Benzyloxycarbonyl-L-prolyl)-2-[1-hydroxy-2-(4-methoxyphenoxy)ethyl]pyrrolidine To (2S)-1-[t-butoxycarbonyl)-2-[1-hydroxy-2-(4-methoxyphenoxy)ethyl]pyrrolidine (14.03 g) was added 4N hydrochloric acid/1,4-dioxane (220 ml), and the mixture was stirred at room temperature for 1 hour. The reaction mixture was concentrated to dryness, and the residue was dissolved in DMF (100 ml), followed by condensation reaction as in Example 1-C) with known N-benzyloxycarbonyl-L-proline (10.70 g) to give 11.10 g of the title compound.

C) (2S)-1-(N-Benzyloxycarbonyl-L-prolyl)-2-[(4-methoxyphenoxy)-acetyl]pyrrolidine (2S)-1-(N-Benzyloxycarbonyl-L-prolyl)-2-[1-hydroxy-2-(4-methoxyphenoxy)ethyl]pyrrolidine (10.94 g) was subjected to DMSO-DCC oxidation in the same manner as in Example 1, D) to give 10.78 g of the title compound (See Table 6).

EXAMPLE 19

(2S)-2-(Phenoxyacetyl)-1-[N-(3-phenylpropionyl)-L-prolyl]-pyrrolidine (Compound 19)
A) (2S)-2-(1-hydroxy-2-phenoxyethyl)-1-[N-(3-phenylpropionyl)-L-prolyl]pyrrolidine (2S)-1-(t-Butoxycarbonyl)-2-(1-hydroxy-2-phenoxyethyl)-pyrrolidine (1.20 g) as obtained in Example 4-A) was dissolved in 4N hydrochloric acid/1,4-dioxane (20 ml), and the mixture was stirred at room temperature for 0.5 hour. The reaction mixture was concentrated to dryness, and the residue was dissolved in DMF (9 ml), followed by condensation reaction as in Example 1-C) with N-(3-phenylpropionyl)-L-proline (0.96 g) as obtained in Example 15-A) to give 461 mg of the title compound.

B) (2S)-2-(phenoxyacetyl)-1-[N-(3-phenylpropionyl)-L-prolyl]pyrrolidine (2S)-2-(1-Hydroxy-2-phenoxyethyl)- 1-[N-(3-phenylpropionyl)-L-prolyl]pyrrolidine (425 mg) was subjected to DMSO-DCC oxidation as in Example 1D) to give 152 mg of the title compound (See Table 6).

EXAMPLE 20

(2S)-2-[(4-Methoxyphenoxy)acetyl]-1-[N-(3-phenylpropionyl)-L-prolyl]pyrrolidine (Compound 20)
A) (2S)-2-[1-Hydroxy-2-(4-methoxyphenoxy)ethyl]- 1-[N-(3-phenylpropionyl)-L-prolyl]pyrrolidine (2S)-1-(t-Butoxycarbonyl)-2-[1-hydroxy-2-(4-methoxyphenoxy)ethyl]pyrrolidine (455 mg) as obtained in Example 18-A) was dissolved in 4N hydrochloric acid/1,4-dioxane (7 ml), and the mixture was stirred at room temperature for 0.5 hour. The reaction mixture was concentrated to dryness, and the residue was dissolved in DMF (7 ml), followed by condensation reaction as in Example 1-C) with N-(3-phenylpropionyl)-L-proline (335 mg) as obtained in Example 15-A) to give 138 mg of the title compound.

B) (2S)-2-[(4-Methoxyphenoxy)acetyl]-1-[N-(3-phenylpropionyl)-L-prolyl]pyrrolidine (2S)-2-[1-Hydroxy-2-(4-methoxyphenoxy)ethyl]- 1-[N-(3-phenylpropionyl)-L-prolyl]pyrrolidine (128 mg) was subjected to DMSO-DCC oxidation as in Example 1-D) to give 45 mg of the title compound (See Table 6).

EXAMPLE 21

(2S)-1-(N-Benzylaminocarbonyl-L-prolyl)-2-(phenoxyacetyl)-pyrrolidine (Compound 21)
A) (2S)-1-[N-(t-Butoxycarbonyl)-L-prolyl]-2-(1-hydroxy-2-phenoxyethyl)pyrrolidine (2S)-1-(t-Butoxycarbonyl)-2-(1-hydroxy-2-phenoxyethyl)-pyrrolidine (1.93) as obtained in Example 4-A) was dissolved in 4N hydrochloric acid/1,4-dioxane (31 ml), and the mixture was stirred at room temperature for 0.5 hour. The reaction mixture was concentrated to dryness, and the residue was dissolved in DMF 15 ml), followed by condensation reaction as in Example 1-C) with N-(t-butoxycarbonyl)-L-proline (1.36 g), N-methylmorpholine 0.69 ml), HOBt (1.02 g) and DCC (1.30 g) to give 2.10 g of the title compound.

B) (2S)-1-(N-Benzylaminocarbonyl-L-prolyl)-2-(1-hydroxy-2-phenoxyethyl)pyrrolidine (2S)-1-[N-(t-Butoxycarbonyl)-L-prolyl]-2-(1-hydroxy-2-phenoxyethyl)pyrrolidine (0.99 g) was dissolved in 4N hydrochloric acid/1,4-dioxane (13 ml), and the mixture was stirred at room temperature for 0.5 hour. The reaction mixture was concentrated to dryness, and the residue was dissolved in dichloromethane (10 ml), to which N-methylmorpholine (0.27 ml) and benzylisocyanate (0.30 ml) were dropwise added in order under ice-cooling. After stirring for 1.5 hours, the reaction mixture was poured into ice-water and extracted with dichloromethane. The organic layer was washed with 1N hydrochloric acid, a saturated aqueous solution of sodium bicarbonate and saturated brine in order, dried over anhydrous magnesium sulfate, and concentrated. The residue was recrystallized from ethyl acetate-hexane to give 0.85 g of the title compound.

C) (2S)-1-(N-Benzylaminocarbonyl-L-prolyl)-2-(phenoxyacetyl)-pyrrolidine (2S)-1-(N-Benzylaminocarbonyl-L-prolyl)-2-(1-hydroxy-2-phenoxyethyl)pyrrolidine (798 mg) was subjected to DMSO-DCC oxidation as in Example 1D), followed by recrystallization from ethyl acetate-hexane to give 427 mg of the title compound (See Table 6).

EXAMPLE 22

(2S)-1-(N-Benzylaminocarbonyl-L-prolyl)-2-(4-methoxyphenoxyacetyl)pyrrolidine (Compound 22)

A) (2S)-1-[N-(t-Butoxycarbonyl)-L-prolyl]-2-[1-hydroxy-2-(4methoxyphenoxy)ethyl]pyrrolidine (2S)-1-(t-Butoxycarbonyl)-2-[1-hydroxy-2-(4-methoxyphenoxy)ethyl]pyrrolidine (1.57 g) as obtained in Example 18-A) was dissolved in 4N hydrochloric acid/1,4-dioxane (23 ml), and the mixture was stirred at room temperature for 1 hour. The reaction mixture was concentrated to dryness, and the residue was dissolved in DMF (15 ml), followed by condensation reaction as in Example 1-C) with N-(t-butoxycarbonyl)-L-proline (1.00 g), N-methylmorpholine (0.51 ml), HOBt (0.75 g) and DCC (0.96 g) to give 1.41 g of the title compound.

B) (2S)-1-(N-Benzylaminocarbonyl-L-prolyl)-2-[1-hydroxy-2-(4-methoxyphenoxy)ethyl]pyrrolidine By the same procedure as in Example 21-B), (2S)-1-[N-(t-butoxycarbonyl)-L-prolyl]-2-[ 1-hydroxy-2-(4-methoxyphenoxy) ethyl]pyrrolidine (722 mg) was treated with 4N hydrochloric acid/1,4-dioxane, followed by reaction with benzylisocyanate (0.21 ml) to give 596 mg of the title compound as crystals. C) (2S)-1-(N-Benzylaminocarbonyl-L-prolyl)-2-(4-methoxyphenoxyacetyl)pyrrolidine (2S)-1-(N-Benzylaminocarbonyl-L-prolyl)-2-[1-hydroxy-2-(4methoxyphenoxy)ethyl]pyrrolidine (557 mg) was dissolved in a mixed solution of DMSO (3 ml), benzene (1.5 ml) and triethylamine (0.6 ml) and added with sulfur trioxide-pyridine complex (0.52 g) under ice-cooling. After stirring at 5°–10° C. for 1 hour, the reaction mixture was poured into ice-water and extracted with ethyl acetate. The organic layer was washed with 1N hydrochloric acid, a saturated aqueous solution of sodium bicarbonate and saturated brine in order, dried over anhydrous magnesium sulfate and concentrated. The residue was recrystallized from a mixture of ethyl acetate-hexane to give 374 mg of the title compound (See Table 7).

EXAMPLE 23

(2S)-1-(N-Benzylaminocarbonyl-L-prolyl)-2-{[(S)-4-methoxyphenylsulfinyl]acetyl}pyrrolidine (Compound 23)
A) N-(t-Butoxycarbonyl)-L-prolyl-L-proline benzyl ester To a suspension of L-proline benzyl ester hydrochloride (3.37 g) in dichloromethane (60 ml) were added N-methylmorpholine (1.54 ml), N-(t-butoxycarbonyl)-L-proline (3.00 g), HOBt (2.08 g) and water-soluble carbodiimide hydrochloride (2.95 g) in order, followed by stirring for 1 hour. After stirring at room temperature for 17 hours, the reaction mixture was poured into ethyl acetate, washed with 1N hydrochloric acid, a saturated aqueous solution of sodium bicarbonate and saturated brine in order, dried over anhydrous magnesium sulfate, and concentrated. The residue was purified by silica gel column chromatography (eluate; hexane-ethyl acetate) to give 5.00 g of the title compound.

B) N-Benzylaminocarbonyl-L-prolyl-L-proline benzyl ester

N-(t-Butoxycarbonyl)-L-prolyl-L-proline benzyl ester (3.60 g) was treated with 4N hydrochloric acid/1,4-dioxane and then reacted with benzylisocyanate (1.2 ml) as in Example 21-B) to give 2.98 g of the title compound as crystals.

C) (2S)-1-(N-Benzylaminocarbonyl-L-prolyl)-2-{[(S)-4-methoxyphenylsulfinyl]acetyl}pyrrolidine By the same procedure as in Example 15-D) using N-benzylaminocarbonyl-L-prolyl-L-proline benzyl ester (2.00 g) and (S)-(−)-4-methoxyphenyl methyl sulfoxide (780 mg) as obtained in Example 15-C), there was obtained 629 mg of the title compound as colorless needles (See Table 7).

EXAMPLE 24

(2S)-1-[N-(4-Methoxybenzylaminocarbonyl)-L-prolyl]-2-{[(S)- 4-methoxyphenylsulfinyl]acetyl}pyrrolidine (Compound 24)

A) N-(4-Methoxybenzylaminocarbonyl)-L-prolyl-L-proline benzyl ester

To trichloromethyl chloroformate (0.28 ml) in THF (40 ml) were dropwise added 4-methoxybenzylamine (0.61 ml) and triethylamine (0.65 ml) in THF (20 ml) at −20° C. over 10 minutes. After stirring for 1 hour, L-prolyl-L-proline benzyl ester hydrochloride (1.57 g) as obtained by treating N-(t-butoxycarbonyl)-L-prolyl-L-proline benzyl ester obtained in Example 23-A) with 4N hydrochloric acid/1,4-dioxane in dichloromethane (20 ml) and triethylamine (1.3 ml) were added dropwise thereto, followed by stirring for 0.5 hour. The reaction mixture was poured into ice-water and extracted with ethyl acetate. The organic layer was washed with 1N hydrochloric acid, a saturated aqueous solution of sodium bicarbonate and saturated brine in order, dried over anhydrous magnesium sulfate, and concentrated. The residue was purified by silica gel column chromatography (eluate; ethyl acetate) to give 1.34 g of the title compound.

B) (2S)-1-[N-(4-Methoxybenzylaminocarbonyl)-L-prolyl]-2-{[(S)-4-methoxyphenylsulfinyl]acetyl}pyrrolidine By the same procedure as in Example 15-D) using N-( 4-methoxybenzylaminocarbonyl)-L-prolyl-L-proline benzyl ester (1.30 g) and (S)-(−)-4-methoxyphenyl methyl sulfoxide (480 mg) as obtained in Example 15-C), there was obtained 460 mg of the title compound as colorless needles (See Table 7).

EXAMPLE 25

(2S)-1-[N-(4-Methoxybenzylaminocarbonyl)-L-prolyl]-2-(4-methoxyphenoxyacetyl)pyrrolidine (Compound 25)

A) (2S)-2-[1-Hydroxy-2-(4-methoxyphenoxy)ethyl]-1-[N-( 4-methoxybenzylaminocarbonyl)-L-prolyl]pyrrolidine By the same procedure as in Example 24-A) using trichloromethyl chloroformate (0.20 ml), 4-methoxybenzylamine (449 mg), triethylamine (0.45 ml+0.89 ml) and (2S)-2-[ 1-hydroxy-2-(4-methoxyphenoxy)ethyl]-1-(L-prolyl)pyrrolidine hydrochloride (1.18 g) as obtained by treating (2S)-1-[N-(t-butoxycarbonyl)-L-prolyl]-2-[1-hydroxy-2-(4-methoxyphenoxy) ethyl]pyrrolidine obtained in Example 22-A) with 4N hydrochloric acid/1,4-dioxane, there was obtained 661 mg of the title compound.

B) (2S)-1-[N-(4-Methoxybenzylaminocarbonyl)-L-prolyl]-2-(4-methoxyphenoxyacetyl)pyrrolidine The title compound (387 mg) was obtained as colorless needles by oxidating (2S)-2-[1-hydroxy- 2-(4-methoxyphenoxy)-ethyl]-1-[N-(4-methoxybenzylaminocarbonyl)-L-prolyl]pyrrolidine (614 mg) using sulfur trioxide-pyridine complex (0.37 g) as in Example 22-C) (See Table 7).

EXAMPLE 26

(2S)-2-(4-Chlorophenoxyacetyl)-1-[N-(3-phenylpropionyl)-L-prolyl]pyrrolidine (Compound 26)

A) (2S)-1-(tert-Butoxycarbonyl)-2-(1,2-epoxyethyl)pyrrolidine

DMSO (200 ml) was added to sodium hydride (60% NaH, 24.0 g), and the mixture was stirred at 70° C. for 1 hour. The reaction mixture was cooled to room temperature and THF (200 ml) was added. The mixture was cooled to −5° C., and thereto was dropwise added a solution of trimethylsulfonium iodide (122.5 g) in DMSO (400 ml). After stirring for 1 minute, a solution of N-(tert-butoxycarbonyl)-L-prolinal (60.0 g) in THF (200 ml) was added quickly, followed by stirring at 0° C. for 1 hour. The reaction mixture was poured into ice water and extracted with ethyl acetate. The extract was washed with saturated brine, dried over anhydrous sodium sulfate and concentrated to give the crude product of the title compound (54.9 g), which was then used in the next reaction without purification.

B) (2S)-1-(tert-Butoxycarbonyl)-2-[2-(4-chlorophenoxy)-1hydroxyethyl]pyrrolidine To a solution of (2S)-1-(tert-butoxycarbonyl)-2-(1,2-epoxyethyl)pyrrolidine (1.50 g) in methanol (5 ml) were added 4-chlorophenol (1.90 g) and 1M sodium methoxide in methanol (7.1 ml), followed by 19 hour' reflux at 70° C. The reaction mixture was poured into ice water and extracted with ethyl acetate. The organic layer was washed with 2N sodium hydroxide, saturated ammonium chloride and saturated brine, dried over anhydrous magnesium sulfate, and concentrated to give a etude product of the title compound (1.95 g).

C) N-(3-Phenylpropionyl)-L-proline

To a solution of L-proline benzyl ester hydrochloride (20.0 g) in methylene chloride (250 ml) were added triethylamine (11.5 ml), 3-phenylpropionic acid (13.7 g) and DCC (18.8 g) under ice-cooling, and the mixture was stirred for 2 hours. After stirring at room temperature for 14 hours, the insoluble material was filtered off, and the filtrate was concentrated. The residue was dissolved in ethyl acetate, and the solution was washed with 1N hydrochloric acid, saturated aqueous solution of sodium bicarbonate and saturated brine, dried over anhydrous magnesium sulfate, and concentrated. The residue was purified by silica gel column chromatography (eluate: hexane-ethyl acetate). To thus-obtained N-(3-phenylpropionyl)-L-proline benzyl ester (26.1 g) in 1% water-containing methanol (200 ml) was added 10% Pd—C (3.0 g), and the mixture was stirred at room temperature under hydrogen atmosphere for 2.5 hours. The catalyst was filtered off, and the filtrate was concentrated to give 17.4 g of the title compound.

D) (2S)-2-[2-(4-Chlorophenoxy)-1-hydroxyethyl]- 1-[N-(3-phenylpropionyl)-L-prolyl]pyrrolidine (2S)-1-(tert-Butoxycarbonyl)-2-[2-(4-chlorophenoxy)-1-hydroxyethyl]pyrrolidine (1.93 g) was dissolved in 4N hydrochloric acid/1,4-dioxane (20 ml), and the mixture was stirred at room temperature for 45 minutes. The reaction mixture was concentrated to dryness, and the resultant residue was dissolved in a mixure of methylene chloride (20 ml) and DMF (5 ml). N-Methylmorpholine (0.7 ml), N-(3-phenylpropionyl)-L-proline (1.50 g) and HOBt (915 mg) were added thereto. The reaction mixture was cooled in an ice bath, and then water-soluble cabodiimide hydrochloride (1.30 g) was added thereto, followed by 2 hours' stirring. After stirring at room temperature for 14 hours, the reaction mixture was concentrated. The residue was dissolved in ethyl acetate, and the solution was washed with 1N hydrochloric acid, saturated aqueous solution of sodium bicarbonate and saturated brine, dried over anhydrous magnesium sulfate, and concentrated. The residue was purified by silica gel column chromatography (eluate: chloroform-methanol) to give 1.61 g of the title compound.

E) (2S)-2-(4-Chlorophenoxyacetyl)-1-[N-(3-phenylpropionyl)-L-prolyl]pyrrolidine

To a solution of (2S)-2-[2-(4-chlorophenoxy)-1-hydroxyethyl]- 1-[N-(3-phenylpropionyl)-L-prolyl]pyrrolidine (1.59 g) in DMSO (10 ml) was dropwise added a solution of sulfur trioxide-pyridine complex (2.69 g) in DMSO (10 ml), followed by 1 hour's stirring at room temperature. The reaction mixture was poured into ice-water and extracted with ethyl acetate. The organic layer was washed with 1N hydrochloric acid, saturated aqueous solution of sodium bicarbonate and saturated brine, dried over anhydrous magnesium sulfate, and concentrated. The residue was purified by silica gel column chromatography (eluate: chloroform-methanol) to give 0.85 g of the title compound.

EXAMPLE 27

(2S)-2-(4-Hydroxyphenoxyacetyl)-1-[N-(3-phenylpropionyl)-L-prolyl]pyrrolidine (Compound 27)

A) (2S)-2-{2-[4-(Benzyloxy)phenoxy]-1-hydroxyethyl}-1-(tert-butoxycarbonyl)pyrrolidine By the same procedure as in Example 26-B), while using (2S)-1-(tert-butoxycarbonyl)-2-(1,2-epoxyethyl)pyrrolidine (1.50 g) and 4-(benzyloxy)phenol (2.96 g), there was obtained 1.72 g of the title compound.

B) (2S)-2-{2-[4-(Benzyloxy)phenoxy]-1-hydroxyethyl}-1-[N-(3-phenylpropionyl)-L-prolyl]pyrrolidine By the same procedure as in Example 26-D), while using ( 2S)-2-{2-[4-(benzyloxy)phenoxy]-1-hydroxyethyl}-1-(tert-butoxycarbonyl)pyrrolidine (1.71 g) and N-(3-phenylpropionyl)- L-proline (1.10 g), there was obtained 1.82 g of the title compound.

C) (2S)-2-[4-(Benzyloxy)phenoxyacetyl]-1-[N-(3-phenylpropionyl)-L-prolyl]pyrrolidine L-prolyl]pyrrolidine To a solution of (2S)-2-{2-(2-[4-(benzyloxy)phenoxy]-1-hydroxyethyl}- 1-[N-(3-phenylpropionyl)-L-prolyl]pyrrolidine (1.81 g) in DMSO (30 ml) were added pyridine (0.3 ml), trifluoroacetic acid (0.15 ml) and DCC (1.2 g), and the mixture was stirred at room temperature for 4 hours. The reaction mixture was poured into ice-water and extracted with ethyl acetate. The extract was washed with 1N hydrochloric acid, saturated aqueous solution of sodium bicarbonate and saturated brine, dried over anhydrous magnesium sulfate, and concentrated. The residue was purified by silica gel column chromatography (eluate: chloroform-methanol) to give 1.45 g of the title compound.

D) (2S)-2-(4-Hydroxyphenoxyacetyl)-1-[N-(3-phenylpropionyl)-L-prolyl]pyrrolidine To a solution of (2S)-2-[4-(benzyloxy)phenoxyacetyl]-1-[N-( 3-phenylpropionyl)-L-prolyl]pyrrolidine (1.44 g) in a mixture of methanol (50 ml), water (30 ml) and acetic acid (20 ml) was added Pd-Black (300 mg), and the mixutre was stirred at room temperature under hydrogen atmosphere for 4 hours. The reaction mixture was concentrated, and the concentrate was poured into saturated aqueous solution of sodium bicarbonate and extracted with ethyl acetate. The organic layer was washed with saturated aqueous solution of sodium bicarbonate and saturated brine, dried over anhydrous magnesium sulfate, and concentrated. The residue was purified by silica gel column chromatography (eluate: chloroform-methanol) to give 0.71 g of the title compound.

EXAMPLE 28

(2S)-1-[N-(4-Chlorobenzylaminocarbonyl)-L-prolyl]-2-(4-chlorophenoxyacetyl)pyrrolidine (Compound 28)

A) (2S)-1-[N-(tert-Butoxycarbonyl)-L-prolyl]-2-[2-(4-chlorophenoxy)-1-hydroxyethyl]pyrrolidine By the same procedure as in Example 26-D), while using (2S)- 1-(tert-butoxycarbonyl)-2-[2-(4-chlorophenoxy)-1-hydroxyethyl]pyrrolidine (2.80 g) and N-(tert-butoxycarbonyl)-L-proline (1.94 g), there was obtained 2.13 g of the title compound.

B) (2S)-1-[N-(4-Chlorobenzylaminocarbonyl)-L-prolyl]-2-[2-(4- chlorophenoxy)-1-hydroxyethyl]pyrrolidine To a solution of trichloromethyl chloroformate (0.35 ml) THF (40 ml) was dropwise added a solution of 4-chlorobenzylamine (0.71 ml) and triethylamine (0.81 ml) in THF (20 ml) under ice-cooling, and the mixture was stirred at room temperature for 1.5 hours. A suspension of (2S)-2-[2-(4-chlorophenoxy)-1-hydroxyethyl]- 1-(L-prolyl)pyrrolidine hydrochloride which had been obtained by treating (2S)-1-[N-(tert-butoxycarbonyl)-L-prolyl]- 2-[2-(4-chlorophenoxy)-l-hydroxyethyl]pyrrolidine (2.13 g) with 4N hydrochloric acid in 1,4-dioxane (20 ml), and triethylamine (0.81 ml) in methylene chloride (20 ml) was dropwise added to the reaction mixture, followed by stirring at room temperature for 1 hour. The reaction mixture was poured into ice-water and extracted with ethyl acetate. The organic layer was washed with 1N hydrochloric acid, saturated aqueous solution of sodium bicarbonate and saturated brine, dried over anhydrous magnesium sulfate, and concentrated. The residue was purified by silica gel column chromatography (eluate: chloroform-methanol) to give 2.09 g of the title compound.

C) (2S)-1-[N-(4-Chlorobenzylaminocarbonyl)-L-prolyl]-2-(4-chlorophenoxyacetyl)pyrrolidine By the same procedure as in Example 26-E), (2S)-[N-(4-chlorobenzylaminocarbonyl)-L-prolyl]-2-[2-(4-chlorophenoxy)-1-hydroxyethyl]pyrrolidine (2.08 g) was oxidized with sulfur trioxide-pyridine complex (3.27 g) to give 1.20 g of the title compound.

EXAMPLE 29

(2S)-1-[N-(4-Fluorobenzylaminocarbonyl)-L-prolyl]-2-(4-fluorophenoxyacetyl)pyrrolidine (Compound 29)

A) (2S)-1-(tert-Butoxycarbonyl)-2-[2-(4-fluorophenoxy)-1-hydroxyethyl]pyrrolidine By the same procedure as in Example 26-B), while using (2S)- 1-(tert-butoxycarbonyl)-2-(1,2-epoxyethyl)pyrrolidine (2.00 g) and 4-fluorophenol (2.21 g), there was obtained 1.91 g of the title compound.

B) (2S)-1-[N-(tert-Butoxycarbonyl)-L-prolyl]-2-[2-( 4-fluorophenoxy)-1-hydroxyethyl]pyrrolidine By the same procedure as in Example 26-D), while using (2S)- 1-(tert-butoxycarbonyl)-2-[2-(4-fluorophenoxy)-1-hydroxyethyl]pyrrolidine (1.90 g) and N-(tert-butoxycarbonyl)-L-proline (1.38 g), there was obtained 1.85 g of the title compound.

C) (2S)-1-[N-(4-Fluorobenzylaminocarbonyl)-L-prolyl]-2-[2-( 4-fluorophenoxy)-1-hydroxyethyl]pyrrolidine By the same procedure as in Example 28-B), while using 4-fluorobenzylamine (0.54 ml), trichloromethyl chloroformate (0.28 ml) and (2S)-1-[N-(tert-butoxycarbonyl)-L-prolyl]-2-[2-( 4-fluorophenoxy)-1-hydroxyethyl]pyrrolidine (1.85 g), there was obtained 1.38 g of the title compound.

D) (2S)-1-[N-(4-Fluorobenzylaminocarbonyl)-L-prolyl]-2-(4-fluorophenoxyacetyl)pyrrolidine By the same procedure as in Example 26-E), (2S)-1-[N-(4-fluorobenzylaminocarbonyl)-L-prolyl]-2-[2-(4-fluorophenoxy)-1-hydroxyethyl]pyrrolidine (1.36 g) was oxidized with sulfur trioxide-pyridine complex (1.83 g) to give 1.15 g of the title compound.

EXAMPLE 30

(2S)-1-[N-(4-Chlorobenzylaminocarbonyl)-L-prolyl]-2-(phenoxyacetyl)pyrrolidine (Compound 30)

A) (2S)-1-[N-(tert-Butoxycarbonyl)-L-prolyl]-2-(1-hydroxy-2-phenoxyethyl)pyrrolidine By the same procedure as in Example 26-D), while using (2S)- 1-(tert-butoxycarbonyl)-2-(1-hydroxy-2-phenoxyethyl)pyrrolidine (1.93 g) and N-(tert-butoxycarbonyl)-L-proline (1.36 g), there was obtained 2. i0 g of the title compound.

B) (2S)-1-[N-(4-Chlorobenzylaminocarbonyl)-L-prolyl]-2-(1-hydroxy-2-phenoxyethyl)pyrrolidine By the same procedure as in Example 28-B), while using 4-chlorobenzylamine (0.71 g), trichloromethyl chloroformate (0.3 ml) and (2S)-1-[N-(tert-butoxycarbonyl)-L-prolyl]-2-(1-hydroxy- 2-phenoxyethyl)pyrrolidine (2.00 g), there was obtained 1.13 g of the title compound.

C) (2S)-1-[N-(4-Chlorobenzylaminocarbonyl)-L-prolyl]-2-(phenoxyacetyl)pyrrolidine By the same procedure as in Example 26-E), (2S)-1-[N-(4-chlorobenzylaminocarbonyl)-L-prolyl]-2-(1-hydroxy-2phenoxyethyl)pyrrolidine (1.10 g) was oxidized with sulfur trioxide-pyridine complex (1.85 g) to give 0.75 g of the title compound.

EXAMPLE 31

(2S)-1-(N-Octanoyl-L-prolyl)-2-(phenoxyacetyl)pyrrolidine (Compound 31)

A) N-Octanoyl-L-proline benzyl ester

To a solution of L-proline benzyl ester (7.37 g) in methylene chloride (80 ml) were added triethylamine (4.3 ml), octanoyl acid (4.8 ml) and DCC (6.30 g) in this order under ice-cooling, and the mixture Has stirred for 1 hour. After stirring at room temperature for 15 hours, the insoluble material Has filtered off. The filtrate Has diluted with chloroform, and the diluted solution was washed with 1N hydrochloric acid, saturated aqueous solution of sodium bicarbonate and saturated brine, dried over anhydrous magnesium sulfate, and concentrated. The residue was purified by silica gel column chromatography (eluate: n-hexane-ethyl acetate) to give 8.09 g of the title compound.

B) N-Octanoyl-L-proline

To a solution of N-octanoyl-L-proline benzyl ester (7.04 g) in 1% water-containing methanol (70 ml) was added 10% Pd-C (0.71 g), and the mixutre was stirred under hydrogen atmosphere at room temperature for 1.5 hours. After the catalyst was filtered off, the filtrate was concentrated to give 5.08 g of the title compound.

C) (2S)-2-(1-Hydroxy-2-phenoxyethyl)-1-(N-octanoyl-L-prolyl)pyrrolidine

By the same procedure as in Example 1-D), while using ( 2S)-1-(tert-butoxycarbonyl)-2-(1-hydroxy-2-phenoxyethyl)pyrrolidine (1.50 g) and N-octanoyl-L-proline (1.18 g), there was obtained 1.16 g of the title compound.

D) (2S)-1-(N-Octanoyl-L-prolyl)-2-(phenoxyacetyl)pyrrolidine

By the same procedure as in Example 26-E), (2S)-2-(1-hydroxy-2-phenoxyethyl)-1-(N-octanoyl-L-prolyl)pyrrolidine (1.11 g) was oxidized with sulfur trioxide-pyridine complex (2.70 g) to give 0.78 g of the title compound.

EXAMPLE 32

(2S)-1-(N-Benzylaminocarbonyl)-L-prolyl)-2-(benzyloxyacetyl)-pyrrolidine (Compound 32)

A) (2S)-2-(2-Benzyloxy-1-hydroxyethyl)pyrrolidine

To a solution of benzylalcohol (2.0 ml) in DMF (10 ml) was added sodium hydride (60% dispersion in oil, 378 mg), and the mixture was stirred at room temperarture for 1 hour. A solution of (2S)-1-(tert-butoxycarbonyl)-2-(1,2-epoxyethyl)pyrrolidine (2.00 g) in DMF (10 ml) was dropwise added thereto, and the mixure was stirred for 4 hours. The reaction mixture was poured into saturated ammonium chloride and extracted with ethyl acetate. The organic layer was washed with saturated brine, dried over magnesium sulfate and concentrated. The residue was purified by silica gel column chromatography (eluate: hexane-ethyl acetate). Thus-obtained purified compound (640 mg) was dissolved in a mixture of 1,4-dioxane-water (1:1, 30 ml), and barium hydroxide octahydrate (800 mg) was added thereto, and the mixture was refluxed at 120° C. for 4 hours. After the insoluble material was filtered off, the filtrate was adjusted to pH 5–6 with 1M phosphoric acid and washed with ether. The aqueous layer was then adjusted to pH 8 with 1N sodium hydroxide and extracted with chloroform. The chloroform extract was dried over anhydrous magnesium sulfate and concentrated to give crude crystals of the title compound (297 mg).

B) (2S)-1-[N-(tert-Butoxycarbonyl)-L-prolyl]-2-(2-benzyloxy-1-hydroxyethyl)pyrrolidine By the same procedure as in Example 26-D), (2S)-2-(2-benzyloxy-1-hydroxyethyl)pyrrolidine (297 mg) and N-(tert-butoxycarbonyl)-L-proline (318 mg) were subjected to dehydration condensation reaction to give 274 mg of the title compound.

C) (2S)-1-[N-(Benzylaminocarbonyl)-L-prolyl]-2-(2-benzyloxy-1-hydroxyethyl)pyrrolidine By the same procedure as in Example 21-C), while using (2S)-1-[N-(tert-butoxycarbonyl)-L-prolyl]-2-(2-benzyloxy-1-hydroxyethyl)pyrrolidine (274 mg) and benzyl isocyanate (89 µl), there was obtained 243 mg of the title compound.

D) (2S)-1-[N-(Benzylaminocarbonyl)-L-prolyl]-2-(benzyloxyacetyl) pyrrolidine

By the same procedure as in Example 26-E), (2S)- 1-[N-(benzylaminocarbonyl)-L-prolyl]-2-(2-benzyloxy- 1-hydroxyethyl)-pyrrolidine (233 mg) was oxidized with sulfur trioxide-pyridine complex (330 mg) to give 106 mg of the title compound.

EXAMPLE 33

(2S)-1-[N-(Benzylaminocarbonyl)-L-prolyl]-2-{[(3,4-methylenedioxy)phenoxy]acetyl} pyrrolidine (Compound 33)

A) (2S)-1-(tert-Butoxycarbonyl)-2-{1-hydroxy-2-[( 3,4-methylenedioxy)phenoxy]ethyl} pyrrolidine By the same procedure as in Example 26-B), while using (2S)1-(tert-butoxycarbonyl)-2-(1,2-epoxyethyl)Pyrrolidine (2.00 g) and (3,4-methylenedioxy)phenol (2.72 g), there was obtained 2.41 g of the title compound.

B) (2S)-1-[N-(tert-Butoxycarbonyl)-L-prolyl]-2-{1-hydroxy- 2-[(3,4-methylenedioxy)phenoxy]ethyl} pyrrolidine By the same procedure as in Example 26-D), while using (2S) 1-(tert-butoxycarbonyl)-2-{1-hydroxy-2-[(3,4-methylenedioxy)phenoxy]ethyl} pyrrolidine (2.38 g) and N-(tert-butoxycarbonyl)-L-proline (1.60 g), there was obtained 2.07 g of the title compound.

C) (2S)-1-[N-(Benzylaminocarbonyl)-L-prolyl-2-{1-hydroxy-2[(3,4-methylenedioxy)phenoxy]ethyl} pyrrolidine By the same procedure as in Example 21-C), while using (2S) 1-[N-(tert-butoxycarbonyl)-L-prolyl]-2-{1-hydroxy-2-[(3,4-methylenedioxy)phenoxy]ethyl} pyrrolidine (2.07 g) and benzyl isocyanate (0.63 ml), there was obtained 2.06 g of the title compound.

D) (2S)-1-[N-(Benzylaminocarbonyl)-L-prolyl]-2-{[( 3,4-methylenedioxy)phenoxy]acetyl} pyrrolidine By the same procedure as in Example 26-E), (2S)- 1-[N-(benzylaminocarbonyl)-L-prolyl]-2-{1-hydroxy-2-[(3,4methylenedioxy)phenoxy]ethyl}pyrrolidine (2.05 g) was oxidized with sulfur trioxide-pyridine complex (2.71 g) to give 1.12 g of the title compound.

The physicochemical properties of Compounds 1 to 33 are shown in Tables 1 to 9.

TABLE 1

| Comp. No. | W—(CH$_2$)n—A—CO—B— | X | R | Properties Melting point Optical rotation (CH$_3$OH) | EI-MS (m/z) | $^1$H NMR (CDCl$_3$, δ value) |
| --- | --- | --- | --- | --- | --- | --- |
| 1 | benzyl-O-CO-N-pyrrolidinyl | S | phenyl | colorless oily substance | 452(M$^+$), 232, 204, 160, 91 | 1.7–2.2(8H, m), 3.35–3.85(4H, m), 3.81, 3.86, 3.93&3.98 (total 2H, d each, J=15.2Hz), 4.40&4.52(total 1H, dd each, J=8.0, 4.4Hz), 4.54&4.82(total 1H, t each, J=6.3Hz), 4.97, 5.04, 5.13&5.19(total 2H, d each, J=12.4Hz), 7.2~7.4(10H,m) |

TABLE 1-continued

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 2 | benzyl O-C(=O)-N-pyrrolidinyl (with wedge) | SO | phenyl | colorless oily substance | 469(MH⁺), 451(MH⁺H₂O), 232, 204, 160, 91 | 1.7–2.8(8H, m), 3.35–3.85 (4H, m), 3.85, 3.88, 3.92, 4.00, 4.01, 4.07&4.11(total 2H, d each, J=14.9Hz), 4.3–4.75 (total 2H, m), 4.96, 5.03, 5.04, 5.10, 5.12, 5.17&5.18(total 2H, d each, J=12.4Hz), 7.30(5H, m), 7.52(3H, m), 7.66(2H, m) |
| 3 | benzyl O-C(=O)-N-pyrrolidinyl (with wedge) | SO₂ | phenyl | colorless oily substance | 485(MH⁺), 232, 204, 160, 91 | 1.7–2.2(8H, m), 3.35–3.90(4H, m), 4.19, 4.24, 4.56&4.61(total 2H, d each, J=13.8Hz), 4.39, 4.49&4.73(total 2H, m), 4.95, 5.03, 5.14&5.18(total 2H, d each, J=12.4Hz), 7.35(5H, m), 7.57(2H, m), 7.67(1H, m), 7.89(2H, m) |

TABLE 2

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 4 | benzyl O-C(=O)-N-pyrrolidinyl | O | phenyl | colorless oily substance | 437(MH⁺), 302, 232, 204, 160, 107, 94, 91 | 1.7–2.2(8H, m), 3.4–3.9(4H, m), 4.43&4.56(1H, dd each, J=8.1, 3.6Hz), 4.66&4.93(1H, dd each, J=8.7, 5.7Hz), 4.77, 4.79& 4.85(total 2H, s, d, d, J=16.9Hz), 4.98, 5.05, 5.14&5.21 (total 2H, d each, J=12.4Hz), 6.98(3H, m), 7.2–7.4(7H, m) |
| 5 | phenyl-(CH₂)₃-C(=O)-N-pyrrolidinyl | SO | phenyl | colorless oily substance | 481(MH⁺), 463(MH⁺—H₂O), 376, 355, 313, 244, 216, 147, 91 | 1.7–2.35(12H, m), 2.65(2H, t, J=7.0Hz), 3.40, 3.56&3.88(total 4H, m), 3.85, 4.01&4.07(total 2H, d, J=14.8Hz, s, d, J=14.8Hz), 4.55–4.70(2H, m), 7.17(3H, m), 7.26(2H, m), 7.51(3H, m), 7.66(2H, m) |
| 6 | benzyl O-C(=O)-N-pyrrolidinyl | SO | 4-OCH₃-phenyl | colorless oily substance | 499(MH⁺), 483, 344, 302, 232, 204, 160, 155, 139, 91 | 1.8–2.2(8H, m), 3.3–3.7(4H, m), 3.83&3.85(3H, s each), 3.75–4.13(2H), 4.35–4.74(2H, m), 4.94–5.20(2H), 7.02(2H, m), 7.34(5H, m), 7.60(2H, m) |

TABLE 3

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 7 | benzyl carbamate-pyrrolidine | SO | 4-nitrophenyl | colorless oily substance | 514(MH⁺), 497, 379, 344, 309, 302, 233, 204, 171, 160, 91 | 1.8~2.2(8H, m), 3.4~5.2(10H, m), 7.35, (5H, m), 7.88(2H, m), 8.39(2H, m) |
| 8 | benzyl carbamate-pyrrolidine | SO | —CH(CH₃)₂ | colorless oily substance | 434(M⁺), 418, 392, 343, 301, 232, 204, 160, 91 | 1.31(6H, m), 1.8~2.2(8H, m), 2.96(1H, m), 3.3~3.95(6H, m), 4.35~4.8(2H, m), 4.95~5.2(2H, 7.35(5H, m) |
| 9 | benzyl carbamate-pyrrolidine | S(=O)(=NH) | phenyl | colorless oily substance [α]$_D$ −177° | — | 1.7~2.2(8H, m), 3.37, 3.50, 3.60&3.80(total 4H, m each), 3.85, 3.89, 4.06&4.10(total 2H, d each, J=14.9Hz), 4.33&4.60 (total 1H, dd each, J=8.2, 4.6Hz), 4.41&4.52(total 1H, dd each, J=8.3, 3.6Hz), 7.30(5H, m), 7.52(3H, m), 7.70(2H, m) |

TABLE 4

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 10 | benzyl carbamate-pyrrolidine | S(=O)(=NH) | phenyl | colorless needles mp 120~121° C. [α]$_D$ −23.4° | — | 1.7~2.2(8H, m), 3.35~3.65&3.80(total 4H, m), 3.94, 4.01&4.05(total 2H, d, d, s, J=13.4Hz), 4.39&4.51(total 1H, dd each, J=8.1, 3.3Hz), 4.46&4.73(total 1H, dd each, J=7.5, 5.7Hz), 4.97, 5.03, 5.12&5.17(total 2H, d, each, J=12.4Hz), 7.34(5H, m), 7.51(3H, m), 7.69(2H, m) |
| 11 | benzyl carbamate-pyrrolidine | S(=O)(=NH) | 4-methoxyphenyl | colorless oily substance [α]$_D$ −183° | 498(M⁺), 482, 391, 232, 204, 160, 155, 139, 91 | 1.7~2.2(8H, m), 3.35~3.65& 3.77(total 4H, m), 3.80&3.84 (total 1H, d each, J=14.7Hz), 3.86(3H, s), 4.07&4.11(total 1H, d each, J=14.7Hz), 4.33&4.60 (total 1H, dd each, J=8.0, 4.8Hz), 4.41&4.52(total 1H, dd each, J=8.3, 3.8Hz), 4.96, 5.03, 5.10&5.17(total 2H, d each, J= 12.4Hz), 7.02(2H, m), 7.23~ 7.35(5H, m), 7.62(2H, m) |

TABLE 4-continued

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 12 | benzyl carbamate-pyrrolidine | S(=O) (sulfoxide) | phenyl-OCH₃ | colorless oily substance [α]_D −61.2° | 498(M⁺), 482, 391, 343, 301, 232, 204, 160, 155, 139, 91 | 1.7~2.2(8H, m), 3.35~3.65& 3.79(total 4H, m), 3.85(3H, s), 3.95, 4.00&4.04(total 2H, s, d, d, J=14.0Hz), 4.40&4.51(total 1H, dd each, J=8.2, 4.0Hz), 4.46& 4.72(total 1H, dd each, J=7.6, 5.5Hz), 5.96, 5.04, 5.11& 5.18(total 1H, d each, J= 12.3Hz),7.02(2H, m), 7.27~ 7.37(5H, m), 7.61(2H, m) |
| 13 | benzyl carbamate-pyrrolidine | S(=O) (sulfoxide) | phenyl-CH₃ | colorless oily substance [α]_D −216° | 4.82(M⁺), 466, 343, 301, 232, 204, 160, 139, 91 | 1.7~2.2(8H, m), 2.42(3H, s), 3.36, 3.50, 3.61&3.79(total 4H, m),3.80&3.84(total 1H, d each, J=14.8Hz), 4.05&4.09(total 1H, d each, J=14.8Hz), 4.33&4.60 (total 1H, dd each, J=7.9, 4.7Hz), 4.41&4.52(total 1H, dd each, J=8.3, 3.7(Hz), 4.96, 5.03, 5.10&5.17(total 2H, d each, J=12.2Hz), 7.28(2H, m), 7.33(5H, m), 7.55(2H, m) |

TABLE 5

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 14 | benzyl carbamate-pyrrolidine | S(=O) (sulfoxide) | phenyl-CH₃ | colorless oily substance [α]_D −30.0° | 482(M⁺), 466, 343, 301, 232, 204, 160, 139, 91 | 1.7~2.2(8H, m), 2.41(3H, s), 3.35~3.65&3.81(total 4H, m), 3.90, 3.97, 3.98&4.04(total 2H, d each, J=14.0Hz), 4.93&4.51 (total 1H, dd each, J=8.2, 3.9Hz), 4.46&4.73 (total 1H, dd each, J=7.8, 5.7Hz), 4.96, 5.03, 5.11&5.18(total 2H, d each, J=12.4Hz), 7.27~ 7.35(6H, m), 7.54(2H, m) |
| 15 | phenylpropanoyl-pyrrolidine | S(=O) (sulfoxide) | phenyl-OCH₃ | colorless oily substance [α]_D −192° | 496(M⁺), 4.80, 341, 299, 230, 202, 155 | 1.8~2.2(8H, m), 2.61(2H, m), 2.94(2H, t, J=8.2Hz),3.40, 3.60& 3.88(total 4H, m), 3.82(1H, d, J=14.9Hz), 3.85(3H, s), 4.10 (1H, d, J=14.9Hz), 4.59(1H, dd, J=8.2, 5.0Hz), 4.64(1H, dd, J=7.7, 3.7Hz), 7.01(2H, m), 7.19(2H, m), 7.28(3H, m), 7.62(2H, m). |
| 16 | phenylpropanoyl-pyrrolidine | S(=O) (sulfoxide) | phenyl-CH₃ | colorless needles mp 127~ 129° C. [α]_D −235° | 480(M⁺), 464, 341, 299, 230, 202, 139 | 1.8~2.2(8H, m), 2.42(3H, s), 2.58(2H, m), 2.94(2H, t, J= 8.2Hz), 3.41, 3.62&3.90(total 4H, m), 3.83(1H, d, J=14.9Hz), 4.08(1H, d, J=14.9Hz), 4.59 (1H, dd, J=8.1, 4.9Hz), 4.64 (1H, dd, J=7.7, 3.6Hz), 7.18~7.34(7H, m), 7.55(2H, m) |

TABLE 5-continued

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 17 | Ph-CH₂CH₂-C(=O)-N-pyrrolidinyl | S(=O) | Ph | colorless needles mp 163~166° C. [α]$_D$ −231° | 466(M⁺), 450, 341, 299, 230, 202, 125 | 1.8~2.2(8H, m), 2.60(2H, m), 2.94(2H, t, J=8.1Hz), 3.42, 3.61&3.85(total 4H, m), 3.86 (1H, d, J=15.0Hz), 4.09(1H, d, J=15.0Hz), 4.59(1H, dd, J= 15.0Hz), 4.59(1H, dd, J=8.0, 4.9Hz), 4.64(H, dd, J=7.7, 3.8Hz), 7.16~7.34(5H, m), 7.53(3H, m), 7.66(2H, m) |

TABLE 6

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 18 | Ph-CH₂-O-C(=O)-N-pyrrolidinyl | O | Ph-OCH₃ | colorless oily substance [α]$_D$ −41.9° | 466(M⁺), 343, 301, 232, 204, 160, 91 | 1.8~2.2(8H, m), 3.4~3.9(4H, m), 3.76& 3.77(total 3H, s each),4.45, 4.55, 4.67&4.91(total 2H, m), 4.72, 4.74&4.79 (total 2H, s, d, d, J=16.9Hz), 4.97, 5.04, 5.13&5.19(total 2H, d, each, J=12.4Hz), 6.83(4H, m), 7.27~7.37(5H, m) |
| 19 | Ph-CH₂CH₂-C(=O)-N-pyrrolidinyl | O | Ph | colorless needles mp 122.8~124° C. [α]$_D$ −116° | 434(M⁺), 341, 299, 230, 202 | 1.8~2.2(8H, m), 2.61(2H, m), 2.95(2H, m), 3.35~3.70&4.06(total 4H, m), 4.62(1H, dd, J=7.6, 5.3Hz), 4.68(1H, dd, J=8.1, 4.2Hz), 4.84(1H, d, J=18.0Hz), 4.98(1H, d, J=18.0Hz), 6.90~7.32(10H, m) |
| 20 | Ph-CH₂CH₂-C(=O)-N-pyrrolidinyl | O | Ph-OCH₃ | colorless needles | 464(M⁺), 341, 299, 230, 202 | 1.85~2.2(8H, m), 2.61(2H, m), 2.94 (2H, m), 3.35~3.70&4.05(total 4H, m), 3.66(3H, s), 4.61(1H, dd, J=7.7, 5.3Hz), 4.68(1H, dd, J=7.0, 5.3Hz), 4.80(1H, d, J=17.9Hz), 4.92(1H, d, J=17.9Hz), 6.78~7.29(9H, m) |
| 21 | Ph-CH₂-NH-C(=O)-N-pyrrolidinyl | O | Ph | colorless particles mp 138.1~140.4° C. | 435(M⁺), 300, 231, 203, 91 | 1.8~2.3(8H, m), 3.32(1H, m), 3.51(1H, m), 3.62(1H, m), 3.90(1H, m), 4.32(1H, dd, J=14.5, 4.9Hz), 4.52(1H, dd, J=14.5, 6.0Hz),4.63(1H, t, J=5.4Hz), 4.70(1H, dd, J=7.8, 3.2Hz), 4.78(1H, d, J=17.0Hz), 4.85(1H, d, J=17.0Hz), 4.90(1H, dd, J=7.9, 5.4Hz), 6.9~7.0(3H, m), 7.25~7.35(7H, m) |

TABLE 7

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 22 | (phenyl)-CH₂-NH-C(=O)-N-(pyrrolidinyl) | O | 4-OCH₃-phenyl | colorless needles mp 127.7~129.1° C. [α]_D −48.9° | CI-MS, 466(MH⁺), 315, 231, 125, 91 | 1.8~2.3(8H, m), 3.32(1H, m), 3.51(1H, m), 3.62(1H, m), 3.76 (3H, s), 3.90(1H, m), 4.31(1H, dd, J=14.6, 5.0Hz), 4.53(1H, dd, J=14.6, 6.2Hz), 4.68 (2H, m), 4.72(1H, d, J=16.8Hz), 4.79(1H, d, J=16.8Hz), 4.86(1H, dd, J=8.3, 5.3Hz), 6.8~6.9(4H, m), 7.2~7.4(5H, m) |
| 23 | (phenyl)-CH₂-NH-C(=O)-N-(pyrrolidinyl) | S(=O)(CH₃) | 4-OCH₃-phenyl | colorless needles mp 140~142° C. [α]_D −213° | 497(M⁺), 342, 231, 203, 155, 91 | 1.9~2.3(8H, m), 3.31(1H, m), 3.47(1H, m), 3.61(1H, m), 3.83(1H, d, J=14.8Hz), 3.86(3H, s), 3.89(1H, m), 4.10(1H, d, J=14.8Hz), 4.31(1H, dd, J=14.6, 5.0Hz), 4.50(1H, dd, J=14.6, 6.0Hz), 4.55~4.7(3H, m), 7.03(2H, d, J=8.9Hz), 7.25~7.35(5H, m), 7.61(2H, d, J=8.9Hz) |
| 24 | (OCH₃-phenyl)-CH₂-NH-C(=O)-N-(pyrrolidinyl) | S(=O)(CH₃) | 4-OCH₃-phenyl | colorless needles mp 165.5~167.5° C. [α]_D −192° | 527(M⁺), 261, 233, 155, 121 | 1.9~2.2(8H, m), 3.29(1H, m), 3.46(1H, m), 3.61(1H, m), 3.78(3H, s), 3.83(1H, d, J=14.8Hz), 3.86(3H, s), 3.89(1H, m), 4.10(1H, d, J=14.8Hz), 4.24(1H, br d, J=14.2Hz), 4.42(1H, br d, J=14.2Hz), 4.53(1H, br s), 4.59(1H, dd, J=8.0, 5.0Hz), 4.67(1H, dd, J=7.7, 3.2Hz), 6.84(2H, d, J=8.6Hz), 7.02(2H, d, J=8.8Hz), 7.22(2H, d, J=8.6Hz), 7.22(2H, d, J=8.6Hz), 7.61(2H, d, J=8.8Hz) |
| 25 | (OCH₃-phenyl)-CH₂-NH-C(=O)-N-(pyrrolidinyl) | O | 4-OCH₃-phenyl | colorless needles mp 130.2~132.5° C. [α]_D −43.9° | FAB-MS, 496(MH⁺), 372, 359 | 1.8~2.3(8H, m), 3.30(1H, m), 3.48(1H, m), 3.62(1H, m), 3.76 (3H, s), 3.79(3H, s), 3.91(1H, m), 4.25(1H, dd, J=14.2, 4.8Hz), 4.44(1H, dd, J=14.2, 5.9Hz), 4.54(1H, br t, J=5.4Hz), 4.69(1H, dd, J=7.8, 3.2Hz), 4.73(1H, d, J=16.8Hz), 4.80(1H, d, J=16.8Hz), 4.89 (1H, dd, J=8.4, 5.7Hz), 6.8~6.9(6H, m), 7.25(2H, d, J=8.6Hz) |

TABLE 8

| Comp. No. | W―(CH₂)n―A―CO―B― | X | R | Properties Melting point Optical rotation (CH₃OH) | EI-MS (m/z) | ¹H NMR (CDCl₃, δ value) |
|---|---|---|---|---|---|---|
| 26 | Ph-CH₂CH₂-C(=O)-N-(pyrrolidine) | O | 4-Cl-C₆H₄ | colorless needles mp 99.0~101.2° C. [α]$_D$ −113° | EI-MS: 468(M⁺), 341, 299, 231, 202, 105, 91 | 1.83~2.23(8H, m), 2.63(2H, m), 2.97(2H, t, J=7.7Hz), 3.41(1H, ddd, J=9.7, 7.1, 7.1Hz), 3.63(2H, m), 3.94(1H, ddd, J=9.4, 6.6, 6.6Hz), 4.66(1H, dd, J=7.5, 3.5Hz), 4.77(1H, d, J=17.0Hz), 4.85(1H, dd, J=8.2, 5.5Hz), 4.87(1H, d, J=17.0Hz), 6.85(2H, d, J=6.9Hz), 7.20~7.31(7H, m) |
| 27 | Ph-CH₂CH₂-C(=O)-N-(pyrrolidine) | O | 4-OH-C₆H₄ | colorless needles mp 134.1~135.6° C. [α]$_D$ −113° | EI-MS: 450(M⁺), 341, 299, 230, 202, 105, 91 | 1.8~2.2(8H, m), 2.63(2H, m), 2.95(2H, t, J=7.8Hz), 3.40(1H, m), 3.62(2H, m), 3.90(1H, m), 4.58(1H, d, J=17.0Hz), 4.62(1H, d, J=17.0Hz), 4.67(1H, dd, J=7.9, 3.8Hz), 4.92(1H, dd, J=8.4, 5.1Hz), 6.72(4H, m), 7.17~7.39(6H, m) |
| 28 | 4-Cl-C₆H₄-CH₂-NH-C(=O)-N-(pyrrolidine) | O | 4-Cl-C₆H₄ | colorless needles mp 169.0~171.5° C. [α]$_D$ −98.5° | EI-MS: 503(M⁺), 376, 334, 266, 265, 238, 237 | 1.8~2.2(8H, m), 3.33(1H, ddd, J=7.6, 7.2, 7.2Hz), 3.50(1H, m), 3.61(1H, ddd, J=9.5, 6.8, 6.8Hz), 3.88(1H, ddd, J=9.5, 6.8, 6.8Hz), 4.27(1H, dd, J=15.0, 5.3Hz), 4.49(1H, dd, J=15.0, 6.1Hz), 4.68(1H, dd, J=7.8, 3.4Hz), 4.75(1H, dd, J=6.1, 5.3Hz), 4.75(1H, d, J=16.9Hz), 4.79(1H, dd, J=5.9, 2.3Hz), 4.85(1H, d, J=16.9Hz), 6.85(2H, m), 7.20~7.30(6H, m) |
| 29 | 4-F-C₆H₄-CH₂-NH-C(=O)-N-(pyrrolidine) | O | 4-F-C₆H₄ | colorless needles mp 147.5~148.2° C. [α]$_D$ −99.4° | EI-MS: 471(M⁺), 360, 318, 302, 249, 221, 109 | 1.8~2.2(8H, m), 3.32(1H, m), 3.51(1H, m), 3.61(1H, ddd, J=9.6, 6.8, 6.8Hz), 4.28(1H, dd, J=14.7, 5.2Hz), 4.48(1H, dd, J=14.7, 6.0Hz), 4.67(2H, m), 4.75(1H, d, J=16.9Hz), 4.83(1H, d, J=16.9Hz), 4.85(1H, d, J=16.9Hz), 6.83~6.99(6H, m), 7.27(2H, m) |

TABLE 9

| Comp. No. | W―(CH₂)n―A―CO―B― | X | R | Properties Melting point Optical rotation (CH₃OH) | EI-MS (m/z) | ¹H NMR (CDCl₃, δ value) |
|---|---|---|---|---|---|---|
| 30 | 4-Cl-C₆H₄-CH₂-NH-C(=O)-N-(pyrrolidine) | O | C₆H₅ | colorless particles mp 145~147° C. [α]$_D$ −84.2° | EI-MS: 469(M⁺), 376, 284, 265, 237, 163, 132, 125 | 1.82~2.22(8H, m), 3.33(1H, m), 3.52(1H, m), 3.61(1H, ddd, J=9.5, 6.6, 6.6Hz), 3.88(1H, ddd, J=9.4, 6.9, 6.9Hz), 4.28(1H, dd, J=15.0, 5.3Hz), 4.49(1H, dd, J=15.0, 6.2Hz), 4.69(1H, dd, J=7.8, 2.1Hz), 4.75(1H, m), 4.77(1H, d, J=16.8Hz), 4.84(1H, d, J=16.8Hz), 4.86(1H, dd, J=8.9, 4.6Hz), 6.91(2H, d, J=7.8Hz), 6.98(1H, t, J=7.4Hz), 7.20~7.31(6H, m) |

TABLE 9-continued

| Comp. No. | W—(CH₂)n—A—CO—B— | X | R | Properties Melting point Optical rotation (CH₃OH) | EI-MS (m/z) | ¹H NMR (CDCl₃, δ value) |
|---|---|---|---|---|---|---|
| 31 | H₃C-(chain)-C(=O)-N(pyrrolidine) | O | phenyl | colorless oily substance [α]_D −106.4° | EI-MS: 428(M⁺), 335, 293, 224, 196, 107 | 0.87(3H, t, J=6.8Hz), 1.28(8H, m), 1.63(2H, m), 1.82~2.39(10H, m), 3.49(1H, ddd, J=9.7, 6.8, 6.8Hz), 3.64(2H, m), 3.94(1H, ddd, J=9.3, 6.9, 6.9Hz), 4.66(1H, dd, J=8.1, 3.8Hz), 4.77(1H, d, J=16.7Hz), 4.84(1H, d, J=16.7Hz), 4.89(1H, dd, J=8.0, 5.3Hz), 6.90(2H, d, J=7.8Hz), 6.97(1H, t, J=7.3Hz), 7.26(2H, m) |
| 32 | PhCH₂-NH-C(=O)-N(pyrrolidine) | O | ethylphenyl (benzyl) | colorless needles mp 111.5~ 113.0° C. [α]_D −97.2° | EI-MS: 449(M⁺), 358, 231, 203, 163 | 1.75~2.25(8H, m), 3.30(1H, m), 3.48(1H, m), 3.58(1H, ddd, J=9.6, 6.6, 6.6Hz), 3.86(1H, ddd, J=9.4, 7.0, 7.0Hz), 4.20(1H, d, J= 17.1Hz), 4.29(1H, dd, J=14.8, 3.8Hz), 4.52(1H, dd, J=14.8, 5.7Hz), 4.59(1H, s), 4.68(1H, dd, J=7.8, 3.4Hz), 4.75(1H, dd, J=8.5, 5.4Hz), 4.76(1H, m), 7.22~ 7.36(10H, m) |
| 33 | PhCH₂-NH-C(=O)-N(pyrrolidine) | O | methylenedioxyphenyl (methyl-substituted) | colorless amorphous solid [α]_D −97.5° | EI-MS: 479(M⁺), 342, 328, 231, 203, 163, 137 | 1.80~2.23(8H, m), 3.32(1H, m), 3.51(1H, m), 3.60(1H, ddd, J=9.4, 6.7, 6.7Hz), 3.89(1H, ddd, J=9.5, 6.6, 6.6Hz), 4.29(1H, dd, J=14.7, 4.8Hz), 4.54(1H, dd, J=14.7, 6.2Hz), 4.67~4.83(3H, m), 4.68(1H, d, J=16.8Hz), 4.76(1H, d, J= 16.8Hz), 5.90(2H, s), 6.31(1H, dd, J=8.5, 2.5Hz), 6.52(1H, d, J= 2.5Hz), 6.67(1H, d, J=8.5Hz), 7.20~7.32(5H, m) |

Note that the present invention is not limited to these examples, and Compounds 34–45 shown in Table 10, for example, are also encompassed in the present invention.

| Comp. No. | Formula |
|---|---|
| 34 | H₃C-(CH₂)ₙ-C(=O)-N(pyrrolidine)-C(=O)-N(pyrrolidine)-C(=O)-CH₂-S(=O)-Ph |
| 35 | 4-Cl-C₆H₄-CH₂-NH-C(=O)-N(pyrrolidine)-C(=O)-N(pyrrolidine)-C(=O)-CH₂-S(=O)-C₆H₄-4-OCH₃ |
| 36 | PhCH₂-O-C(=O)-N(pyrrolidine)-C(=O)-N(pyrrolidine)-C(=O)-CH₂-NH-Ph |

| Comp. No. | Formula |
|---|---|

37: 4-F-C6H4-CH2-NH-C(O)-N(pyrrolidine)-C(O)-(pyrrolidine)-C(O)-CH2-O-C6H4-4-OCH3

38: C6H5-CH2-CH2-C(O)-N(pyrrolidine)-C(O)-(pyrrolidine)-C(O)-CH2-O-C6H4-4-CF3

39: C6H5-CH2-O-C(O)-N(pyrrolidine)-C(O)-(pyrrolidine)-C(O)-CH2-S(O)-C6H4-4-Cl

40: C6H5-CH2-O-C(O)-N(pyrrolidine)-C(O)-(pyrrolidine)-C(O)-CH2-S(O)-C6H4-4-CF3

41: C6H5-CH2-O-C(O)-N(pyrrolidine)-C(O)-(pyrrolidine)-C(O)-CH2-S(O)-CH2-C6H5

42: C6H5-CH2-O-C(O)-N(pyrrolidine)-C(O)-(pyrrolidine)-C(O)-CH2-S(O)-(2-naphthyl)

43: C6H5-CH2-CH2-CH2-C(O)-N(2,3-dihydropyrrole)-C(O)-(pyrrolidine)-C(O)-CH2-S(O)-C6H5

44: 4-Cl-C6H4-CH2-O-C(O)-N(pyrrolidine)-C(O)-(pyrrolidine)-C(O)-CH2-S(O)-CH(CH3)2

45: 4-CH3O-C6H4-CH2-O-C(O)-N(pyrrolidine)-C(O)-(pyrrolidine)-C(O)-CH2-S(O)-C6H4-4-NO2

EXAMPLE 46

(2S)-2-(Phenoxyacetyl)-1-[N-(phenoxyacetyl)-L-prolyl]pyrrolidine (Compound 46)

A) (2S)-1-(tert-Butoxycarbonyl)-2-(1,2-epoxyethyl)pyrrolidine

DMSO (20 ml) was added to sodium hydride (1.55 g, NaH content 60%), and the mixture was stirred at 70° C. for 1 hour. The reaction mixture was cooled to room temperature and THF (20 ml) was added. The mixture was cooled to −5° C., and thereto was dropwise added a solution of trimethylsulfonium iodide (7.90 g) in DMSO (30 ml) over 3 minutes. After stirring for 1 minute, a solution of tert-butoxycarbonyl-L-prolinal (5.13 g) in THF (15 ml) was added quickly, followed by stirring at room temperature for 1 hour. The reaction mixture was poured into ice-water (300 ml), and extracted with chloroform. The extract was washed with saturated brine, dried over anhydrous sodium sulfate and concentrated. The residue was purified by silica gel column chromatography (eluate: hexane-ethyl acetate) to give two diastereomers of the title compound, 3.12 g of its less polar compound and 1.28 g of its more polar compound. (Configuration of the epoxy moiety of the both has not been identified.) The less polar compound was used in the following reactions.

B) (2S)-1-(tert-Butoxycarbonyl)-2-(1-hydroxy-2-phenoxyethyl)-pyrrolidine

To a solution of (2S)-1-(tert-butoxycarbonyl)-2-(1,2-epoxyethyl)pyrrolidine (1.50 g) in methanol (30 ml) were added phenol (1.50 g) and sodium methoxide (380 mg), and the mixture was stirred under reflux for 16 hours. The reaction mixture was concentrated, and the residue was dissolved in ether, washed with 10% citric acid, saturated aqueous sodium bicarbonate, and saturated brine successively, dried over anhydrous magnesium sulfate, and concentrated. The residue was purified by silica gel column chromatography (eluate: hexane-ethyl acetate) to give 1.10 g of the title compound.

C) (2S)-1-[N-(tert-Butoxycarbonyl)-L-prolyl]-2-(1-hydroxy-2-phenoxyethyl)pyrrolidine (2S)-1-(tert-Butoxycarbonyl)-2-(1-hydroxy-2-phenoxyethyl)-pyrrolidine (1.93 g) was dissolved in 31 ml of 4N hydrochloric acid/1,4-dioxane, and the mixture was, stirred at room temperature for 0.5 hour. The reaction mixture was concentrated to dryness, and the residue obtained was dissolved in DMF (15 ml), after which N-(tert-butoxycarbonyl)-L-proline (1.36 g), N-methylmorpholine (0.69 ml), and HOBt (1.02g) were added thereto. After the reaction mixture was cooled to −25° C., DCC (1.30 g) was added thereto, and the mixture was stirred at −25° C. to 0° C. for 3 hours, and then at room temperature for 16 hours. The precipitated dicyclohexylurea was filtered off, and the filtrate was concentrated. The residue was dissolved in ethyl acetate, washed with saturated aqueous sodium bicarbonate, and saturated brine successively, dried over anhydrous magnesium sulfate, and concentrated. The residue was purified by silica gel column chromatography (eluate: chloroform-methanol) to give 2.10 g of the title compound.

D) (2S)-2-(1-Hydroxy-2-phenoxyethyl)-1-[N-(phenoxyacetyl)-L-prolyl]pyrrolidine (2S)-1-[N-(tert-Butoxycarbonyl)-L-prolyl]-2-(1-hydroxy-2-phenoxyethyl)pyrrolidine (996 mg) was dissolved in 4N hydrochloric acid/1,4-dioxane (12 ml), and the mixture was stirred at room temperature for 40 minutes. The reaction mixture was concentrated to dryness, and the residue obtained was dissolved in methylene chloride (10 ml). After triethylamine (0.68 ml) was added thereto under ice-cooling, phenoxyacetyl chloride (0.34 ml) was dropwise added. After stirring the mixture under ice-cooling for 0.5 hour, and then at room temperature for 1.5 hours, the reaction mixture was poured into ice-water, and extracted with methylene chloride. The organic layer was washed with saturated aqueous sodium bicarbonate, and saturated brine successively, dried over anhydrous magnesium sulfate, and concentrated. The residue was purified by silica gel column chromatography (eluate: chloroform-methanol) to give 1.05 g of the title compound.

E) (2S)-2-(Phenoxyacetyl)-1-[N-(phenoxyacetyl)-L-prolyl] pyrrolidine (2S)-2-(1-Hydroxy-2-phenoxyethyl)-1-[N-(phenoxyacetyl)-L-prolyl]pyrrolidine (998 mg) was dissolved in a mixture of DMSO (6 ml) and benzene (3 ml), and thereto were added pyridine (0.18 ml) and trifluoroacetic acid (0.09 ml). After ice-cooling the mixture, DCC (941 mg) was added thereto, and the mixture was stirred at room temperature for 2.5 hours. The precipitated dicyclohexylurea was filtered off, and the filtrate was poured into ice-cold 1N hydrochloric acid, followed by extraction with ethyl acetate. The organic layer was washed with saturated aqueous sodium bicarbonate and saturated brine successively, dried over anhydrous magnesium sulfate, and concentrated. The residue was purified by silica gel column chromatography (eluate: chloroform-methanol) to give 759 mg of the title compound.

EXAMPLE 47

(2S)-2-(4-Methoxyphenoxyacetyl)-1-[N-(phenoxyacetyl)-L-prolyl]pyrrolidine (compound 47)

A) (2S)-1-(tert-Butoxycarbonyl)-2-[1-hydroxy-2-(4-methoxyphenoxy)ethyl]pyrrolidine To a solution of (2S)-1-(tert-butoxycarbonyl)-2-(1,2-epoxyethyl)pyrrolidine (11.70 g) prepared in Example 46-A) in methanol (50 ml) were added 4-methoxyphenol (13.60 g) and 1M sodium methoxide-methanol solution (54.9 ml), and the mixture was stirred at 70° C. for 18 hours. The reaction mixture was poured into saturated aqueous ammonium chloride, and extracted with ethyl acetate. The extract was washed with saturated brine, dried over anhydrous magnesium sulfate, and concentrated. The residue was purified by silica gel column chromatography (eluate: hexane-ethyl acetate) to give 14.20 g of the title compound.

B) (2S)-1-[N-(tert-Butoxycarbonyl)-L-prolyl]-2-[1-hydroxy- 2-(4-methoxyphenoxy)ethyl]pyrrolidine (2S)-1-(tert-Butoxycarbonyl)-2-[1-hydroxy-2-(4-methoxyphenoxy)ethyl]pyrrolidine (1.57 g) was dissolved in 4N hydrochloric acid/1,4-dioxane (23 ml), and the mixture was stirred at room temperature for 1 hour. The residue obtained by concentration and drying of the reaction mixture was dissolved in DMF (15 ml), and subjected to the condensation reaction using N-(tert-butoxycarbonyl)-L-proline (1.00 g), N-methylmorpholine (0.51 ml), HOBt (0.75 g) and DCC (0.96 g) in the same manner as in Example 46-C) to give 1.41 g of the title compound.

C) (2S)-2-[1-Hydroxy-2-(4-methoxyphenoxy)ethyl]- 1-[N-(phenoxy-acetyl)-L-prolyl]pyrrolidine (2S)-1-[N-(tert-Butoxycarbonyl)-L-prolyl]-2-[1-hydroxy-2( 4-methoxyphenoxy)ethyl]pyrrolidine (658 mg) was dissolved in 4N hydrochloric acid/1,4-dioxane (8 ml), and the mixture was stirred at room temperature for 0.5 hour. The residue obtained by concentration and drying of the reaction mixture was dissolved in methylene chloride (10 ml), and thereto were added dropwise triethylamine (0.42 ml) and phenoxyacetyl chloride (0.21 ml) under ice-cooling. After stirring the mixture under ice-cooling for 0.5 hour, and then at room temperature for 2 hours, the reaction mixture was treated in the same manner as in Example 46-D) to give 531 mg of the title compound.

D) (2S)-2-(4-Methoxyphenoxyacetyl)-1-[N-(phenoxyacetyl)-L-prolyl]pyrrolidine (2S)-2-[1-[Hydroxy-2-(4-methoxyphenoxy)ethyl]- 1-[N-(phenoxyacetyl)-L-prolyl]pyrrolidine (478 mg) was dissolved in DMSO (3.5 ml), and benzene (1.5 ml) and triethylamine (0.7 ml) were added thereto. The mixture was cooled on ice, and sulfur trioxide-pyridine complex (730 mg) was added by small portions, after which triethylamine (0.25 ml) was additionally added to keep the reaction mixture neutral. After stirring the mixture at 5°–10° C. for 1 hour, the reaction mixture was poured into ice-water, and extracted with ethyl acetate. The organic layer was washed with 1N hydrochloric acid, saturated aqueous sodium bicarbonate, and saturated brine successively, dried over anhydrous magnesium sulfate, and concentrated. The residue was purified by silica gel column chromatography (eluate: chloroform-methanol) to give 405 mg of the title compound.

EXAMPLE 48

(2S)-2-(4-Methoxyphenoxyacetyl)-1-[N-(N-phenylglycyl)-L-prolyl]pyrrolidine (Compound 48)

A) N-(tert-Butoxycarbonyl)-N-phenylglycine

N-Phenylglycine (5.00 g) was dissolved in 1,4-dioxane-water (2:1, 90 ml), and 1N sodium hydroxide (33.1 ml) and di-tert-butyldicarbonate (7.95 g) were added thereto under ice-cooling, followed by stirring at room temperature overnight. After concentrating the mixture, the residue was dissolved in 10% citric acid, and extracted with ethyl acetate. The organic layer was washed with saturated brine, dried over anhydrous magnesium sulfate, and concentrated. The residue was purified by silica gel column chromatography (eluate: chloroform-methanol-acetic acid) to give 8.30 g of the title compound.

B) (2S)-1-{N-[N-(tert-Butoxycarbonyl)-N-phenylglycyl]-L-prolyl}- 2-[1-hydroxy-2-(4-methoxyphenoxy)ethyl]pyrrolidine (2S)-1-[N-(tert-Butoxycarbonyl)-L-prolyl]-2-[1-hydroxy- 2-(4-methoxyphenoxy)ethyl]pyrrolidine (633 mg) prepared in Example 47-B) was dissolved in 4N hydrochloric acid/1,4-dioxane (6 ml), and the mixture was stirred at room temperature for 0.5 hour. The residue obtained by concentration and drying of the reaction mixture, and N-(tert-butoxycarbonyl)-N-phenylglycine (340 mg) were dissolved in DMF (10 ml), and N-methylmorpholine (0.15 ml) and HOBt (219 mg) were added thereto. After cooling the reaction mixture on ice, water-soluble carbodiimide hydrochloride (263 mg) was added thereto, and the mixture was stirred for 3 hours, and then at room temperature overnight. The reaction mixture was poured into ice-water, and extracted with ethyl acetate. The organic layer was washed with 10% citric acid, and saturated aqueous sodium bicarbonate successively, dried over anhydrous magnesium sulfate, and concentrated. The residue was purified by silica gel column chromatography (eluate: chloroform-methanol) to give 693 mg of the title compound.

C) (2S)-2-[1-Hydroxy-2-(4-methoxyphenoxy)ethyl]-1-[N-(N-phenylglycyl)-L-prolyl]pyrrolidine (2S)-1-{N-[N-(tert-Butoxycarbonyl)-N-phenylglycyl]-L-prolyl}-2-[1-hydroxy- 2-(4-methoxyphenoxy)ethyl]pyrrolidine (656 mg) was dissolved in 4N hydrochloric acid/1,4-dioxane (5 ml) and the mixture was stirred at room temperature for 0.5 hour. The reaction mixture was concentrated, and the resultant residue was dissolved in saturated aqueous sodium bicarbonate, followed by extraction with chloroform. The organic layer was washed with saturated brine, dried over anhydrous magnesium sulfate, and concentrated to give 518 mg of the title compound.

D) (2S)-2-(4-Methoxyphenoxyacetyl)-1-[N-(N-phenylglycyl)-L-prolyl]pyrrolidine (2S)-2-[1-Hydroxy-2-(4-methoxyphenoxy)ethyl]-1-[N-(N-phenylglycyl)-L-prolyl]pyrrolidine (488 mg) was treated in the same manner as in Example 47-D) using DMSO (3 ml), benzene (1.5 ml), triethylamine (0.73 ml+0.15 ml), and sulfur trioxide-pyridine complex (778 mg) to give 288 mg of the title compound.

EXAMPLE 49

(2S)-2-(4-Methoxyphenoxyacetyl)-1-{N-[(phenylthio)acetyl]-L-prolyl}pyrrolidine (Compound 49)

A) (2S)-2-[1-Hydroxy-2-(4-methoxyphenoxy)ethyl]- 1-{N-[(phenylthio)acetyl]-L-prolyl}pyrrolidine (2S)-1-[N-(tert-Butoxycarbonyl)-L-prolyl]-2-[1-hydroxy- 2-(4-methoxyphenoxy)ethyl]pyrrolidine (622 mg) prepared in Example 47-B) was dissolved in 4N hydrochloric acid/1,4-dioxane (6 ml), and the mixture was stirred at room temperature for 0.5 hour. The residue obtained by concentration and drying of the reaction mixture was dissolved in a mixture of methylene chloride (15 ml) and DMF (5 ml), and N-methylmorpholine (0.14 ml), (phenylthio)acetic acid (210 mg), HOBt (190 mg), and water-soluble carbodiimide hydrochloride (242 mg) were added thereto under ice-cooling, followed by stirring for 0.5 hour. After stirring the mixture at room temperature overnight, the reaction mixture was treated in the same manner as in Example 48-B) to give 664 mg of the title compound.

B) (2S)-2-(4-Methoxyphenoxyacetyl)- 1-{N-[(phenylthio)acetyl]-L-prolyl}pyrrolidine (2S)-2-[1-Hydroxy-2-(4-methoxyphenoxy)ethyl]- 1-{N-[(phenylthio)acetyl]-L-prolyl}pyrrolidine (620 mg) was treated in the same manner as in Example 47-D) using DMSO (10 ml), benzene (5 ml), triethylamine (0.90 ml), and sulfur trioxide-pyridine complex (960 mg) to give 510 mg of the title compound.

EXAMPLE 50

(2S)-1-{N-[(1-Adamantyl)methoxycarbonyl]-L-prolyl}-2-( 4-methoxyphenoxyacetyl)pyrrolidine (Compound 50)

A) N-[(1-Adamantyl)methoxycarbonyl]-L-proline benzyl ester

To a solution of trichloromethyl chloroformate (0.36 ml) THF (40 ml) was dropwise added a solution of 1-adamantane methanol (1.00 g) and triethylamine (0.84 ml) in THF (20 ml) under ice-cooling. After stirring the mixture at room temperature for 1.5 hours, a solution of 1,-proline benzyl ester (1.45 g) in methylene chloride (15 ml) was added thereto, followed by dropwise addition of triethylamine (1.7 ml). After stirring the mixture at room temperature for 20 minutes, the reaction mixture was poured into water and extracted with ethyl acetate.

The organic layer was washed with 1N hydrochloric acid, and then with saturated aqueous sodium bicarbonate, dried over anhydrous magnesium sulfate, and concentrated. The residue was purified by silica gel column chromatography (eluate: hexane-ethyl acetate) to give 2.10 g of the title compound.

B) N-[(1-Adamantyl)methoxycarbonyl]-L-proline

To a solution of N-[(1-adamantyl)methoxycarbonyl]-L-proline benzyl ester (1.98 g) in methanol (60 ml) was added 10% Pd-C (0.20 g), and the mixture was stirred at room temperature under hydrogen atmosphere for 1.5 hours. The catalyst was filtered off, and the filtrate was concentrated to give 1.53 g of the title compound.

C) (2S)-1-{N-[(1-Adamantyl)methoxycarbonyl]-L-prolyl}-2-[1-hydroxy-2-(4-methoxyphenoxy)ethyl]pyrrolidine (2S)-1-(tert-Butoxycarbonyl)-2-[1-hydroxy-2-(4-methoxyphenoxy)ethyl]pyrrolidine (1.40 g) prepared in Example 47-A) was dissolved in 4N hydrochloric acid/1,4-dioxane (40 ml), and the mixture was stirred at room temperature for 0.5 hour, followed by concentration to dryness. The residue was subjected to dehydration-condensation with N-[(1-adamantyl)-methoxycarbonyl]-L-proline (1.16 g) in the same manner as in Example 48-B) to give 1.56 g of the title compound.

D) (2S)-1-{N-[(1-Adamantyl)methoxycarbonyl]-L-prolyl}-2-(4-methoxyphenoxyacetyl)pyrrolidine (2S)-1-{N-[(1-Adamantyl)methoxycarbonyl]-L-prolyl}-2-[1-hydroxy-2-(4-methoxyphenoxy)ethyl]pyrrolidine (1.40 g) was oxidized with sulfur trioxide-pyridine complex in the same manner as in Example 47-D) to give 0.98 g of the title compound.

EXAMPLE 51

(2S)-1-[N-(Benzylaminocarbonyl)-L-thioprolyl]-2-(phenoxyacetyl)pyrrolidine (Compound 51)

A) (2S)-1-[N-(tert-Butoxycarbonyl)-L-thioprolyl]-2-(1-hydroxy-2-phenoxyethyl)pyrrolidine (2S)-1-(tert-Butoxycarbonyl)-2-(1-hydroxy-2-phenoxyethyl)pyrrolidine (3.00 g) prepared in Example 46-B) was dissolved in 4N hydrochloric acid/1,4-dioxane (30 ml), and the mixture was stirred at room temperature for 0.5 hour. The reaction mixture was concentrated to dryness. The residue was subjected to dehydration-condensation with N-(tert-butoxycarbonyl)-L-thioproline (2.50 g) in the same manner as in Example 48-B) to give 2.49 g of the title compound.

B) (2S)-1-[N-Benzylaminocarbonyl)-L-thioprolyl]-2-(1-hydroxy-2-phenoxyethyl)pyrrolidine (2S)-1-[N-(tert-Butoxycarbonyl)-L-thioprolyl]-2-( 1-hydroxy2-phenoxyethyl)pyrrolidine (2.47 g) was dissolved in 4N hydrochloric acid/1,4-dioxane (15 ml), and the mixture was stirred at room temperature for 0.5 hour, followed by concentration to dryness. To a solution of the residue in methylene chloride (50 ml) were dropwise added triethylamine (0.90 ml) and benzyl isocyanate (0.80 ml) under ice-cooling, and the mixture was stirred for 1.5 hours. The reaction mixture was poured into ice-water, and extracted with ethyl acetate. The organic layer was washed with 1N hydrochloric acid, saturated aqueous sodium bicarbonate, and saturated brine successively, dried over anhydrous magnesium sulfate, and concentrated. The residue was purified by silica gel column chromatography (eluate: chloroform-methanol) to give 1.95 g of the title compound.

C) (2S)-1-[N-(Benzylaminocarbonyl)-L-thioprolyl]-2-(phenoxyacetyl)pyrrolidine (2S)-1-[N-Benzylaminocarbonyl)-L-thioprolyl]-2-( 1-hydroxy2-phenoxyethyl)pyrrolidine (1.80 g) was oxidized using sulfur trioxide-pyridine complex in the same manner as in Example 47D) to give 1.40 g of the title compound.

EXAMPLE 52

(2S)-1-{N-[N-Benzyl-N-(ethoxycarbonylmethyl)aminocarbonyl]-L-prolyl}-2-(phenoxyacetyl)pyrrolidine (Compound 52)

A) (2S)-1-{N-[N-Benzyl-N-(ethoxycarbonylmethyl)aminocarbonyl]-L-prolyl}- 2-(1-hydroxy-2-phenoxyethyl)pyrrolidine In the same manner as in Example 50-A), 2.12 g of the title compound was obtained by using trichloromethyl chloroformate (0.37 ml), N-benzylglycine ethyl ester (1.2 ml), and (2S)- 2-(1-hydroxy-2-phenoxyethyl)-1-(L-prolyl)pyrrolidine hydrochloride (1.75 g) obtained by treating, with hydrochloric acid, (2S)- 1[N-(tert-butoxycarbonyl)-L-prolyl]-2-(1-hydroxy-2-phenoxyethyl) pyrrolidine prepared in Example 46-C).

B) (2S)-1-{N-[N-Benzyl-N-(ethoxycarbonylmethyl)aminocarbonyl]-L-prolyl}- 2-(phenoxyacetyl)pyrrolidine (2S)-1-{N-[N-Benzyl-N-(ethoxycarbonylmethyl)aminocarbonyl]-L-prolyl)- 2-(1-hydroxy-2-phenoxyethyl)pyrrolidine (2.00 g) was oxidized using sulfur trioxide-pyridine complex the same manner as in Example 47-D) to give 1.25 g of the title compound.

EXAMPLE 53

(2S)-1-[N-[[(S)-α-(Ethoxycarbonyl)benzylamino]carbonyl] -L-prolyl]- 2-(phenoxyacetyl)pyrrolidine (Compound 53)

A) (2S)-1-[N-[[(S)-α-(Ethoxycarbonyl)benzylamino]carbonyl]-L-prolyl]- 2-(1-hydroxy-2-phenoxyethyl)pyrrolidine In the same manner as in Example 50-A), 1.65 g of the title compound was obtained by using trichloromethyl chloroformate (0.38 ml), L-phenylglycine ethyl ester hydrochloride (1.37 g) and (2S)-2-(1-hydroxy-2-phenoxyethyl)-1-(L-prolyl)pyrrolidine hydrochloride (1.80 g).

B) (2S)-1-[N-[[(S)-α-(Ethoxycarbonyl)benzylamino]carbonyl]-L-prolyl]- 2-(phenoxyacetyl)pyrrolidine (2S)-1-[N-[[(S)-α-(Ethoxycarbonyl)benzylamino]carbonyl]-L-prolyl]- 2-(1-hydroxy-2-phenoxyethyl)pyrrolidine (1.63 g) was oxidized using sulfur trioxide-pyridine complex in the same manner as in Example 47-D) to give 0.95 g of the title compound.

EXAMPLE 54

(2S)-1-[N-(Benzylaminocarbonyl)-L-prolyl]-2-[( 2-pyridyloxy)acetyl]pyrrolidine (Compound 54)

A) (2S)-1-(tert-Butoxycarbonyl)-2-[1-hydroxy-2-(2-pyridyloxy)ethyl]pyrrolidine

In the same manner as in Example 47-A), 1.60 g of the crude product of the title compound was obtained from (2S)-1-(tert-butoxycarbonyl)-2-(1,2-epoxyethyl)pyrrolidine (1.52 g) and 2-pyridinol (1.35 g).

B) (2S)-1-[N-(tert-Butoxycarbonyl)-L-prolyl]-2-[1-hydroxy-2-( 2pyridyloxy)ethyl]pyrrolidine (2S)-1-(tert-Butoxycarbonyl)-2-[1-hydroxy-2-(2-pyridyloxy)-ethyl]pyrrolidine (1.54 g) was dissolved in 4N hydrochloric acid/1,4-dioxane (40 ml), and the mixture was stirred at room temperature for 0.5 hour. The reaction mixture was concentrated and dried, and the resultant residue was subjected to condensation with N-(tert-butoxycarbonyl)-L-proline (1.10 g) in the same manner as in Example 48-B) to give 0.83 g of the title compound.

C) (2S)-1-[N-(Benzylaminocarbonyl)-L-prolyl]-2-[1-hydroxy-2-(2-pyridyloxy)ethyl]pyrrolidine In the same manner as in Example 51-B), 670 mg of the title compound was obtained from (2S)-1-[N-(tert-butoxycarbonyl)-L-prolyl]- 2-[1-hydroxy-2-(2-pyridyloxy)ethyl] pyrrolidine (830 mg).

D) (2S)-1-[N-(Benzylaminocarbonyl)-L-prolyl]-2-[(2-pyridyloxy)-acetyl]pyrrolidine (2S)-1-[N-(Benzylaminocarbonyl)-L-prolyl]-2-[1-hydroxy-2-(2-pyridyloxy)ethyl]pyrrolidine (600 mg) was oxidized using sulfur trioxide-pyridine complex in the same manner as in Example 47D) to give 560 mg of the title compound.

EXAMPLE 55

(2S)-2-(Phenoxyacetyl)-1-{N-[3-(1-piperidinyl)propionyl]-L-prolyl}pyrrolidine (Compound 55)

A) (2S)-2-(1-Hydroxy-2-phenoxyethyl)-1-{N-[3-(1-piperidinyl)-propionyl]-L-prolyl} pyrrolidine (2S)-1-[N-(tert-Butoxycarbonyl)-L-prolyl]-2-(1-hydroxy-2-phenoxyethyl)pyrrolidine (1.46 g) prepared in Example 46-C) was dissolved in 4N hydrochloric acid/1,4-dioxane (10 ml), and the mixture was allowed to stand at room temperature for 15 minutes. The reaction mixture was concentrated, and the resultant residue was subjected to condensation with 1-piperidinepropionic acid (0.63 g) in the same manner as in Example 48-B) to give 1.40 g of the title compound.

B) (2S)-2-(Phenoxyacetyl)-1-{N-[3-(1-piperidinyl)propionyl]-L-prolyl}pyrrolidine (2S)-2-(1-Hydroxy-2-phenoxyethyl)-1-{N-[3-(1-piperidinyl)-propionyl]-L-prolyl}pyrrolidine (1.40 g) was oxidized using sulfur trioxide-pyridine complex in the same manner as in Example 47-D) to give 0.30 g of the title compound.

EXAMPLE 56

(2S)-2-(Phenoxyacetyl)-1-{N-[3-phenyl-2(S)-(1-piperidinyl)-propionyl]-L-prolyl}pyrrolidine (Compound 56)

A) (2S)-3-Phenyl-2-(1-piperidinyl)propionic acid tert-butyl ester

To a solution of L-phenylalanine tert-butyl ester hydrochloride (3.05 g) in DMF (50 ml) were added potassium carbonate (5.38 g) and 1,5-dibromopentane (2.98 g), and the mixture was stirred at 80° C. for 2 hours, and then at room temperature for 22 hours. The reaction mixture was diluted with diethyl ether, washed with water and saturated brine successively, dried over anhydrous sodium sulfate, and concentrated. The residue was purified by silica gel column chromatography (eluate: methylene chloride-methanol) to give 1.24 g of the title compound.

B) (2S)-3-Phenyl-2-(1-piperidinyl)propionic acid hydrochloride (2S)-3-Phenyl-2-(1-piperidinyl)propionic acid tert-butyl ester (800 mg) was dissolved in trifluoroacetic acid (5 ml), and the mixture was stirred at room temperature for 14 hours. The reaction mixture was concentrated, and the residue was dissolved in 4N hydrochloric acid/1,4-dioxane (3 ml), followed by concentration. Diethyl ether was added to the residue, and the precipitated crystals were filtered off to give 524 mg of the title compound.

C) (2S)-2-(1-Hydroxy-2-phenoxyethyl)-1-{N-[3-phenyl-2(S)-(1-piperidinyl)propionyl]-L-prolyl}pyrrolidine The residue obtained by treating, with 4N hydrochloric acid, (2S)-1-[N-(tert-butoxycarbonyl)-L-prolyl]-2-(1-hydroxy-2-phenoxyethyl)pyrrolidine (751 mg) prepared in Example 46-C) was subjected to condensation with (2S)-3-phenyl-2-(1-piperidinyl)propionic acid hydrochloride (500 mg) in the same manner as in Example 48-B) to give 818 mg of the title compound.

D) (2S)-2-(Phenoxyacetyl)-1-{N-[3-phenyl-2(S)-(1-piperidinyl)-propionyl]-L-prolyl}pyrrolidine By oxidizing (2S)-2-(1-hydroxy-2-phenoxyethyl)-1-{N-[3-phenyl-2 (S) -(1 -piperidinyl)propionyl]-L-prolyl}pyrrolidine (818 mg) using sulfur trioxide-pyridine complex in the same manner as i n Example 47-D), 582 mg of the title compound was obtained.

The physiochemical properties of the Compounds 46–56 are shown in Tables 11–13.

TABLE 11

| Comp. No. | Structural Formula | Properties Melting point Optical rotation (CH$_2$OH) | MS(m/2) | $^1$H-NMR (CDCl$_3$, δ value) |
|---|---|---|---|---|
| 46 | (phenyl-O-CH$_2$-C(=O)-N(pyrrolidinone)-C(=O)-CH$_2$-O-phenyl) | colorless amorphous solid [α]$_D$ −56.6° | EI-MS: 436(M$^+$), 301, 232, 204, 107, 77 | 1.8–2.3(8H, m), 3.51, 3.61, 3.74&3.92(total 4H, m each), 4.50&4.62(total 1H, d each, J=14.7Hz), 4.61&4.71(total 1H, d each, J=14.7Hz), 4.70(1H, m), 4.78(1H, d, J=17.1Hz), 4.84(1H, d, J=17.1Hz), 4.89(1H, dd, J=8.1, 5.4Hz), 6.85–7.05(6H, m), 7.25–7.35(4H, m) |
| 47 | (4-OCH$_3$-phenyl-O-CH$_2$-C(=O)-N(pyrrolidinone)-C(=O)-CH$_2$-O-phenyl) | colorless amorphous solid [α]$_D$ −53.1° | CI-MS: 467(MH$^+$), 345, 232, 125 | 1.8–2.3(8H, m), 3.51, 3.62, 3.72&3.93(total 4H, m each), 3.76(3H, s), 4.50& 4.62(total 1H, d each, J=14.1Hz), 4.61&4.71(total H, d each, J=14.1Hz), 4.70(1H, m), 4.72(1H, d, J=16.8Hz), 4.78(1H, d, J=16.8Hz), 4.88(1H, dd, J=8.2, 5.4Hz), 6.83(3H, m), 6.95(2H, m), 7.28(4H, m) |
| 48 | (4-OCH$_3$-phenyl-NH-CH$_2$-C(=O)-N(pyrrolidinone)-C(=O)-CH$_2$-O-phenyl) | colorless amorphous solid | EI-MS: 466(MH$^+$), 359, 231, 203, 106, 77 | 1.8–2.3(8H, m), 3.5–3.75(3H, m), 3.76(3H, s), 3.85–3.95(3H, m), 4.71(1H, d, J=16.8Hz), 4.73(2H, m), 4.77(1H, d, J=16.8Hz), 4.91(1H, dd, J=8.1, 5.3Hz), 6.60(2H, d), 6.71(1H, t), 6.81 (4H, m), 7.18(2H, t) |
| 49 | (4-OCH$_3$-phenyl-S-CH$_2$-C(=O)-N(pyrrolidinone)-C(=O)-CH$_2$-O-phenyl) | colorless oily substance [α]$_D$ −112° | EI-MS: 482(M$^+$), 359, 248, 220, 123 | 1.8–2.25(8H, m), 3.5–3.75(3H, m), 3.73(2H, s), 3.77(3H, s)3.91(1H, m), 4.65(1H, dd, J=7.6, 3.6Hz), 4.70(1H, d, J=17.6Hz), 4.77(1H, d, J=17.6Hz), 4.85(1H, dd, J=8.0, 5.3Hz), 6.83(4H, m), 7.15–7.30(3H, m), 7.44(2H, d, J=7.2Hz) |

TABLE 12

| Comp. No. | Structural Formula | Properties Melting point Optical rotation (CH₃OH) | MS(m/z) | ¹H NMR (CDCl₃, δ value) |
|---|---|---|---|---|
| 50 | | colorless amorphous solid | EI-MS: 524(M⁺), 401, 290, 262, 149 | 1.25~2.25(23H, m), 2.4~3.9(6H, m), 3.76(3H, s), 4.50(1H, m), 4.72(1H, d, J=16.6Hz), 4.79(1H, d, J=16.6Hz), 4.87(1H, m), 6.83(4H, m) |
| 51 | | colorless needles mp 136.0~136.7°C. [α]_D −156° | EI-MS: 453(M⁺), 360, 346, 259, 249, 221, 213, 161 | 1.80~2.25(4H, m), 3.12(1H, dd, J=11.5, 5.6Hz), 3.32(1H, dd, J=11.5, 7.3Hz), 3.61(1H, m), 3.89(1H, m), 4.30(1H, dd, J=14.6, 4.8Hz), 4.48(1H, d, J=7.2Hz), 4.52(1H, dd, J=14.6, 6.2Hz), 4.59(1H, d, J=7.2Hz), 4.74(2H, s), 4.83(1H, dd, J=8.3, 5.6Hz), 5.00(1H, br.t), 5.11(1H, dd, J=7.3, 5.6Hz), 6.90(2H, d, J=7.8Hz)6.98(1H, t, J=7.4Hz), 7.25~7.35(6H, m) |
| 52 | | colorless oily substance [α]_D −54.1° | EI-MS: 521(M⁺), 476, 434, 386, 329, 317, 289, 220, 192 | 1.23(3H, t, J=7.1Hz), 1.80~2.25(8H, m), 3.43~3.63(3H, m), 3.71(1H, d, J=17.7Hz), 3.81(1H, m), 3.97(1H, d, J=17.7Hz), 4.16(2H, q, J=7.1Hz), 4.55(1H, dd, J=16.6Hz), 4.62(1H, d, J=16.6Hz), 4.76(1H, d, J=6.8Hz), 4.79(2H, s), 4.90(1H, dd, J=8.3, 5.3Hz), 6.92(2H, d, J=7.8Hz), 6.97(1H, t, J=7.4Hz), 7.25~7.35(7H, m) |
| 53 | | colorless amorphous solid [α]_D −143° | EI-MS: 507(M⁺), 414, 372, 329, 303, 275, 163, 132 | 1.19(3H, t, J=7.2Hz), 1.80~2.25(8H, m), 3.44(1H, m), 3.52~3.66(2H, m), 3.81(1H, m), 4.04~4.26(2H, m), 4.61(1H, dd, J=8.4, 3.3Hz), 4.77(1H, d, J=16.7Hz), 4.84(1H, d, J=16.7Hz), 4.88(1H, dd, J=8.0, 5.2Hz), 5.50(1H, d, J=6.5Hz), 5.62(1H, d, J=6.5Hz), 6.89(2H, d, J=7.8Hz), 6.97(1H, t, J=7.4Hz), 7.24~7.40(7H, m) |

TABLE 13

| Comp. No. | Structural Formula | Properties Melting point Optical rotation (CH₃OH) | EI-MS (m/z) | ¹H NMR (CDCl₃, δ value) |
|---|---|---|---|---|
| 54 | 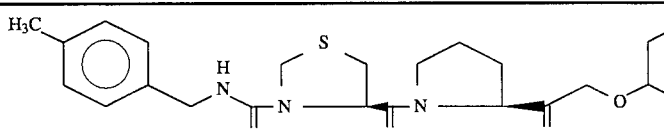 | colorless needles mp 227–228° C. [α]$_D$ −221° C. | EI-MS: 436(M⁺), 302, 285, 231, 203, 190 | 1.85~2.25(8H, m), 3.33 (1H, m), 3.49(1H, m), 3.62(1H, m), 3.87(1H, m), 4.32(1H, dd, J=14.6, 5.0Hz), 4.53(1H, dd, J= 14.6, 6.1Hz), 4.57(1H, d, J=16.9Hz), 4.70(2H, m), 5.09(1H, d, J=16.9Hz), 6.19(1H, td, J=6.7, 1.2Hz), 6.55(1H, d, J= 9.1Hz), 7.2~7.4(8H, m) |
| 55 | | colorless oily substance [α]$_D$−103° | EI-MS: 441(M⁺), 221, 152, 124, 98 | 1.45~2.25(14H, m), 2.55~3.05(8H, m), 3.50~3.75(3H, m), 3.87 (1H, m), 4.64(1H, dd, J=7.8, 3.6Hz), 4.77(1H, d, J=17.5Hz), 4.81, (1H, d, J=17.5Hz), 4.89 (1H, dd, J=8.4, 5.6Hz), 6.90(2H, m), 6.98(1H, m), 7.28(2H, m) |
| 56 | | colorless amorphous solid | EI-MS: 517(M⁺), 427, 188 | 1.35~1.60(6H, m), 1.80~ 2.25(8H, m), 2.50~2.75 (4H, m), 2.94(1H, dd, J=13.9, 5.4Hz), 3.16(1H, dd, J=13.9, 7.9Hz), 3.39 (1H, m), 3.61(2H, m), 3.80(1H, m), 3.97(1H, dd, J=9.4, 6.6, 6.6Hz), 4.70(1H, dd, J=8.0, 3.9Hz), 4.80(1H, d, J= 16.8Hz), 4.86(1H, d, J= 16.8Hz), 4.89(1H, dd, J=8.4, 5.3Hz), 6.90~ 7.02(3H, m), 7.20~ 7.40(7H, m) |

It should be noted that the present invention is not limited to these Examples, and, for example, Compounds 57–72 shown in Table 14 are also within the scope of the invention.

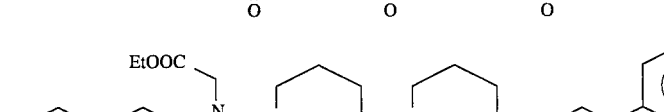

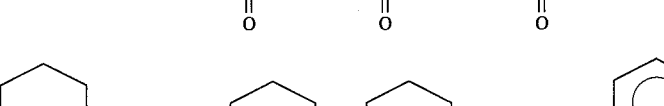

-continued
| Comp. No. | Structural Formula |
|---|---|
| 60 | 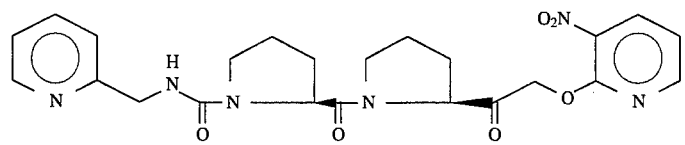 |
| 61 | 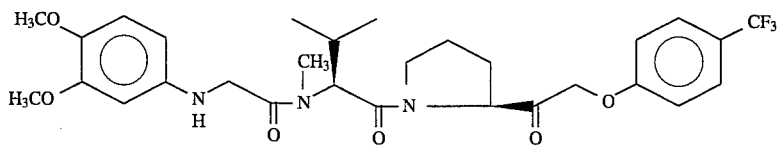 |
| 62 | 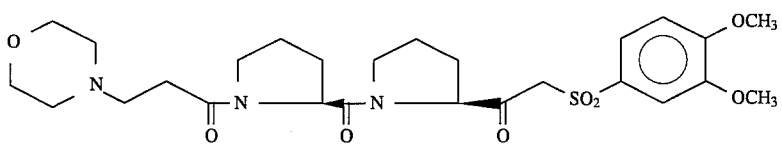 |
| 63 | 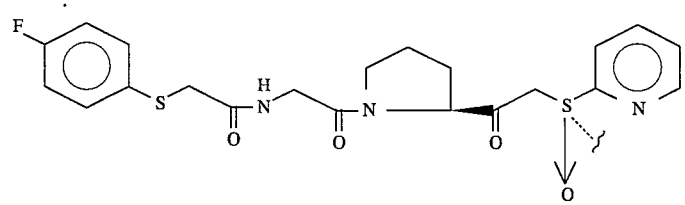 |
| 64 | 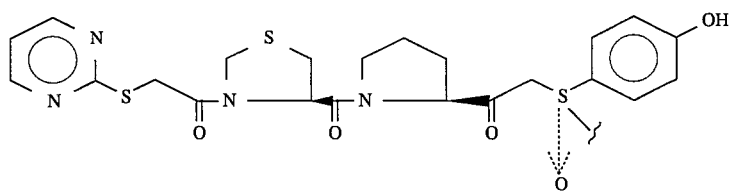 |
| 65 | 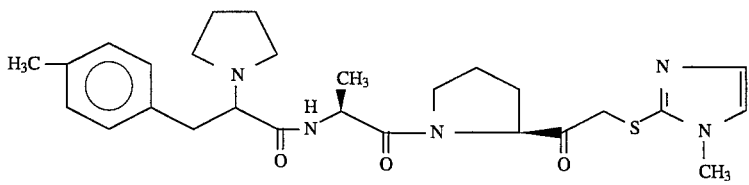 |
| 66 | 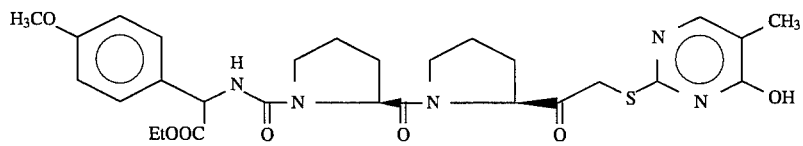 |
| 67 | 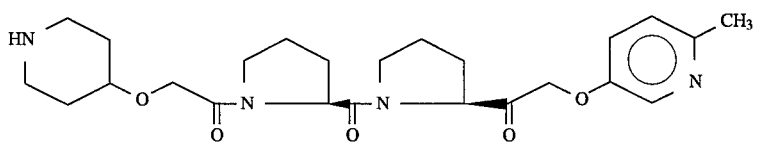 |
| 68 | 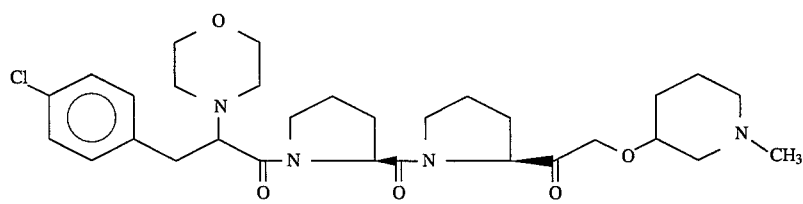 |

-continued

| Comp. No. | Structural Formula |
|---|---|
| 69 | [chemical structure] |
| 70 | [chemical structure] |
| 71 | [chemical structure] |
| 72 | [chemical structure] |

The proline derivatives of the present invention represented by the formula (I) or (I') mentioned above were examined for the in vitro prolyl endopeptidase-inhibitory activity and specificity in inhibitory activities against various proteases.

Experiment Example 1

Prolyl endopeptidase-inhibitory activity

A mixture of a 0.1M potassium sodium phosphate buffer (pH 7.0) (2675 μl), a solution of the compounds of the present invention in a 0.1M potassium sodium phosphate buffer (pH 7.0) (100 μl) and a solution of prolyl endopeptidase extracted from rat brain in a 25 mM sodium phosphate buffer (100 μl) [123 unit/l, pH 6.8, containing 1 mM dithiothreitol and 0.5 mM EDTA, prepared by the method described in J. Neurochem., 35, 527 (1980)]was preincubated at 30° C. for 30 minutes. Thereto was added a 0.2 mM solution of 7-(N-succinyl-glycyl-prolyl)-4-methylcoumarinamide (Peptide Institute, INC.) in a 0.1M potassium sodium phosphate buffer (pH 7.0) (125 μl), and the mixture was incubated at 30° C. for 1 hour. The reaction mixture was immersed in ice (0° C.) to terminate the reaction, and the fluorescence ($a_1$) was determined ten minutes later (excitation at 370 nm and emission at 440 nm). Concurrently, there were conducted the experiment wherein, in the above system, the prolyl endopeptidase solution was substituted for a 25 mM sodium phosphate buffer (pH 6.8, containing 1 mM dithiothreitol and 0.5 mM EDTA) and the experiment wherein the solution of the compounds of the present invention was substituted for a 0.1M potassium sodium phosphate buffer (pH 7.0). Each fluorescence ($a_2$ and $a_3$) was determined respectively [See Tanpakushitsu Kakusan Koso, 29, 127 (1984)]. The prolyl endopeptidase-inhibition rate was calculated by the following formula, and $IC_{50}$, a concentration of a compound producing 50% inhibition, was estimated by semilogarithmic graph paper. The results are summarized in Table 15.

$$\text{Percent inhibition } (\%) = \left(1 - \frac{a_1 - a_2}{a_3 - a_2}\right) \times 100$$

TABLE 15

| Compound No. | IC$_{50}$ (nM) | Compound No. | IC$_{50}$ (nM) |
|---|---|---|---|
| 1 | 0.3 | 22 | 25 |
| 2 | 1.2 | 23 | 15 |
| 3 | 12 | 24 | 0.5 |
| 4 | 0.3 | 25 | 2.5 |
| 5 | 0.3 | 26 | 4.5 |
| 6 | 0.65 | 27 | 2.5 |
| 7 | 1.0 | 28 | 15 |
| 8 | 3.0 | 29 | 0.1 |
| 9 | 0.2 | 30 | 0.6 |
| 10 | 80 | 31 | 4.5 |
| 11 | 1.5 | 32 | 1.0 |
| 12 | 20 | 33 | 1.0 |
| 13 | 0.3 | 46 | 60 |
| 14 | 1.5 | 47 | 50 |
| 15 | 2.5 | 48 | 60 |
| 16 | 1.5 | 49 | 20 |
| 17 | 0.5 | 50 | 500 |
| 18 | 1.5 | 51 | 15 |
| 19 | 15 | 52 | 2.0 |
| 20 | 40 | 53 | 30 |
| 21 | 15 | 54 | 200 |

As is evident from the experiment results, the compound of the present invention was confirmed to have superior inhibitory action on prolyl endopeptidase.

Experiment Example 2

Inhibitory activity against various proteases

The compounds of the present invention were examined for spcificity in inhibitory activities against various proteases. As a result, it was found that the compounds of the present invention specifically inhibited only prolyl endoprotease, as shown in the following Table 16.

Similarly, by following the procedure mentioned above, but employing a 50 mM Tris-HCl buffer (pH 8.0) as a buffer for measurement, a 0.2 μM solution of chymotrypsin

TABLE 16

| Compound No. | Concentration (μM) | prolyl endo-peptidase | trypsin | chymotrypsin | leucine amino-peptidase | elastase | cathepsin B |
|---|---|---|---|---|---|---|---|
| 1 | 0.1 | 90 | 0 | 20 | 0 | 0 | 0 |
| 2 | 0.1 | 100 | 0 | 0 | 0 | 0 | 0 |
| 3 | 0.1 | 91 | 0 | 0 | 0 | 0 | 0 |
| 4 | 0.1 | 98 | 0 | 0 | 0 | 0 | 0 |
| 5 | 0.1 | 98 | 0 | 0 | 0 | 0 | 0 |
| 6 | 0.1 | 98 | 0 | 0 | 0 | 0 | 20 |
| 7 | 0.1 | 97 | 0 | 0 | 0 | 0 | 20 |
| 8 | 0.1 | 92 | 0 | 0 | 0 | 0 | 0 |
| 9 | 0.1 | 98 | 0 | 0 | 0 | 0 | 0 |
| 10 | 0.1 | 97 | 0 | 0 | 0 | 0 | 0 |
| 11 | 0.1 | 90 | 0 | 0 | 0 | 0 | 0 |
| 12 | 1 | 92 | 0 | 0 | 0 | 0 | 0 |
| 13 | 0.1 | 98 | 0 | 0 | 0 | 0 | 0 |
| 14 | 0.1 | 97 | 0 | 0 | 0 | 0 | 0 |
| 15 | 0.1 | 98 | 0 | 0 | 0 | 0 | 0 |
| 16 | 0.1 | 99 | 0 | 0 | 0 | 0 | 0 |
| 17 | 0.1 | 99 | 0 | 0 | 0 | 0 | 0 |
| 18 | 0.1 | 93 | 0 | 0 | 0 | 0 | 0 |
| 19 | 1 | 98 | 0 | 0 | 0 | 0 | 0 |
| 20 | 1 | 96 | 0 | 0 | 0 | 0 | 0 |
| 21 | 1 | 99 | 0 | 0 | 0 | 0 | 0 |
| 22 | 1 | 97 | 0 | 0 | 0 | 0 | 0 |
| 23 | 1 | 99 | 0 | 0 | 0 | 0 | 0 |
| 24 | 0.1 | 99 | 0 | 0 | 0 | 0 | 0 |
| 25 | 0.1 | 97 | 0 | 0 | 0 | 0 | 0 |
| 26 | 1 | 99 | 0 | 0 | 0 | 0 | 0 |
| 27 | 0.1 | 96 | 0 | 0 | 0 | 0 | 0 |
| 28 | 0.1 | 97 | 0 | 0 | 0 | 0 | 0 |
| 29 | 0.1 | 99 | 0 | 0 | 0 | 0 | 0 |
| 30 | 0.1 | 99 | 0 | 0 | 0 | 0 | 0 |
| 31 | 0.1 | 97 | 0 | 0 | 0 | 0 | 0 |
| 32 | 0.1 | 96 | 0 | 0 | 0 | 0 | 0 |
| 33 | 0.1 | 96 | 0 | 0 | 0 | 0 | 0 |
| 46 | 1 | 93 | 0 | 0 | 0 | 0 | 0 |
| 47 | 1 | 98 | 0 | 0 | 0 | 0 | 0 |
| 48 | 1 | 90 | 0 | 0 | 0 | 0 | 0 |
| 49 | 1 | 98 | 0 | 0 | 0 | 0 | 0 |
| 50 | 1 | 97 | 0 | 0 | 0 | 0 | 0 |
| 51 | 1 | 98 | 0 | 0 | 0 | 0 | 0 |
| 52 | 0.1 | 97 | 0 | 0 | 0 | 0 | 0 |
| 53 | 1 | 96 | 0 | 0 | 0 | 0 | 0 |
| 54 | 1 | 85 | 0 | 0 | 0 | 0 | 0 |

The methods for the measurement of inhibitory activities against various proteases and the method for calculating the inhibition rate are as follows.
Determination of trypsin-inhibitory activity In the present invention, a 50 mM Tris-HCl buffer (pH 8.0) was employed as a buffer for measurement.

To a mixture of the above-mentioned buffer (850 μl), a solution of the compounds of the present invention in the same buffer (50 μl) and a 0.02 μM solution of trypsin (derived from bovine pancreas, Sigma) in the same buffer (50 μl) was added a 200 μM solution of 7-(prolyl-phenylaranyl-arginyl)-4-methylcoumarinamide (Peptide Institute, Inc.) in the same buffer (50 μl), and the mixture was incubated at 30° C. for 1 hour. The reaction mixture was immersed in ice (0° C.) to terminate the reaction, and the fluorescence ($b_1$) was determined 1 hour later (excitation at 370 nm and emission at 440 nm). Concurrently, there were conducted the experiment wherein, in the system above, the trypsin solution was substituted for a buffer alone, and the experiment wherein the solution of the compounds of the present invention was substituted for a buffer above. Each fluorescence ($b_2$ and $b_3$) was determined respectively.
Determination of chymotrypsin-inhibitory activity (derived from bovine pancreas, Sigma) in the same buffer as an enzyme solution and a 200 μl solution of 7-(N-succinyl-leucyl-leucyl-valyl-tyrosyl)-4-methylcoumarinamide (Peptide Institute, Inc.) in the same buffer as a substrate solution, each fluorescence ($c_1$, $c_2$ and $c_3$) was determined, respectively.
Determination of leucine aminopeptidase-inhibitory activity Similarly, by following the procedure mentioned above, but employing a 50 mM Tris-HCl buffer (pH 8.0) as a buffer for measurement, a 0.2 mM solution of leucine aminopeptidase (derived from swine kidney, Sigma) in the same buffer as an enzyme solution and a 200 μM solution of 7-leucyl-4-methyl-coumarinamide (Peptide Institute, Inc.) in the same buffer as a substrate solution, each fluorescence ($d_1$, $d_2$ and $d_3$) was determined, respectively.
Determination of elastase-inhibitory activity Similarly, by following the procedure mentioned above, but employing a 1 mM Tris-HCl buffer (pH 8.5) as a buffer for measurement, a 0.2 μM solution of elastase (derived from swine pancreas, Sigma) in the same buffer as an enzyme solution and a 200 μM solution of 7-(N-succinyl-aranyl-prolyl-aranyl)-4-methylcoumarinamide (Peptide Institute, Inc.) in the same buffer as a substrate solution, each fluorescence ($e_1$, $e_2$ and $e_3$) was determined, respectively.
Determination of cathepsin B-inhibitory activity Similarly, by following the procedure mentioned above, but employing a 100 mM sodium phosphate buffer (pH 6.0; containing 1.33 mM EDTA $Na_2$) as a buffer for measurement, a 0.02 μM solution of cathepsin B (derived from bovine spleen, Sigma) in the same buffer as an enzyme solution and a 200 μM solution of 7-(N-benzyloxycarbonyl-phenylaranyl-arginyl)-4-methylcoumarinamide (Peptide Institute, Inc.) in the same buffer as a substrate solution, each fluorescence ($f_1$, $f_2$ and $f_3$) was determined, respectively.

Using the fluorescence $x_1$, $x_2$ and $x_3$ measured in the abovementioned manner, the inhibitory rate against various proteases was calculated by the following formula where x stands for b, c, d, e or f:

$$\text{Percent inhibition (\%)} = \left(1 - \frac{x_1 - x_2}{x_3 - x_2}\right) \times 100$$

The novel proline derivatives of the present invention represented by the formula (I) or (I') exhibit very strong prolyl endopeptidase-inhibitory activities, while they exhibit no or very weak inhibitory activity against proteases such as trypsin, chymotrypsin, leucine aminopeptidase, elastase and cathepsin B. Therefore, it is expected that the compounds of the present invention specifically inhibit decomposition and inactivation of endogeneous peptides containing proline residues, such as TRH, substance P, neurotensin, vasopressin, or the like, which are intracerebral hormones and neurotransmitters, and are considered to be concerned with learning and memory process.

Based on such characteristic properties, the compounds of the present invention are expected to contribute to the improvement of the symptoms of various diseases concerned with hormones and neurotransmitters, and in addition, can be used for the prevention and/or treatment of dementia including Alzheimer's disease and amnesia as agents which act directly on the central symptoms of dementia.

What is claimed is:

1. A proline derivative of the following formula (I)

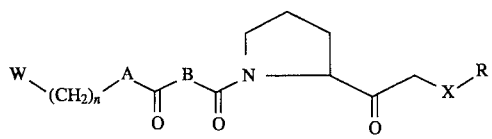
(I)

wherein:

A is —O—, —NH—,

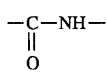

or a single bond;

B is

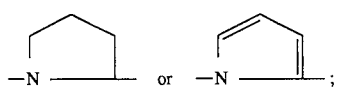

W is

or $CH_3$— where $R^2$ is a hydrogen atom, a halogen atom or a lower alkoxy;

X is —S—, —SO—, —$SO_2$—, —O— or —NH—;

R is

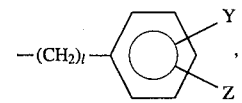

or a lower alkyl having 1 to 5 carbon atoms where l is an integer of 0 to 3, Y and Z are the same or different and each is a hydrogen atom, a halogen atom, a nitro, a hydroxy, a lower alkoxy or a lower alkyl having 1 to 5 carbon atoms which may be substituted by fluorine atoms, and Y and Z may combinedly form a 1,3-dioxolane ring and n is an integer of 1 to 6.

2. A proline derivative according to claim 1, which is selected from the group consisting of (2S)-1-(N-benzyloxycarbonyl-L-prolyl)-2-[(phenylthio)acetyl]pyrrolidine, (2S)-1-(N-benzyloxycarbonyl-L-prolyl)-2-[(phenylsulfinyl)acetyl]pyrrolidine, (2S)- 1-(N-benzyloxycarbonyl-L-prolyl)-2-[(phenylsulfonyl)acetyl]pyrrolidine, (2S)-1-(N-benzyloxycarbonyl-L-prolyl)-2-(phenoxyacetyl)pyrrolidine, (2S)-1-[N-(4-phenylbutyryl)-L-prolyl]-2-[(phenylsulfinyl)acetyl]pyrrolidine, (2S)-1-(N-benzyloxycarbonyl-L-prolyl)-2-[(4-methoxyphenylsulfinyl)acetyl]pyrrolidine, (2S)-1-(N-benzyloxycarbonyl-L-prolyl)-2-[(4-nitrophenylsulfinyl)acetyl]pyrrolidine, (2S)-1-(N-benzyloxycarbonyl-L-prolyl)-2-[(isopropylsulfinyl)-acetyl]pyrrolidine, (2S)-1-(N-benzyloxycarbonyl-L-prolyl)-2-{[(S)-phenylsulfinyl]acetyl}pyrrolidine, (2S)-1-(N-benzyloxycarbonyl-L-prolyl)-2-{[(R)-phenylsulfinyl]phenylsulfinyl]acetyl}pyrrolidine, (2S)-1-(N-benzyloxycarbonyl-L-prolyl)-2-{[(S)-4-methoxyphenylsulfinyl] acetyl}pyrrolidine, (2S)-1-(N-benzyloxycarbonyl-L-prolyl)-2-{[(R)-4-methoxyphenylsulfinyl] acetyl}pyrrolidine, (2S)-1-(N-benzyloxycarbonyl-L-prolyl)-2-{[(S)-p-tolylsulfinyl]acetyl}pyrrolidine, (2S)-1-(N-benzyloxycarbonyl-L-prolyl)-2-{[(R)-p-tolylsulfinyl] acetyl}pyrrolidine, (2S)-2-{[(S)-4-methoxyphenylsulfinyl]acetyl{-1-[N- (3-phenylpropionyl)-L-prolyl]pyrrolidine, (2S)-1-[N-(3-phenylpropionyl)-L-prolyl]-2-{[(S)-p-tolylsulfinyl]acetyl}pyrrolidine, (2S)-1-[N-(3-phenylpropionyl)-L-prolyl]-2-{[(S)-phenylsulfinyl]acetyl}pyrrolidine, (2S)-1-(N-benzyloxycarbonyl-L-prolyl)-2-[(4-methoxyphenoxy)acetyl]pyrrolidine, (2S)-2-(phenoxyacetyl)-1-[N-(3-phenylpropionyl)-L-prolyl] pyrrolidine, (2S)-2-[(4-methoxyphenoxy)acetyl]- 1-[N(3-phenylpropionyl)-L-prolyl]pyrrolidine, (2S)-1-(N-benzylaminocarbonyl-L-prolyl)-2-(phenoxyacetyl)pyrrolidine, (2S)-1-(N-benzylaminocarbonyl-L-prolyl)-2-(4-methoxyphenoxyacetyl)-pyrrolidine, (2S)-1-(N-benzylaminocarbonyl-L-prolyl)- 2-{[(S)-4-methoxyphenylsulfinyl]acetyl}pyrrolidine, (2S)-1-[N-( 4-methoxybenzylaminocarbonyl)-L-prolyl]-2-{[(S)-4-methoxyphenylsulfinyl] acetyl}pyrrolidine, (2S)-1-[N-( 4-methoxybenzylaminocarbonyl)-L-prolyl]-2-(4-methoxyphenoxyacetyl)pyrrolidine, (2S)-2-(4-chlorophenoxyacetyl)-1-[N-(3-phenylpropionyl)-L-prolyl]pyrrolidine, (2S)-2-(4-hydroxyphenoxyacetyl)-1-[N-(3-phenylpropionyl)-L-prolyl]pyrrolidine, (2S)-1-[N-(4-chlorobenzylaminocarbonyl)-L-prolyl]-2-(4-chlorophenoxyacetyl)pyrrolidine, (2S)-1-[N-(4-fluorobenzylaminocarbonyl)-L-prolyl]-2-(4-fluorophenoxyacetyl)pyrrolidine, (2S)-1-[N-(4-chlorobenzylaminocarbonyl)-L-proline]-2-(phenoxyacetyl)pyrrolidine, (2S)-1-(N-octanoyl-L-proline)-2-(phenoxyacetyl)pyrrolidine, (2S)-1-(N-benzylaminocarbonyl)-L-proline)-2-(benzyloxyacetyl)pyrrolidine and (2S)-1-[N-(benzylaminocarbonyl)-L-prolyl]-2-{[(3,4-methylenedioxy)phenoxy]acetyl}pyrrolidine.

3. A pharmaceutical composition containing an effective amount of a proline derivative of the following formula (I)

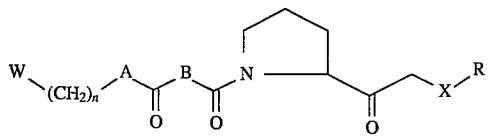

(I)

wherein:

A is —O—, —NH—,

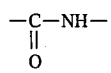

or a single bond;

B is

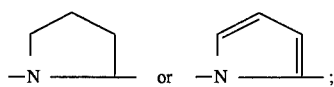

W is

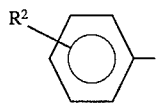

or CH$_3$— where R$^2$ is a hydrogen atom, a halogen atom or a lower alkoxy;

X is —S—, —SO—, —SO$_2$—, —O— or —NH—;

R is or a lower alkyl having 1 to 5 carbon atoms where 1 is an integer of 0 to 3, Y and Z are the same or different and each is a hydrogen atom, a halogen atom, a nitro, a hydroxy, a lower alkoxy or a lower alkyl having 1 to 5 carbon atoms which may be substituted by fluorine atoms, and Y and Z may combinedly form a 1,3-dioxolane ring; and n is an integer of 1 to 6, and a pharmaceutically acceptable diluent.

4. A pharmaceutical composition according to claim 3, wherein the proline derivative is selected from the group consisting of (2S)-1-(N-benzyloxycarbonyl-L-prolyl)-2-[(phenylthio)acetyl]pyrrolidine, (2S)-1-(N-benzyloxycarbonyl-L-prolyl)-2-[(phenylsulfinyl)acetyl]pyrrolidine, (2S)-1-(N-benzyloxycarbonyl-L-prolyl)-2-[(phenylsulfonyl)acetyl]pyrrolidine, (2S)-1-(N-benzyloxycarbonyl-L-prolyl)-2-(phenoxyacetyl)pyrrolidine, (2S)-1-[N-(4-phenylbutyryl)-L-prolyl]-2-[(phenylsulfinyl)acetyl]pyrrolidine, (2S)-1-(N-benzyloxycarbonyl-L-prolyl)-2-[(4-methoxyphenylsulfinyl)acetyl]pyrrolidine, (2S)-1-(N-benzyloxycarbonyl-L-prolyl)-2-[(4-nitrophenylsulfinyl)acetyl]pyrrolidine, (2S)-1-(N-benzyloxycarbonyl-L-prolyl)-2-[(isopropylsulfinyl)-acetyl]pyrrolidine, (2S)-1-(N-benzyloxycarbonyl-L-prolyl)-2-{[(S)-phenylsulfinyl]acetyl}pyrrolidine, (2S)-1-(N-benzyloxycarbonyl-L-prolyl)-2-{[(R)-phenylsulfinyl]acetyl}pyrrolidine, (2S)-1-(N-benzyloxycarbonyl-L-prolyl)-2-{[(S)-4-methoxyphenylsulfinyl]acetyl}pyrrolidine, (2S)-1-(N-benzyloxycarbonyl-L-prolyl)-2-{[(R)-4-methoxyphenylsulfinyl]acetyl}pyrrolidine, (2S)-1-(N-benzyloxycarbonyl-L-prolyl)-2-{[(S)-p-tolylsulfinyl]acetyl}pyrrolidine, (2S)-1-(N-benzyloxycarbonyl-L-prolyl)-2-{[(R)-p-tolylsulfinyl]acetyl}pyrrolidine, (2S)-2-{[(S)-4-methoxyphenylsulfinyl]acetyl}-1-[N-(3-phenylpropionyl)-L-prolyl]pyrrolidine, (2S)-1-[N-(3-phenylpropionyl)-L-prolyl]-2-{[(S)-p-tolylsulfinyl]acetyl}pyrrolidine, (2S)-1-[N-(3-phenylpropionyl)-L-prolyl]-2-{[(S)-phenylsulfinyl]acetyl}pyrrolidine, (2S)-1-(N-benzyloxycarbonyl-L-prolyl)-2-[(4-methoxyphenoxy)acetyl]pyrrolidine, (2S)-2-(phenoxyacetyl)-1-[N-(3-phenylpropionyl)-L-prolyl] pyrrolidine, (2S)-2-[(4-methoxyphenoxy)acetyl]-1-[N-(3-phenylpropionyl)-L-prolyl]pyrrolidine, (2S)-1-(N-benzylaminocarbonyl-L-prolyl)-2-(phenoxyacetyl)pyrrolidine, (2S)-1-(N-benzylaminocarbonyl-L-prolyl)-2-(4-methoxyphenoxyacetyl)pyrrolidine, (2S)-1-(N-benzylaminocarbonyl-L-prolyl)-2-{[(S)-4-methoxyphenylsulfinyl]acetyl}pyrrolidine, (2S)-1-[N-(4-methoxybenzylaminocarbonyl)-L-prolyl]-2-{[(S)-4-methoxyphenylsulfinyl]acetyl}pyrrolidine (2S)-1-[N-(4-methoxybenzylaminocarbonyl)-L-prolyl]-2-(4-methoxyphenoxyacetyl)pyrrolidine, (2S)-2-(4-chlorophenoxyacetyl)-1-[N-(3-phenylpropionyl)-L-prolyl] pyrrolidine, (2S)-2-(4-hydroxyphenoxyaetyl)-1-[N-(3-phenylpropionyl)-L-prolyl]pyrrolidine, (2S)-1-[N-(4-chlorobenzylaminocarbonyl)-L-prolyl]-2-(4-chlorophenoxyacetyl)pyrrolidine, (2S)-1-[N-(4-fluorobenzylaminocarbonyl)-L-prolyl]-2-(4-fluorophenoxyacetyl)pyrrolidine, (2S)-1-[N-(4-chlorobenzylaminocarbonyl)-L-proline]-2-(phenoxyacetyl)pyrrolidine, (2S)-1-(N-octanoyl-L-proline)-2-(phenoxyacetyl)pyrrolidine, (2S)-1-(N-benzylaminocarbonyl)-L-proline)-2-(benzyloxyacetyl)pyrrolidine and (2S)-1-[N-(benzylaminocarbonyl)-L-prolyl]-2-{[(3,4-methylenedioxy)phenoxy]acetyl}pyrrolidine.

* * * * *